United States Patent
Klar et al.

(10) Patent No.: US 9,206,219 B2
(45) Date of Patent: Dec. 8, 2015

(54) 17-HYDROXY-17-PENTAFLUORETHYL-ESTRA-4,9(10)-DIEN-11-ARYL DERIVATIVES, METHODS FOR THE PRODUCTION THEREOF AND THE USE THEREOF FOR TREATING DISEASES

(75) Inventors: Ulrich Klar, Berlin (DE); Wolfgang Schwede, Glienicke (DE); Carsten Möller, Berlin (DE); Andrea Rotgeri, Berlin (DE); Wilhelm Bone, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 691 days.

(21) Appl. No.: 13/386,421

(22) PCT Filed: Jul. 8, 2010

(86) PCT No.: PCT/EP2010/004157
§ 371 (c)(1),
(2), (4) Date: Jun. 25, 2012

(87) PCT Pub. No.: WO2011/009534
PCT Pub. Date: Jan. 27, 2011

(65) Prior Publication Data
US 2012/0258941 A1    Oct. 11, 2012

(30) Foreign Application Priority Data

Jul. 21, 2009  (DE) .................. 10 2009 034 525

(51) Int. Cl.
*A61K 31/57*    (2006.01)
*C07J 7/00*    (2006.01)
*C07J 1/00*    (2006.01)
*C07J 21/00*    (2006.01)
*C07J 41/00*    (2006.01)
*C07J 43/00*    (2006.01)

(52) U.S. Cl.
CPC .............. *C07J 1/0081* (2013.01); *C07J 21/006* (2013.01); *C07J 41/0044* (2013.01); *C07J 41/0094* (2013.01); *C07J 43/003* (2013.01)

(58) Field of Classification Search
CPC ........ C07J 1/0085; C07J 17/00; C07J 21/006; C07J 41/0094; C07J 43/003
USPC .......................................... 552/598; 514/179
See application file for complete search history.

(56) References Cited

U.S. PATENT DOCUMENTS

| | | |
|---|---|---|
| 4,386,085 A | 5/1983 | Teutsch et al. |
| 4,609,651 A | 9/1986 | Rohde et al. |
| 4,634,695 A | 1/1987 | Torelli et al. |
| 4,900,725 A | 2/1990 | Nioue et al. |
| 4,921,846 A | 5/1990 | Nedelec et al. |
| 4,954,490 A | 9/1990 | Cook et al. |
| 5,073,548 A | 12/1991 | Cook et al. |
| 5,108,996 A | 4/1992 | Claussner et al. |
| 5,272,140 A | 12/1993 | Loozen |
| 5,407,928 A | 4/1995 | Kasch et al. |
| 5,712,264 A | 1/1998 | Hamersma et al. |
| 5,739,125 A | 4/1998 | Kasch et al. |
| 5,986,115 A | 11/1999 | Bohlmann et al. |
| 6,020,328 A | 2/2000 | Cook et al. |
| 6,042,324 A | 3/2000 | Aggarwal et al. |
| 6,225,298 B1 | 5/2001 | Spicer et al. |
| 6,316,432 B1 | 11/2001 | Schwede et al. |
| 6,476,079 B1 | 11/2002 | Jukarainen et al. |
| 6,503,895 B2 | 1/2003 | Schwede et al. |
| 6,806,263 B2 | 10/2004 | Schwede et al. |
| 6,825,182 B2 | 11/2004 | Ring et al. |
| 6,861,415 B2 | 3/2005 | Kim et al. |
| 7,087,591 B2 | 8/2006 | Kim et al. |
| 7,148,213 B2 | 12/2006 | Schwede et al. |
| 7,910,573 B2 | 3/2011 | Beckmann et al. |
| 8,053,426 B2 | 11/2011 | Fuhrmann et al. |
| 2001/0016578 A1 | 8/2001 | Spicer et al. |
| 2002/0045774 A1 | 4/2002 | Schwede et al. |
| 2002/0143000 A1 | 10/2002 | Hegele-Hartung et al. |
| 2003/0069434 A1 | 4/2003 | Bohlmann et al. |
| 2003/0191099 A1 | 10/2003 | Bohlmann et al. |
| 2004/0006241 A1 | 1/2004 | Grawe et al. |
| 2004/0048841 A1 | 3/2004 | Hoffmann et al. |
| 2004/0157811 A1 | 8/2004 | Lichtner et al. |
| 2005/0080060 A1 | 4/2005 | Schwede et al. |
| 2005/0277769 A1 | 12/2005 | Burton et al. |
| 2007/0105828 A1 | 5/2007 | Joshi et al. |
| 2009/0075989 A1 | 3/2009 | Schwede et al. |
| 2011/0112057 A1 | 5/2011 | Fuhrmann et al. |

(Continued)

FOREIGN PATENT DOCUMENTS

| | | |
|---|---|---|
| CA | 2280041 A1 | 8/1998 |
| EP | 0057115 A2 | 4/1982 |

(Continued)

OTHER PUBLICATIONS

Bagaria, et al.,"Low-dose Mifepristone in Treatment of Uterine Leiomyoma: A Randomized Double-blind Placebo-controlled Clinical Trial," Australian and New Zealand Journal of Obstetrics and Gynaecology, 2009, 49:77-83.

(Continued)

*Primary Examiner* — Barbara P Badio
(74) *Attorney, Agent, or Firm* — Karen B. King

(57) ABSTRACT

The invention relates to 17-hydroxy-17-pentafluoroethyl-estra-4,9(10)-diene 11-aryl derivatives of the formula I with progesterone-antagonizing action and to processes for preparation thereof, to use thereof for treatment and/or prophylaxis of disorders and to the use thereof for production of medicaments for treatment and/or prophylaxis of disorders, especially of fibroids of the uterus (myomas, uterine leiomyomas), endometriosis, heavy menstrual bleeds, meningiomas, hormone-dependent breast cancers and complaints associated with the menopause, or for fertility control and emergency contraception.

12 Claims, No Drawings

(56) References Cited

U.S. PATENT DOCUMENTS

| | | |
|---|---|---|
| 2012/0149670 A1 | 6/2012 | Schwede et al. |
| 2012/0184515 A1 | 7/2012 | Klar et al. |
| 2012/0190660 A1 | 7/2012 | Klar et al. |
| 2012/0232042 A1 | 9/2012 | Klar et al. |
| 2012/0316145 A1 | 12/2012 | Klar et al. |
| 2013/0005697 A1 | 1/2013 | Schwede et al. |
| 2013/0072464 A1 | 3/2013 | Schwede et al. |

FOREIGN PATENT DOCUMENTS

| | | |
|---|---|---|
| EP | 0411733 | 2/1991 |
| EP | 0676203 | 10/1995 |
| EP | 0970103 B1 | 4/2002 |
| EP | 1862468 | 12/2007 |
| IN | 978MUM2005 | 8/2005 |
| JP | H11171774 | 6/1999 |
| WO | 9603130 A1 | 2/1996 |
| WO | 9615794 | 5/1996 |
| WO | 9805679 | 2/1998 |
| WO | 9807740 | 2/1998 |
| WO | 9826783 | 6/1998 |
| WO | WO 98/34947 * | 8/1998 |
| WO | 9933855 | 7/1999 |
| WO | 9953924 | 10/1999 |
| WO | 0147490 | 7/2001 |
| WO | 0232429 A2 | 4/2002 |
| WO | 03045972 A1 | 6/2003 |
| WO | 03093292 | 11/2003 |
| WO | 2006010097 A2 | 1/2006 |
| WO | 2008058767 A1 | 5/2008 |
| WO | 2009138186 A2 | 11/2009 |
| ZA | 977482 | 2/1998 |

OTHER PUBLICATIONS

Bohl, et al.,"Molecular Mechanics and X-ray Crystal Structure Investigations in Conformations of 11β Substituted 4,9-dien-3-one Steroids," J. Mol. Graphics, Sep. 1989, 7:122-153.

Braga, et al.,"Crystal Polymorphism: Challenges at the Crossroads of Science and Technology," Making Crystals by Design, 2007, pp. 293-314.

Cabri, et al.,"Polymorphisms and Patent, Market, and Legal Battles: Cefdinir Case Study," Organic Process Research & Development, 2007, 11(1):64-72.

Caira,"Crystalline Polymorphism of Organic Compounds," Topics in Current Chemistry, 1998, 198: 164-208.

Chwalisz, et al.,"A Randomized, Controlled Trial of Asoprisnil, a Novel Selective Progesterone Receptor Modulator, in Women with Uterine Leiomyomata," Fertility and Sterility, Jun. 2007, 87(6):1399-1412.

Davey,"Solvent Effects in Crystallisation Processes," CurrentTopics in Material Science, 1982,8: 429-479.

English Transl. of Office Action for European Appl. No. 06 090 095 dated Jan. 16, 2007 (U.S. Pat. No. 7,910,573 B2).

Fuhrmann, et al.,"Synthesis and Biological Activity of a Novel, Highly Potent Progesterone Receptor Antagonist," J. Med. Chem., 2000, 43:5010-5016.

Hazra, et al.,"Mifepristone (RU-486), the Recently Developed Antiprogesterone Drug and its Analogues," J. Indian Inst. Sci, May-Jun. 2001, 81:287-298.

Kettel, et al.,"Treatment of Endometriosis with the Antiprogesterone Mifepristone (RU486)," Fertility and Sterility, Jan. 1996, 65(1):23-28.

Kettel, et al.,"Endocrine Responses to Long-term Administration of the Antiprogesterone RU486 in Patients with Pelvic Endometriosis," Fertility and Sterility, Sep. 1991, 56(3):402-407.

Kettel, et al.,"Preliminary Report on the Treatment of Endometriosis with Low-dose Mifepristone (RU 486)," Am. J. Obstst. Gynecol., Jun. 1998, 178(6):1151-1156.

Maibauer, et al.,"First Human Data for ZK 230211 (ZK-PRA), a New Progesterone Receptor Antagonist: A Phase I Clinical Analysis of Safety and Pharmacokinetics in Healthy Postmenopausal Woment," Abstracts—Poster Session IV, 2006, N. 4074.S196.

Möller, et al.,"Investigational Developments for the Treatment of Progesterone-dependent Diseases," Expert Opin. Investig. Drugs, 2008, 17(4):469-479.

Murphy, et al.,"Regresssion of Uterine Leiomyomata in Response to the Antiprogesterone RU 486," J. Clin. Endocrinol. Metab., 1993, 76(2):513-517.

Patani, et al.,"Bioisosterism: A Rational Approach in Drug Design," Chem. Rev., 1996, 96:3147-3176.

Steinauer, et al.,"Systematic Review of Mifepristone for the Treatment of Uterine Leiomyomata," Obstetrics & Gynecology, Jun. 2004, 103(6):1331-1336.

Tellekson, et al.,"Strategies for Attacking and Defending Pharmaceutical Patents: A Modern Take on the Art of War," Intellectual Property & Technology Law Journal, Dec. 2005, 17(12):5-14.

Van Geerestein, et al.,"Structure of the n-Butul Acetate Solvate of 11β-[4-(Dimethylamino)phelyl]-17β-hydroxy-17α-(1-propynyl)estra-4,9-dien-3-one," Acta Cryst., 1986, C42:1521-1523.

Vippagunta, et al.,"Crystalline Solids," Advanced Drug Delivery Reviews, 2001, 48:3-26.

English Language Translation of EP0411733, 1991.

English Language Translation of EP0676203, 1995.

English Language Translation of WO1998/026783.

English Language Translation of WO1999/053924.

English Language Abstract of JP H11171774 (corresponding to Japanese Patent Application No. 19970335723), 1997.

English Language Abstract of WO 2003/093292.

U.S. Appl. No. 13/386,420 371(c) date Apr. 5, 2012, published as US 2012-0190660.

U.S. Appl. No. 13/376,512 371(c) date Feb. 27, 2012, published as US 2012-0149670.

U.S. Appl. No. 13/577,799, 371(c) date Sep. 21, 2012, published as US 2013-0005697.

U.S. Appl. No. 13/578,500 371(c) date Oct. 1,2012, published as US 2013-0072464.

U.S. Appl. No. 13/386,031 371(c) Aug. 28, 2012, published as US 2012-0316145.

* cited by examiner

17-HYDROXY-17-PENTAFLUORETHYL-ESTRA-4,9(10)-DIEN-11-ARYL DERIVATIVES, METHODS FOR THE PRODUCTION THEREOF AND THE USE THEREOF FOR TREATING DISEASES

The invention relates to 17-hydroxy-17-pentafluoroethyl-estra-4,9(10)-diene 11-aryl derivatives of the formula I with progesterone-antagonising action and to processes for preparation thereof, to use thereof for treatment and/or prophylaxis of disorders and to the use thereof for production of medicaments for treatment and/or prophylaxis of disorders, especially of fibroids of the uterus (myomas, uterine leiomyomas), endometriosis, heavy menstrual bleeds, meningiomas, hormone-dependent breast cancers and complaints associated with the menopause, or for fertility control and emergency contraception.

These compounds are valuable active pharmaceutical ingredients. They can be used, inter alia, for production of pharmaceutical formulations for treatment of fibroids of the uterus or of endometriosis, heavy menstrual bleeds, meningiomas, hormone-dependent breast cancers and complaints associated with the menopause, or for fertility control and emergency contraception. For treatment of uterus fibroids and of endometriosis, the inventive compounds can also be administered sequentially in combination with gestagens. Within such a treatment regime, the inventive compounds could be administered over a period of 1-6 months, followed by a pause in treatment or sequential treatment with a gestagen over a period of 2-6 weeks, or followed by treatment with an oral contraceptive (OC combinations) over the same period.

The efficacy of the inventive compounds as a progesterone receptor antagonist has been shown in vitro in transactivation tests.

Compounds with antagonistic action on the progesterone receptor (competitive progesterone receptor antagonists) became known for the first time in 1982 (RU 486; EP57115) and have been described many times since then. Progesterone receptor antagonists with a fluorinated 17α side chain were published in WO 98/34947 and Fuhrmann et al., J. Med. Chem. 43, 5010-5016 (2000).

The compounds with a fluorinated 17α side chain described in WO 98/34947 generally have very strong antagonistic activity on the progesterone receptor. Very potent compounds which are therefore preferred in WO 98/34947 are 11β-(4-acetylphenyl)-20,20,21,21,21-pentafluoro-17-hydroxy-19-nor-17α-pregna-4,9-dien-3-one, 11β-(4-acetylphenyl)-20,20,21,21,21-pentafluoro-17-hydroxy-19-nor-17α-pregna-4-en-3-one and 6'-acetyl-9,11β-dihydro-17β-hydroxy-17α-(1,1,2,2,2-pentafluoroethyl)-4'H-naphth[3',2',1':10,9,11]ester-4-en-3-one. These compounds are converted to various metabolites to a considerable degree in vivo, some of which have strong pharmacological activity, some of them lesser pharmacological activity. The metabolism occurs predominantly at the 4 substituent of the 11-phenyl radical. WO2008/058767 describes compounds of which at least some are metabolites of the compounds described in WO 98/34947.

It is an object of the present invention to provide highly potent competitive progesterone receptor antagonists and hence alternative possible treatments of gynaecological disorders.

It has been found that the inventive compounds are particularly suitable for achieving this object.

The present invention relates to 17-hydroxy-17-pentafluoroethylestra-4,9(10)-diene 11-aryl derivatives with the general chemical formula I:

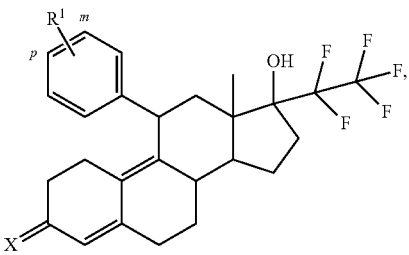

in which
$R^1$ is either defined as the $R^{1a}$ radical joined to the phenyl ring in the m or p position, or defined as the $R^{1b}$ radical joined to the phenyl ring exclusively in the m position,
$R^{1a}$ is selected from the group comprising $(CH_2)_n$—$R^2$, $C(R^3)_2OH$, CN, $C(CH_2OH)_2R^3$, $C(CH_2OCH_2)R^3$,

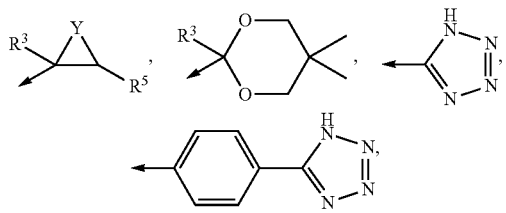

$R^{1b}$ is selected from the group comprising $C_2$-$C_{10}$-acyl, CHOHalkyl,
$R^2$ is selected from the group comprising aryl, heteroaryl, halogen, CN, $N_3$, OH, $NHCONHR^4$, $OCONHR^4$, $NHCOR^4$,
$R^3$ is selected from the group comprising hydrogen, $C_1$-$C_{10}$-alkyl,
$R^4$ is selected from the group comprising hydrogen, $C_1$-$C_{10}$-alkyl, $C_2$-$C_{10}$-alkenyl, $C_7$-$C_{20}$-aralkyl, aryl, heteroaryl, $(CH_2)_qCO_2R^5$,

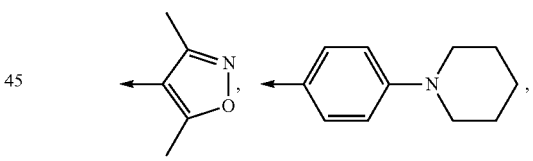

n is 1 or 2,
q is 1 to 10,
$R^5$ is selected from the group comprising hydrogen, $C_1$-$C_{10}$-alkyl, $CH_2OH$,
X is selected from the group comprising oxygen, an $NOR^6$ or $NNHSO_2R^6$ group,
Y is selected from the group comprising oxygen, $CHR^6$ or $NR^6$,
$R^6$ is selected from the group comprising hydrogen, $C_1$-$C_{10}$-alkyl, aryl, $C_7$-$C_{20}$-aralkyl and the salts, solvates or solvates of the salts thereof, including all crystal polymorphs, the α-, β- or γ-cyclodextrin clathrates, and the compounds encapsulated with liposomes.

The arrow in the substructures shown above means the point at which they are joined to the structure according to formula I.

Depending on their structure, the inventive compounds of the general formula I can exist in stereoisomeric forms (enantiomers, diastereomers). The invention therefore encompasses the enantiomers or diastereomers and the particular mixtures thereof, including the racemates. It is possible to isolate the stereoisomerically homogeneous constituents from such mixtures of enantiomers and/or diastereomers in a known manner.

Each of the said substituents on the steroid backbone may be either in an α position or in a β position. In addition, it is also possible for the substituents on the steroid backbone which contain a double bond and in which the double bond bears at least one non-hydrogen substituent on each atom to be present either in E or Z configuration.

When the inventive compounds can occur in tautomeric forms, the present invention encompasses all tautomeric forms.

Preferred salts in the context of the present invention are physiologically compatible salts of the inventive compounds. Also included, however, are salts which are themselves unsuitable for pharmaceutical applications but can be used, for example, for the isolation or purification of the inventive compounds.

Physiologically compatible salts of the inventive compounds include—when a basic function is present—salts with inorganic or organic acids, especially of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid or benzoic acid.

Physiologically compatible salts of the inventive compounds include—when an acidic function is present—alkali metal salts, alkaline earth metal salts or ammonium salts, as obtainable by reaction with corresponding inorganic or organic bases. Preferred examples include alkali metal salts (e.g. sodium and potassium salts), alkaline earth metal salts (e.g. calcium and magnesium salts) and ammonium salts derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methyl-glucamine, D-methylglucamine, ethylglucamine, 1,6-hexadiamine, glucosamine, N-methylglycine, 2-amino-1,3-propanediol, tris(hydroxymethyl)aminomethane or 1-amino-2,3,4-butanetriol.

Solvates in the context of the invention refer to those forms of the inventive compounds which, in the solid or liquid state, exhibit adduct formation with solvent molecules. The solvent may be in a stoichiometric or else nonstoichiometric ratio. In the case of stoichiometric solvates, these are also referred to as hemi-, (semi-), mono-, sesqui-, di-, tri-, tetra-, penta-, etc. solvates. Hydrates are a specific form of the solvates in which the coordination is with water.

Moreover, the present invention also encompasses prodrugs of the compounds according to the invention. The term "prodrugs" encompasses compounds which, during their time of residence in the body, are converted to inventive compounds, for example by enzymatic or hydrolytic processes.

In the context of the present invention, the substituents, unless specified otherwise, are each defined as follows:

Alkyl represents straight- or branched-chain alkyl groups having 1-6 carbon atoms, for example methyl, ethyl, propyl, isopropyl, n-butyl, sec-butyl, isobutyl, tert-butyl, n-pentyl, isopentyl, neopentyl, hexyl, heptyl, octyl, nonyl and decyl.

Aryl represents a mono- to tricyclic aromatic, substituted or unsubstituted carbocyclic radical, for example phenyl, naphthyl, which may be mono- or polysubstituted by halogen (F, Cl, Br, I), OH, O-alkyl, $CO_2H$, $CO_2$-alkyl, $NH_2$, $NH(C_1$-$C_{10}$-alkyl), $N(C_1$-$C_{10}$-alkyl)$_2$, especially $N(CH_3)_2$, $NO_2$, $N_3$, CN, $C_1$-$C_{10}$-alkyl, $C_1$-$C_{10}$-perfluoroalkyl, $C_1$-$C_{10}$-acyl, $C_1$-$C_{10}$-acyloxy groups.

Heteroaryl is an aromatic mono- or bicyclic radical having generally 5 to 10 and preferably 5 to 6 ring atoms and up to 5, preferably up to 4, heteroatoms from the group of S, O and N, preferred examples being benzofuranyl, benzothiophenyl, quinolinyl, furyl, imidazolyl, indazolyl, indolyl, isoquinolinyl, oxazolyl, pyridazinyl, pyridyl, pyrimidyl, pyrrolyl, thiazolyl, thienyl, pyrazolyl, isoxazolyl, pyrazinyl, quinolyl or tetrazolyl.

Aralkyl represents aralkyl groups which may contain up to 14 carbon atoms, preferably 6-10 carbon atoms, in the ring and 1-8, preferably 1-4, carbon atoms in the alkyl chain. Useful aralkyl radicals include, for example, benzyl, phenylethyl, naphthylmethyl, naphthylethyl, furylmethyl, thienylethyl, pyridylpropyl. The rings may be mono- or polysubstituted by halogen, OH, O-alkyl, $CO_2H$, $CO_2$-alkyl, $NH_2$, $NH(C_1$-$C_{10}$-alkyl), $N(C_1$-$C_{10}$-alkyl)$_2$, $NO_2$, $N_3$, CN, $C_1$-$C_{20}$-alkyl, $C_1$-$C_{10}$-perfluoroalkyl, $C_1$-$C_{20}$-acyl or $C_1$-$C_{20}$-acyloxy groups.

When radicals in the inventive compounds are substituted, the radicals, unless specified otherwise, may be mono- or polysubstituted. In the context of the present invention, all radicals which occur more than once are each defined independently of one another. Substitution by one, two or three identical or different substituents is preferred. Very particular preference is given to substitution by one substituent.

Preference is given to compounds of the formula (II)

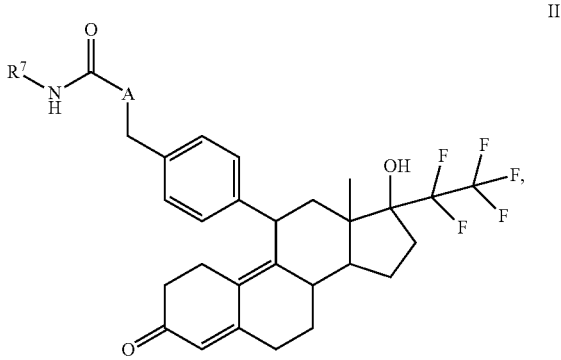

II in which
A is either —O— or —NH—,
$R^7$ is $C_1$-$C_4$-alkyl, allyl, phenyl optionally substituted in the para-position by the $C_1$-$C_4$-alkyl, —CN, $C_1$-$C_4$alkoxy, halogen, $C_1$-$C_4$alkanoyloxy, —$CO_2H$, —$CO_2C_{1-4}$-alkyl or piperidinyl groups,

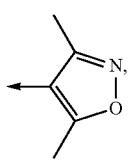

benzyl, —(CH$_2$)$_m$—COOR$^8$ where m=1, 2 or 3 and R$^8$=hydrogen or C$_1$-C$_4$-alkyl.

Preference is likewise given to compounds of the formula (III)

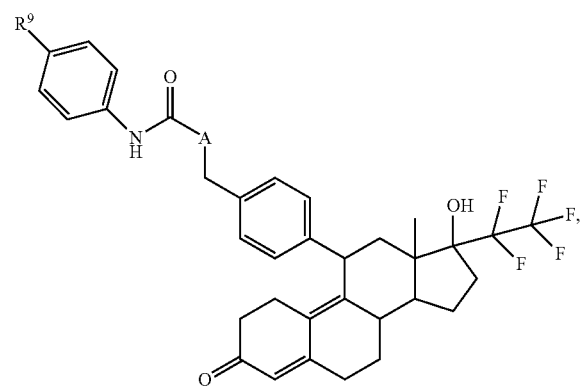

in which

A is either —O— or —NH— and

R$^9$ is hydrogen, C$_1$-C$_4$-alkyl, —CN, C$_1$-C$_4$alkoxy, halogen, C$_1$-C$_4$alkanoyloxy, —CO$_2$H, —CO$_2$C$_{1-4}$-alkyl or piperidinyl.

Preference is also given to the compounds of the formula (IV)

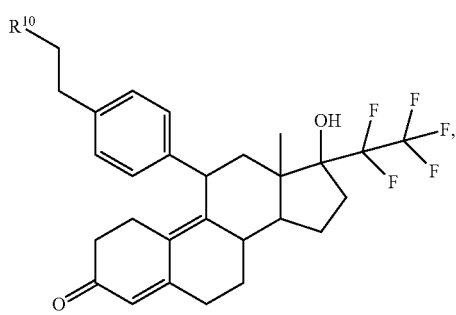

in which

R$^{10}$ is optionally methyl-substituted pyridinyl or thiazolyl, —CN, or —OH.

Preference is further given to compounds of the formula (V)

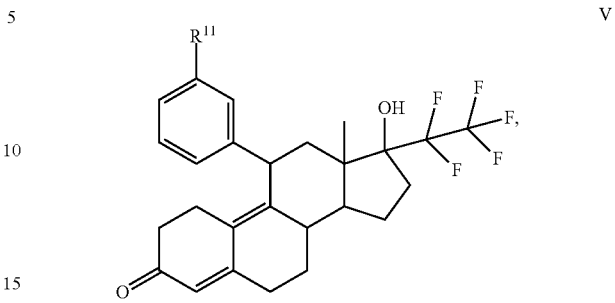

in which

R$^{11}$ is optionally hydroxyl-substituted C$_1$-C$_4$-alkyl, C$_1$-C$_4$-alkanoyloxy or optionally methyl-substituted cyclopropyl.

Further preferred compounds are:

(8S,11R,13S,14S,17S)-11-(4-cyclopropylphenyl)-17-hydroxy-13-methyl-17-pentafluoroethyl-1,2,6,7,8,11,12,13,14,15,16,17-dodecahydrocyclopenta[a]phenanthren-3-one (Example 1)

(8S,11R,13S,14S,17S)-17-hydroxy-13-methyl-17-pentafluoroethyl-11-[4-(2-pyridin-2-ylethyl)phenyl]-1,2,6,7,8,11,12,13,14,15,16,17-dodecahydrocyclopenta[a]phenanthren-3-one (Example 2)

(8S,11R,13S,14S,17S)-17-hydroxy-13-methyl-11-{4-[2-(2-methylthiazol-4-yl)ethyl]phenyl}-17-pentafluoroethyl-1,2,6,7,8,11,12,13,14,15,16,17-dodecahydrocyclopenta[a]phenanthren-3-one (Example 3)

(8S,11R,13S,14S,17S)-17-hydroxy-13-methyl-11-[4-(1-methylcyclopropyl)phenyl]-17-pentafluoroethyl-1,2,6,7,8,11,12,13,14,15,16,17-dodecahydrocyclopenta[a]phenanthren-3-one (Example 4)

(8S,11R,13S,14S,17S)-17-hydroxy-11-[4-(1-hydroxy-1-methylethyl)phenyl]-13-methyl-17-pentafluoroethyl-1,2,6,7,8,11,12,13,14,15,16,17-dodecahydrocyclopenta[a]phenanthren-3-one (Example 5)

(8S,11R,13S,14S,17S)-17-hydroxy-11-[4-((1R,2R or 1S,2S)-2-hydroxymethylcyclopropyl)phenyl]-13-methyl-17-pentafluoroethyl-1,2,6,7,8,11,12,13,14,15,16,17-dodecahydrocyclopenta[a]phenanthren-3-one (Example 6)

(8S,11R,13S,14S,17S)-17-hydroxy-13-methyl-17-pentafluoroethyl-11-[4-(2-pyridin-3-ylethyl)phenyl]-1,2,6,7,8,11,12,13,14,15,16,17-dodecahydrocyclopenta[a]phenanthren-3-one (Example 7)

(8S,11R,13S,14S,17S)-17-hydroxy-13-methyl-17-pentafluoroethyl-11-[4-(2-pyridin-4-ylethyl)phenyl]-1,2,6,7,8,11,12,13,14,15,16,17-dodecahydrocyclopenta[a]phenanthren-3-one (Example 8)

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propionitrile (Example 9)

(8S,11R,13S,14S,17S)-11-(3-acetylphenyl)-17-hydroxy-13-methyl-17-pentafluoroethyl-1,2,6,7,8,11,12,13,14,15,16,17-dodecahydrocyclopenta[a]phenanthren-3-one (Example 10)

(8S,11R,13S,14S,17S)-17-hydroxy-11-[3-((RS)-1-hydroxyethyl)phenyl]-13-methyl-17-pentafluoroethyl-1,2,6,7,8,11,12,13,14,15,16,17-dodecahydrocyclopenta[a]phenanthren-3-one (Example 11)

(8S,11R,13S,14S,17S)-11-(3-cyclopropylphenyl)-17-hydroxy-13-methyl-17-pentafluoroethyl-1,2,6,7,8,11,12,13,14,15,16,17-dodecahydrocyclopenta[a]phenanthren-3-one (Example 12)

(8S,11R,13S,14S,17S)-17-hydroxy-13-methyl-11-[3-(1-methylcyclopropyl)phenyl]-17-pentafluoroethyl-1,2,6,7,8,11,12,13,14,15,16,17-dodecahydrocyclopenta[a]phenanthren-3-one (Example 13)

(8S,11R,13S,14S,17S)-17-hydroxy-11-[3-(2-hydroxyethyl)phenyl]-13-methyl-17-pentafluoroethyl-1,2,6,7,8,11,12,13,14,15,16,17-dodecahydrocyclopenta[a]phenanthren-3-one (Example 14)

(8S,11R,13S,14S,17S)-17-hydroxy-11-[4-(2-hydroxy-1-hydroxymethyl-1-methylethyl)phenyl]-13-methyl-17-pentafluoroethyl-1,2,6,7,8,11,12,13,14,15,16,17-dodecahydrocyclopenta[a]phenanthren-3-one (Example 15)

(8S,11R,13S,14S,17S)-17-hydroxy-13-methyl-17-pentafluoroethyl-11-[4-(2,2,5-trimethyl-[1,3]dioxan-5-yl)phenyl]-1,2,6,7,8,11,12,13,14,15,16,17-dodecahydrocyclopenta[a]phenanthren-3-one (Example 15)

(8S,11R,13S,14S,17S)-17-hydroxy-11-[4-(2-hydroxy-1-hydroxymethylethyl)phenyl]-13-methyl-17-pentafluoroethyl-1,2,6,7,8,11,12,13,14,15,16,17-dodecahydrocyclopenta[a]phenanthren-3-one (Example 16)

1-allyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 18)

1-isopropyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 19)

1-tert-butyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 20)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}acetic acid ethyl ester (Example 21)

3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}propionic acid ethyl ester (Example 22)

1-benzyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 23)

1-phenyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 24)

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-p-tolylurea (Example 25)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}acetic acid (Example 26)

3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}propionic acid (Example 27)

(8S,11R,13S,14S,17S)-11-(4-azidomethylphenyl)-17-hydroxy-13-methyl-17-pentafluoroethyl-1,2,6,7,8,11,12,13,14,15,16,17-dodecahydrocyclopenta[a]phenanthren-3-one (Example 28)

(8S,11R,13S,14S,17S)-17-hydroxy-13-methyl-17-pentafluoroethyl-11-[4'-(1H-tetrazol-5-yl)biphenyl-4-yl]-1,2,6,7,8,11,12,13,14,15,16,17-dodecahydrocyclopenta[a]phenanthren-3-one (Example 29)

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzonitrile (Example 30)

(8S,11R,13S,14S,17S)-17-hydroxy-13-methyl-17-pentafluoroethyl-11-[4-(1H-tetrazol-5-yl)phenyl]-1,2,6,7,8,11,12,13,14,15,16,17-dodecahydrocyclopenta[a]phenanthren-3-one (Example 31)

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-(4-methoxyphenyl)urea (Example 32)

1-(4-fluorophenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 33)

1-(4-chlorophenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 34)

1-(4-tert-butylphenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 35)

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}benzoic acid ethyl ester (Example 36)

1-[4-(3,5-dimethylisoxazol-4-yl)phenyl]-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 37)

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}benzoic acid (Example 38)

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-(4-piperidin-1-ylphenyl)urea (Example 39)

(8S,11R,13S,14S,17S)-17-hydroxy-13-methyl-11-[4-(3-methyloxetan-3-yl)phenyl]-17-pentafluoroethyl-1,2,6,7,8,11,12,13,14,15,16,17-dodecahydrocyclopenta[a]phenanthren-3-one (Example 40)

ethylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 41)

isopropylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 42)

allylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 43)

tert-butylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 44)

(4-piperidin-1-ylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 45)

phenylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 46)

(4-methoxyphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 47)

(4-methylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 48)

(4-fluorophenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 49)

(4-chlorophenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 50)

(4-tert-butylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 51)

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]benzoic acid ethyl ester (Example 52)

[4-(3,5-dimethylisoxazol-4-yl)phenyl]carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 53)

N-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]nicotinamide (Example 54)

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]propionic acid (Example 55)

benzylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester (Example 56)

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]propionic acid ethyl ester (Example 57)

Some of the highly potent progesterone receptor antagonists specified here have a predicted oral bioavailability for humans of <50%, and they are therefore particularly suitable for local administrations requiring reduced systemic stability. Examples include the compounds specified in Examples 2-9, 15, 17, 23, 24, 40 and 41 (see Tables 1 and 2).

The specific radical definitions given in the particular combinations or preferred combinations of radicals are, irrespective of the particular combinations of radicals specified, also replaced as desired by radical definitions of other combinations.

Very particular preference is given to combinations of two or more of the above-mentioned preferred ranges.

It has been found that the inventive compounds or derivatives have good progesterone-antagonizing action. In several clinical studies, it has been found that treatment with progesterone receptor antagonists (mifepristone, asoprisnil, Proellex) can lead to significant shrinkage of fibroids of the uterus and to significant reduction of the symptoms associated with these fibroids of the uterus. In addition, it has been found in clinical studies that, during a treatment with the progesterone receptor antagonists mentioned, the symptoms caused by endometriosis (especially pain) can also be distinctly reduced.

The invention further relates to a process for preparing the inventive derivatives of the formula I. Such derivatives can be prepared as shown in Scheme 1, by converting an epoxide of the general formula VI in which X' is an oxygen atom, two alkoxy groups $OR^7$, a $C_2$-$C_{10}$-alkylene-α,ω-dioxy group which may be straight-chain or branched, $R^7$ is $C_1$-$C_4$-alkyl, by organometallic coupling reactions, preferably by copper-catalysed Grignard reactions, to a compound of the general formula I' in which $R^1$ and X' are each as defined above and $R^8$ is hydrogen, $R^9$ is a hydroxyl group, or $R^8$, $R^9$ together are a bond, and converting any functionalities present in $R^1$ and/or conducting further conversion reactions to give compounds of the general formula I' and optionally releasing the X group defined as oxygen and/or producing a double bond ($R^8$, $R^9$ together are a bond) by elimination of water ($R^8$=hydrogen, $R^9$=hydroxyl group) and optionally further functionalizing the carbonyl group (X=oxygen) (X=$NOR^6$ or an $NNHSO_2R^6$ group).

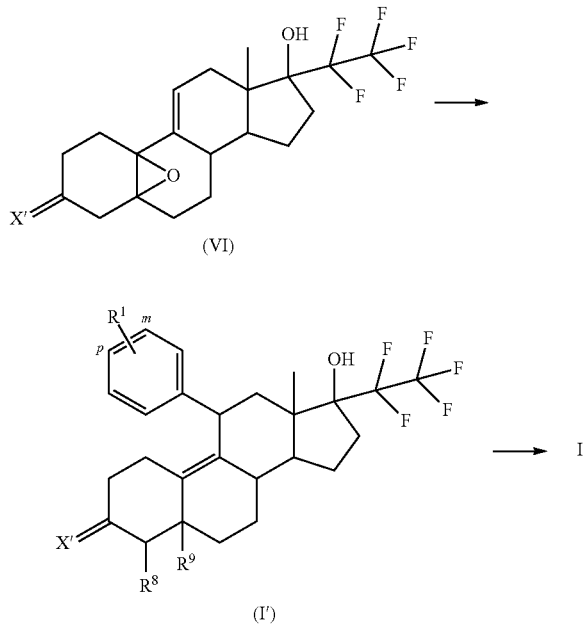

Scheme 1

If $R^8$ and $R^9$ together are a bond in the structure of the general formula I', these represent the three possible double bond isomers I'-A, I'-B and I'-C which can form in a wide variety of different ratios relative to one another during the reactions described.

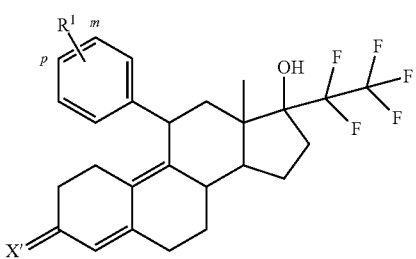

I'-A

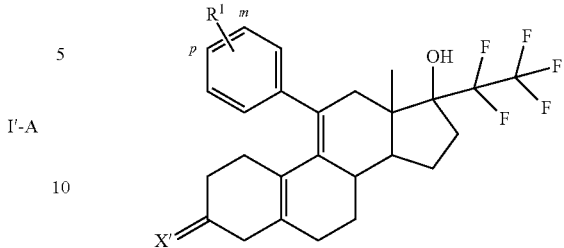

I'-C

Some possible reaction sequences to give compounds of the general formula I' proceeding from compounds of the general formula VI are shown in detail by way of example in Scheme 2.

Scheme 2

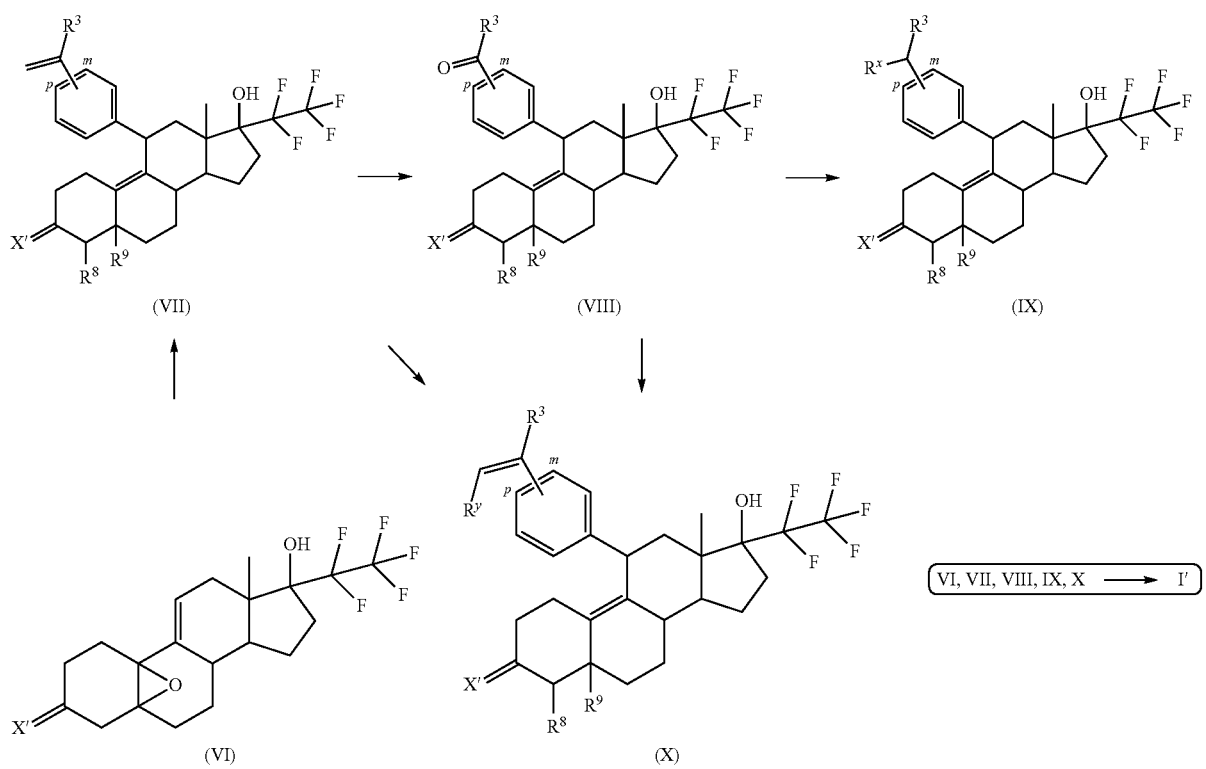

-continued

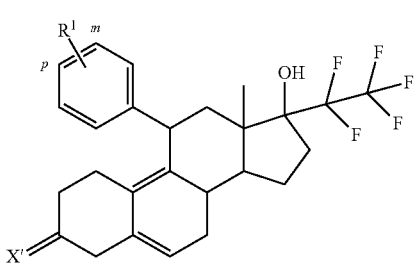

I'-B

The conversion of compounds of the general formula VI to compounds of the general formula VII or directly to compounds of the general formula I' in which X', $R^3$, $R^8$ and $R^9$ are each as defined above is effected by organometallic coupling reactions, preferably by copper-catalysed Grignard reactions, by the methods known to those skilled in the art. Typical details can be found in Examples 2d, 4b, 5c, 10a, 12b, 13b, 14b, 15a, 16a and 40a.

Compounds of the general formula VIII in which X', $R^3$, $R^8$ and $R^9$ are each as defined above can be prepared from compounds of the general formula VII by oxidative cleavage of the double bond by the methods known to those skilled in the art. Typical details can be found in Examples 2c and 5b.

Compounds of the general formula IX in which Rx is hydroxyl, azide, amine and X', $R^3$, $R^8$ and $R^9$ are each as defined above can be prepared from compounds of the general formula VIII by reduction of the carbonyl function, substitution by azide and reduction to the amine by the methods known to those skilled in the art. Typical details for such a reaction sequence can be found in Examples 17b, 17c and 17d.

Compounds of the general formula X in which $R^y$ aryl, heteroaryl, CN and X', $R^3$, $R^8$ and $R^9$ are each as defined above can be prepared from compounds of the general formula VIII in a Horner-Wittig or Wittig reaction by the methods known to those skilled in the art. Typical details can be found in Examples 2b, 3b, 7b, 8b and 9b.

Alternatively, compounds of the general formula X can be prepared from compounds of the general formula VII in a metathesis reaction using transition metal catalysts, preferably based on ruthenium. Typical details can be found in Example 6b.

Compounds of the general formula X can be converted to compounds of the general formula I', for example, by hydrogenation, cyclopropanation or epoxidation of the double bond. Typical details can be found in Examples 2a, 3a, 6a, 7a, 8a and 9a.

Compounds of the general formula VIII can be converted to compounds of the general formula I', for example, by nitrile formation, alkylation or reduction. Typical details can be found in Examples 5, 5a and 30a.

Compounds of the general formula VII can be converted to compounds of the general formula I', for example, by hydrogenation, cyclopropanation, epoxidation or hydroboration of the double bond. Typical details can be found in Examples 1a, 4a, 12a, 13a and 14a.

Compounds of the general formula IX in which $R^x$ is a hydroxyl group or amino group can be further converted to carbamates, amides or ureas by the methods known to those skilled in the art to give compounds of the general formula I'. Typical details can be found in Examples 17a-25a, 32a-39a, 41a-53a, 54a, 55b, 56 and 57.

If not already accomplished by the reactions described, any ketals present in the compounds of the general formulae I', VII, VIII, IX or X are cleaved to give X' and/or, if $R^8$ is defined as hydrogen and $R^9$ is defined as hydroxyl, water is eliminated. Typical details can be found in Examples 1-10 and 12-57.

Functional groups in the compounds of the general formulae I, I', VII, VIII, IX or X can be derived further by the methods known to those skilled in the art. Examples include the esterification of carboxyl groups, the hydrolysis of carboxylic esters or carboxamides, the formation of nitriles from carboxylic acids or aldehydes, the preparation of tetrazoles from nitriles or carboxylic acid. Some typical details can be found in Examples 11, 26a, 27a, 29a, 31a and 55a.

To the extent that the preparation of the starting compounds is not described here, they are known to the person skilled in the art or are preparable analogously to known compounds or processes described here. The isomer mixtures can be separated into the individual compounds by customary methods, for example crystallization, chromatography or salt formation.

The salts are prepared in a customary manner, by admixing a solution of the compound of the general chemical formula I with the equivalent amount or an excess of a base or acid which may be in solution, optionally removing the precipitate or working up the solution in a customary manner.

The resulting compounds of the formula (I) are optionally reacted with the appropriate (i) solvents and/or (ii) bases or acids to give the solvates, salts and/or solvates of the salts thereof.

The radical definitions given above in general terms or specified within areas of preference apply both to the end products of the formula I and correspondingly to the starting materials or intermediates required for the preparation of each.

The inventive compounds exhibit an unforeseeable, valuable pharmacological, pharmacokinetic and pharmacodynamic profile of action.

They are therefore suitable for use as medicaments for treatment and/or prophylaxis of disorders in humans and animals.

The pharmaceutical efficacy of the inventive compounds can be explained by the action thereof as a progesterone receptor antagonist, i.e. the antagonizing action thereof on the progesterone receptor.

The present invention further provides for the use of the inventive compounds for treatment and/or prophylaxis of disorders based on hormone-dependent hyperproliferative processes, preferably of gynaecological disorders, especially of fibroids of the uterus, endometriosis or hormone-dependent breast cancers.

The present invention further provides for the use of the inventive compounds for treatment and/or prophylaxis of disorders, especially of the aforementioned disorders.

The present invention further provides the inventive compounds for use in a process for treatment and/or prophylaxis of fibroids of the uterus, of endometriosis and of hormone-dependent breast cancers.

The present invention further provides for the use of the inventive compounds for production of a medicament for treatment and/or prophylaxis of disorders, especially of the aforementioned disorders.

The present invention further provides a method for treatment and/or prophylaxis of disorders, especially of the aforementioned disorders, using 0.1-100 mg of the inventive compounds per day and patient in the treatment of fibroids of the uterus or of endometriosis, and for the contraceptive use, or 0.1-500 mg of the inventive compounds per day and patient in the event of tumours (e.g. menginioma or hormone-dependent tumours, for example breast cancer) and in emergency contraception.

The present invention further provides medicaments comprising at least one inventive compound and at least one or more than one further active ingredient, especially for treatment and/or prophylaxis of the aforementioned disorders.

For treatment of tumour disorders, it is possible, for example, to either simultaneously or sequentially administer the following active ingredients/active ingredient classes: SERMs, SERDs, antioestrogens, aromatase inhibitors, kinase inhibitors, angiogenesis inhibitors and/or cytostatics.

For treatment of fibroids of the uterus or of endometriosis, the inventive compounds can be combined simultaneously or sequentially with gestagens or combinations of oestrogens and gestagens.

WO 96/15794 (Spicer et al., Balance Pharm. Inc.), WO 96/03130 (Stockemann et al., Schering AG) and PCT/EP2009/003249 (Möller et al., Bayer Schering Pharma AG) disclose progesterone receptor antagonist/gestagen regimens. Fibroids of the uterus and endometriosis are very suitably treated by optionally repeating regimens in which the progesterone receptor antagonist is administered over a period of two to four months, followed by the administration of the gestagen over a period of one to four weeks. A particularly suitable administration is the optionally repeating 84-day administration of the progesterone receptor antagonist, followed by the 14-day administration of the gestagen.

For treatment of complaints associated with the menopause, one option is a simultaneous or sequential administration of the inventive compounds, for example, with SERMs, SERDs and oestrogens.

SERMs (Selective Estrogen Receptor Modulators) are, in accordance with the invention, those compounds which are tissue-selective and have either antioestrogenic or oestrogenic action, for example inhibit the action of oestrogen in the uterus, but have a neutral or oestrogen-like action in the bone. Examples are clomifene, raloxifene, tamoxifen, torimifene, bazedoxifene, lasofoxifene and ormeloxifene.

Selective oestrogen receptor destabilizers (SERDs) are medicaments which antagonise the oestrogen receptor ("pure antioestrogens" without an oestrogenic active component) and lead to degradation of the receptor (for example fulvestrant, ZK-703 and ZK-253 [Hoffmann J et al., J Natl Cancer Inst 2004, 96:210-218], and compounds described in WO 98/007740, WO 99/33855 and WO 03/045972.

Antioestrogens are compounds which antagonise the oestrogen receptor, for example fulvestrant.

Aromatase inhibitors inhibit the enzyme aromatase and hence the aromatisation of androgens in oestrogens. These include anastrozole, letrozole, exemestane, vorozole, formestane and fadrozole.

Kinase inhibitors inhibit enzymes which transfer a phosphate residue from ATP to other substrates, and especially to hydroxyl groups therein, for example sorafenib (Nexavar) or imatinib (Gleevec).

Angiogenesis inhibitors, e.g. avastatin, reduce or block vessel supply and hence the profusion of a tumour.

Cytostatics, e.g. cis-platin, taxol, Taxotere, sagopilone, ixabepilone, are natural or synthetic substances which inhibit cell growth and cell division.

Gestagens in the context of the present invention are understood to mean either natural progesterone itself or synthetic derivatives which, like progesterone itself, bind to the progesterone receptor and inhibit ovulation in doses above the ovulation-inhibiting dose. Examples of synthetic derivatives include drospirenone, gestodene, levonorgestrel, cyproterone acetate, desogestrel and 3-ketodesogestrel, norethisterone, norethisterone acetate and dienogest.

Combinations of gestagens and oestrogens are active ingredient combinations present in the oral contraceptive known per se, for example Yasmin, Femovan, Triquilar, Marvelon, YAZ etc.

The inventive compounds can act systemically and/or locally. For this purpose, they can be administered in a suitable manner, for example by an oral, intrauterine, intravaginal, parenteral, pulmonary, nasal, sublingual, lingual, buccal, rectal, dermal, transdermal, conjunctival or otic route, or as an implant or stent.

"Intrauterine" means especially administration by means of an IUS (intrauterine system) or IUD (intrauterine device). One method of intravaginal administration is by means of an IVR/VRS (intravaginal ring/vaginal ring system).

Intrauterine or intravaginal administration forms (cf., for example, WO 01/47490, especially page 1 line 10 to page 5 line 13 and page 7 line 19 to page 58 line 6, or for vaginal rings: WO 06/010097, especially page 10 line 22 to page 14 line 28) may comprise the inventive compounds and nonsilicone and/or silicone polymers, especially also siloxane-based elastomers (cf. WO 01/47490, especially page 7 line 19-page 15 line 15).

For these administration routes, the inventive compounds can be administered in suitable administration forms.

Suitable administration forms for oral administration are those which release the inventive compounds in a rapid and/or modified manner, work according to the prior art and contain the inventive compounds in crystalline and/or amorphous and/or dissolved form, for example tablets (uncoated or coated tablets, for example with enteric or retarded-dissolution or insoluble coatings which control the release of the inventive compound), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilisates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and taste and/or odour correctors.

The present invention further provides medicaments which comprise at least one inventive compound, typically together with one or more inert nontoxic pharmaceutically suitable excipients, and for the use thereof for the aforementioned purposes.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are percentages by weight unless stated otherwise; parts are parts by weight. Solvent ratios, dilution ratios and concentration figures for liquid/liquid solutions are each based on volume.

The examples which follow serve to illustrate the invention without restricting it in any way.

EXAMPLE 1

(8S,11R,13S,14S,17S)-11-(4-cyclopropylphenyl)-17-hydroxy-13-methyl-17-pentafluoroethyl-1,2,6,7,8,11,12,13,14,15,16,17-dodecahydrocyclopenta[a]phenanthren-3-one

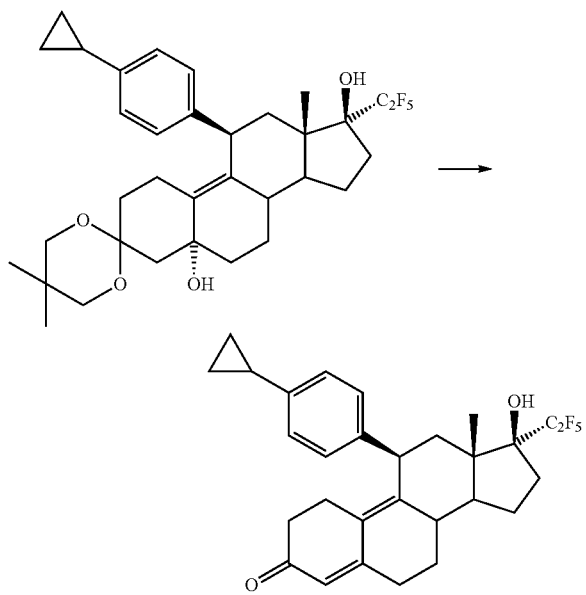

The solution of 266 mg (0.44 mmol) of the compound prepared according to Example 1a in 14 ml of acetone was admixed with 0.65 ml of 4N hydrochloric acid and the mixture was stirred at 23° C. for 20 minutes. The mixture was poured into a saturated sodium hydrogencarbonate solution and extracted repeatedly with dichloromethane, the combined organic extracts were dried over sodium sulphate and the residue obtained after filtration and removal of solvent was purified by chromatography. 173 mg (78%) of the title compound were isolated as a colourless foam.

$^1$H NMR (CDCl$_3$): δ=0.61 (3H), 0.66 (2H), 0.94 (2H), 1.41-1.55 (2H), 1.74-1.89 (4H), 2.03 (1H), 2.05 (1H), 2.24-2.63 (9H), 2.73 (1H), 4.41 (1H), 5.77 (1H), 6.97 (2H), 7.04 (2H) ppm.

EXAMPLE 1a (5R,8S,11R,13S,14S,17S)-11-(4-cyclopropylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

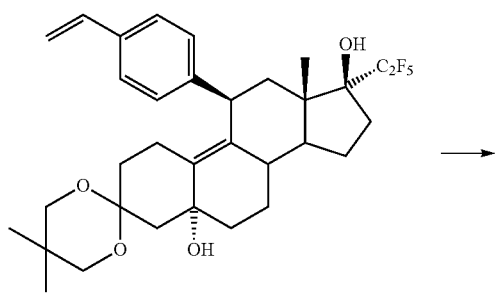

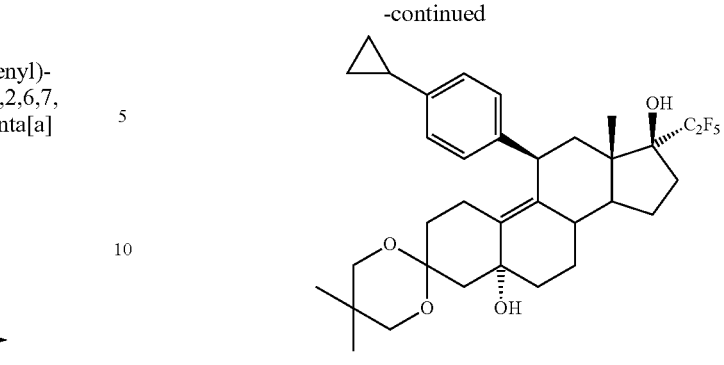

The solution of 300 mg (0.5 mmol) of the compound prepared according to Example 2d in 30 ml of diethyl ether was admixed at 3° C. with 27 ml of an ethereal diazomethane solution and, in portions over the course of 5 minutes, with a total of 131 mg of palladium(II) acetate. After stirring for 15 minutes, the mixture was purified by chromatography. 266 mg (87%) of the title compound were isolated as a colourless foam.

EXAMPLE 2

(8S,11R,13S,14S,17S)-17-hydroxy-13-methyl-17-pentafluoroethyl-11-[4-(2-pyridin-2-ylethyl)phenyl]-1,2,6,7,8,11,12,13,14,15,16,17-dodecahydrocyclopenta[a]phenanthren-3-one

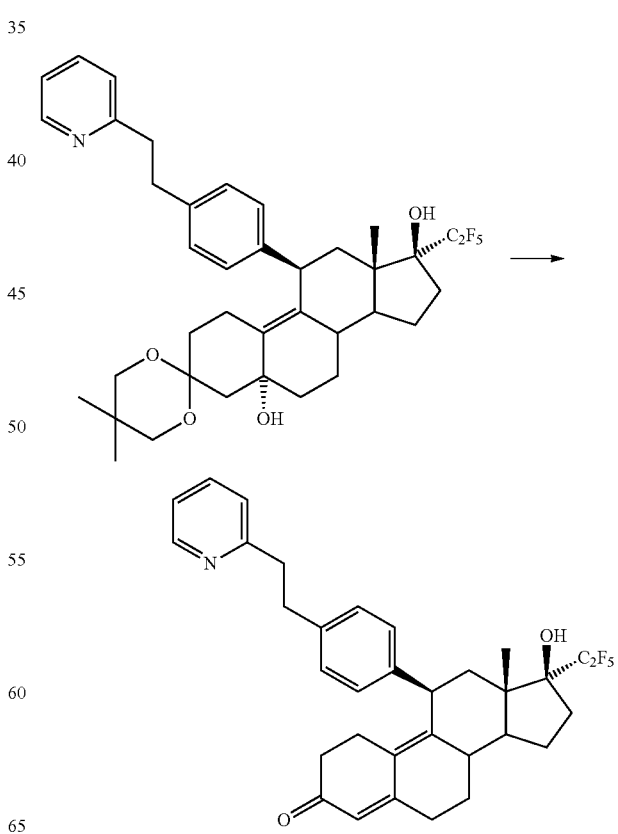

In analogy to Example 1, 60 mg (89 μmol) of the compound prepared according to Example 2a were converted and, after workup and purification, 36.6 mg (72%) of the title compound were isolated as a colourless foam.

$^1$H NMR (CDCl$_3$): δ=0.63 (3H), 1.44-1.61 (2H), 1.77-1.92 (3H), 2.10 (1H), 2.24-2.69 (10H), 2.78 (1H). 2.99-3.16 (4H), 4.46 (1H), 5.82 (1H), 7.03-7.18 (6H), 7.58 (1H), 8.58 (1H) ppm.

EXAMPLE 2a (5R,8S,11R,13S,14S,17S)-5',5',13-trimethyl-17-(pentafluoroethyl)-11-{4-[(E)-2-(pyridin-4-yl)ethyl]phenyl}-1,2,3,4,6,7,8,11,12,13,14,15,16,17-tetradecahydrospiro[cyclopenta[a]phenanthrene-3,2'-[1,3]dioxane]-5,17-diol

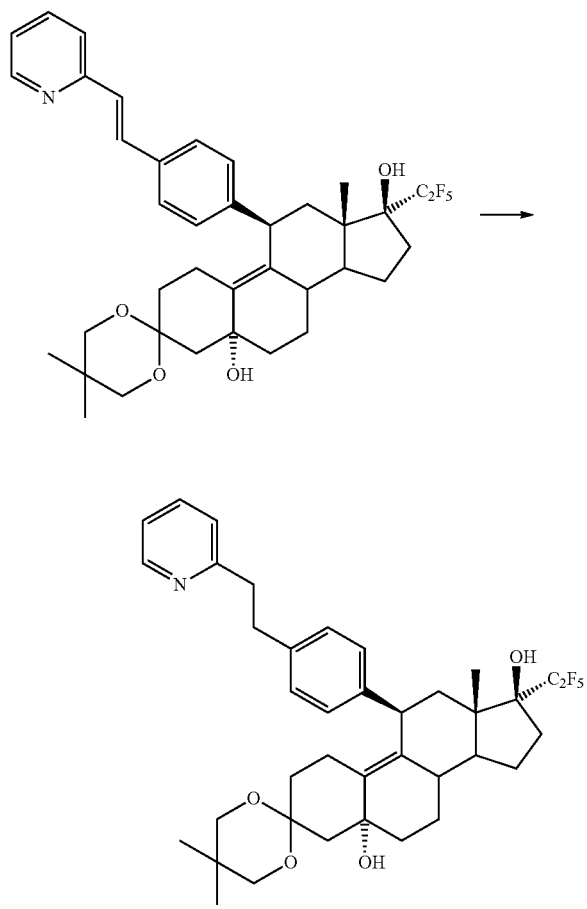

The solution of 70 mg (0.1 mmol) of the compounds prepared according to Example 2b in 1 ml of ethanol was admixed with 5 mg of palladium on carbon (10%) and hydrogenated under an atmosphere of hydrogen. After filtration and removal of solvent, 70 mg (100%) of the title compound were isolated, which were converted further without purification.

EXAMPLE 2b (5R,8S,11R,13S,14S,17S)-5',5',13-trimethyl-17-(pentafluoroethyl)-11-{4-[(E)-2-(pyridin-2-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

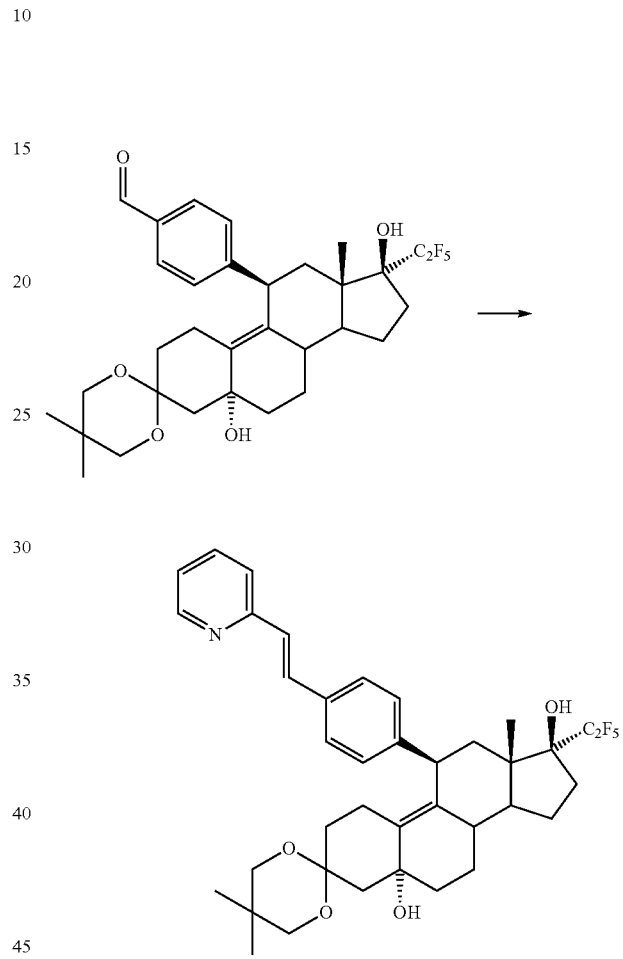

The solution of 345 mg of diethyl pyridin-2-ylmethylphosphonate in 10 ml of tetrahydrofuran was admixed at −10° C. with 0.6 mg of a 1.6 molar solution of n-butyllithium in hexane, and the mixture was stirred at 23° C. for 1.5 hours. Subsequently, the mixture was cooled to −70° C., the solution of 300 mg (0.5 mmol) of the compound prepared according to Example 2c in 5 ml of tetrahydrofuran were added dropwise, the cooling bath was removed and the mixture was left to react for 1.5 hours. The mixture was poured into a saturated ammonium chloride solution and extracted repeatedly with ethyl acetate, and the combined organic extracts were dried over sodium sulphate. The residue obtained after filtration and solvent removal was purified by chromatography. 302 mg (89%) of the title compound were isolated as a colourless foam.

EXAMPLE 2c 4-((5R,8S,11R,13S,14S,17S)-5,17-dihydroxy-5',5', 13-trimethyl-17-pentafluoroethyl-2,3,4,5,6,7,8,11, 12,13,14,15,16,17-tetradecahydro-1H-spiro[cyclopenta[a]phenanthrene-3,2'-[1,3]dioxan]-11-yl)-benzaldehyde

EXAMPLE 2d (5R,8S,11R,13S,14S,17S)-11-(4-ethenylphenyl)-5', 5',13-trimethyl-17-(pentafluoroethyl)-1,2,3,4,6,7,8, 11,12,13,14,15,16,17-tetradecahydrospiro[cyclopenta[a]phenanthrene-3,2'-[1,3]dioxane]-5,17-diol

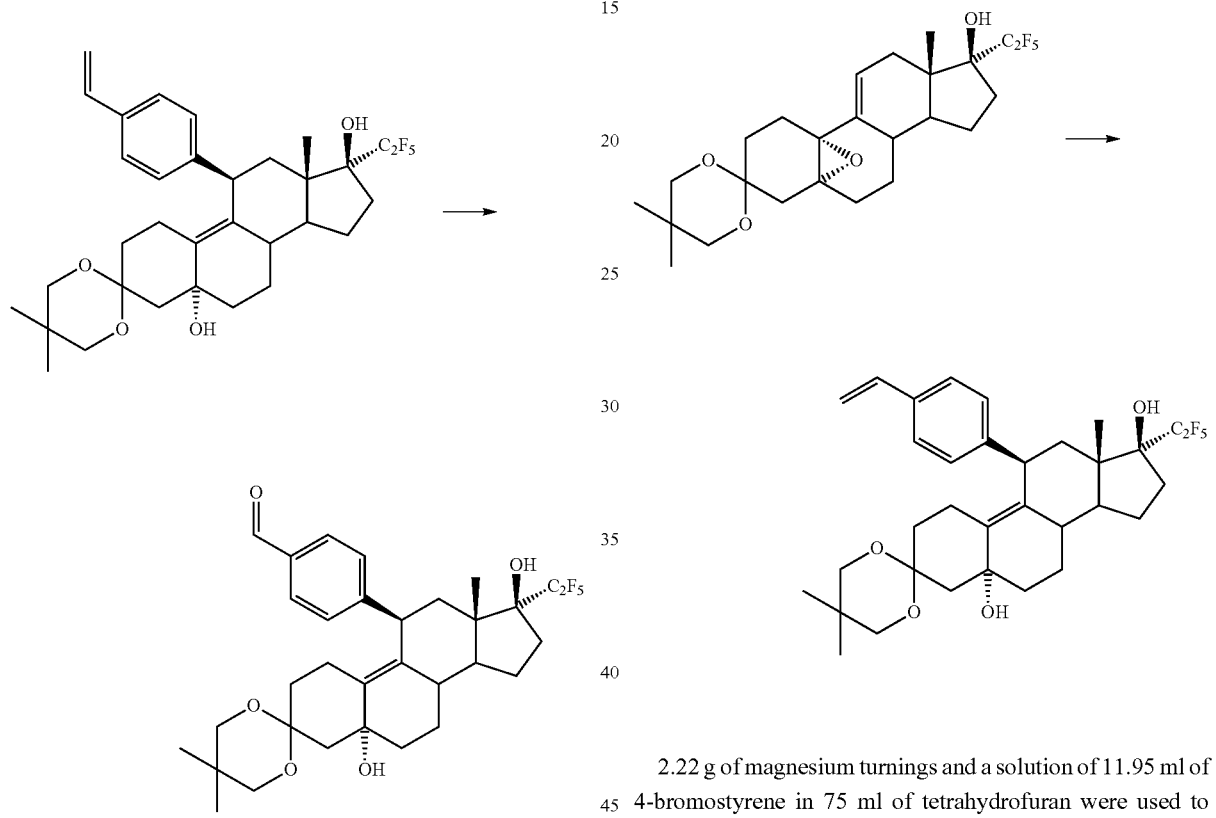

The solution of 3.99 g (6.69 mmol) of the compound prepared according to Example 2d in 200 ml of tetrahydrofuran was admixed with 25 ml of water, 1 ml of triethylamine, 3.2 ml of a saturated sodium hydrogencarbonate solution, 3.2 g of sodium periodate, 2.7 ml of a 40 mmolar solution of osmium tetroxide in tert-butanol, and the mixture was stirred at 23° C. After 16 hours and 40 hours, the addition of oxidizing agents was repeated and, after a further 24 hours, solid constituents were filtered off. They were rinsed with ethyl acetate and the combined organic phases were washed with semisaturated sodium thiosulphate solution and saturated sodium chloride solution. The residue obtained after filtration and removal of solvent was purified by crystallization from diisopropyl ether. 3.56 g (89%) of the title compound were isolated as a colourless foam.

2.22 g of magnesium turnings and a solution of 11.95 ml of 4-bromostyrene in 75 ml of tetrahydrofuran were used to prepare the Grignard reagent, with gentle heating to 30-50° C. and optionally with addition of an iodine crystal. The mixture was cooled to 5° C., 117 mg of copper(I) chloride were added, and the solution of 15 g (30.5 mmol) of (5R,8S,10R,13S,14S, 17S)-17-(pentafluoroethyl)-5,10-epoxy-5',5',13-trimethyl-1, 2,3,4,6,7,8,12,13,14,15,16,17-tridecahydrospiro[cyclopenta [a]phenanthrene-3,2'-[1,3]dioxane]-17-ol, which was prepared by the process described in DE 102006054535, in 150 ml was added dropwise. The mixture was stirred at 23° C. for another 1 hour, diluted with ethyl acetate and poured into a saturated ammonium chloride solution. The aqueous phase was extracted repeatedly with ethyl acetate, and the combined organic extracts were washed with saturated sodium chloride solution and dried over sodium sulphate. The solid obtained after filtration and removal of solvent was recrystallized from hexane, and 16.6 g (91%) of the title compound were isolated as a colourless solid.

EXAMPLE 3

(8S,11R,13S,14S,17S)-17-hydroxy-13-methyl-11-{4-[2-(2-methylthiazol-4-yl)ethyl]phenyl}-17-pentafluoroethyl-1,2,6,7,8,11,12,13,14,15,16,17-dodecahydrocyclopenta[a]phenanthren-3-one

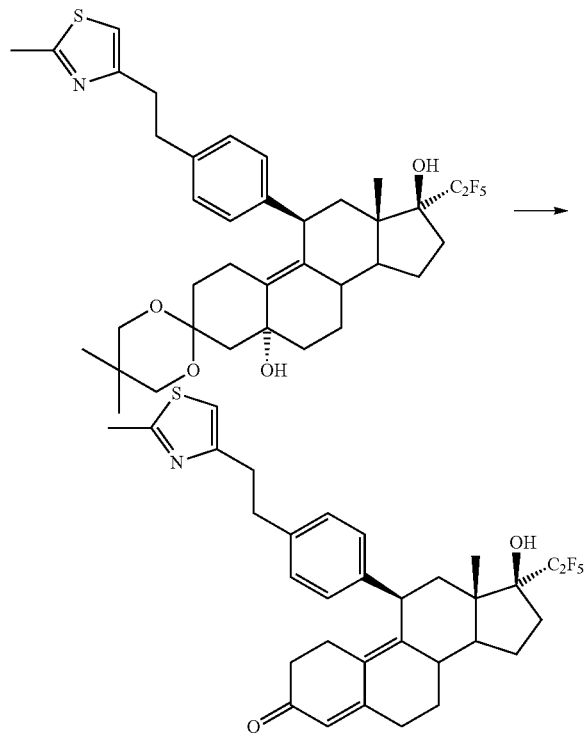

In analogy to Example 1, 7 mg (10 μmol) of the compound prepared according to Example 3a were converted and, after workup and purification, 5 mg (84%) of the title compound were isolated as a colourless foam.

¹H NMR (CDCl₃): δ=0.59 (3H), 1.41-1.54 (2H), 1.74-1.85 (3H), 2.01-2.11 (2H), 2.24-2.63 (9H), 2.70 (3H), 2.73 (1H), 2.93-3.04 (4H), 4.42 (1H), 5.78 (1H), 6.61 (1H), 7.06 (2H), 7.09 (2H) ppm.

EXAMPLE 3a (5R,8S,11R,13S,14S,17S)-5',5',13-trimethyl-11-{4-[2-(2-methyl-1,3-thiazol-4-yl)ethyl]phenyl}-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

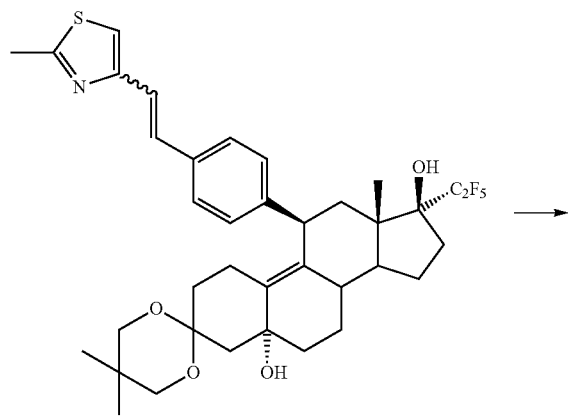

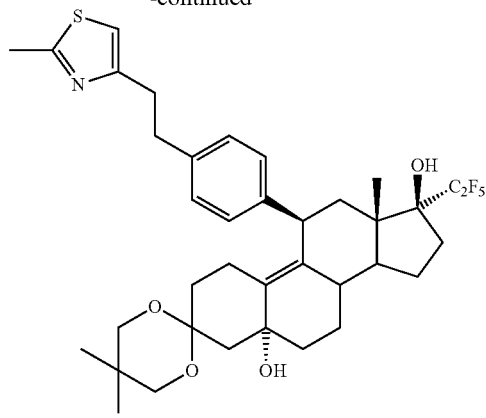

In analogy to Example 2a, 48 mg (69 μmol) of the compound prepared according to Example 3b were converted and, after workup and purification, 8 mg (19%) of the title compound were isolated as a colourless foam.

EXAMPLE 3b (5R,8S,11R,13S,14S,17S)-5',5',13-trimethyl-11-{4-[(E/Z)-2-(2-methyl-1,3-thiazol-4-yl)ethenyl]phenyl}-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

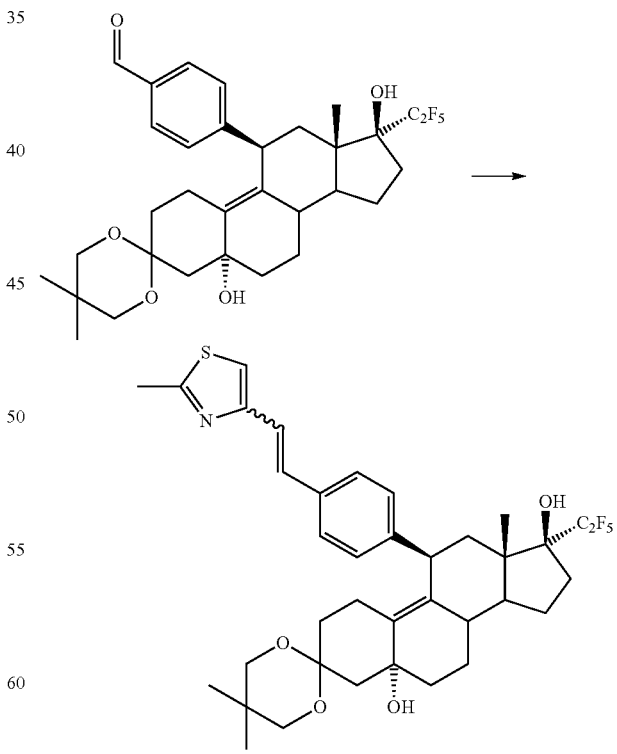

In analogy to Example 2b, 500 mg (0.84 mmol) of the compound prepared according to Example 2c were converted using diethyl(2-methylthiazol-4-ylmethyl)phosphonate and, after workup and purification, 479 mg (83%) of a mixture of the two title compounds were isolated as a colourless foam.

EXAMPLE 4

(8S,11R,13S,14S,17S)-17-hydroxy-13-methyl-11-[4-(1-methylcyclopropyl)phenyl]-17-pentafluoroethyl-1,2,6,7,8,11,12,13,14,15,16,17-dodecahydrocyclopenta[a]phenanthren-3-one

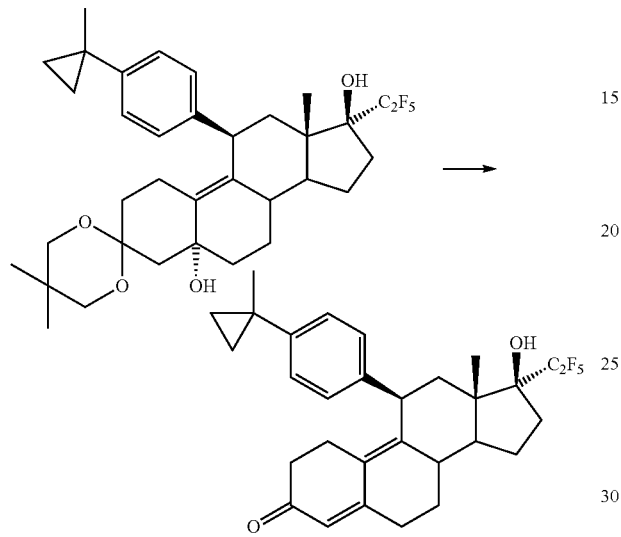

In analogy to Example 1, 160 mg (0.26 mmol) of the compound prepared according to Example 4a were converted and, after workup and purification, 70.6 mg (53%) of the title compound were isolated as a colourless foam.

$^1$H NMR (CDCl$_3$): δ=0.60 (3H), 0.70-0.77 (2H), 0.79-0.87 (2H), 1.38 (3H), 1.40-1.55 (2H), 1.72-1.86 (3H), 2.01-2.11 (2H), 2.24-2.63 (9H), 2.73 (1H), 4.41 (1H), 5.77 (1H), 7.05 (2H), 7.12 (2H) ppm.

EXAMPLE 4a (5R,8S,11R,13S,14S,17S)-5',5',13-trimethyl-11-[4-(1-methylcyclopropyl)phenyl]-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

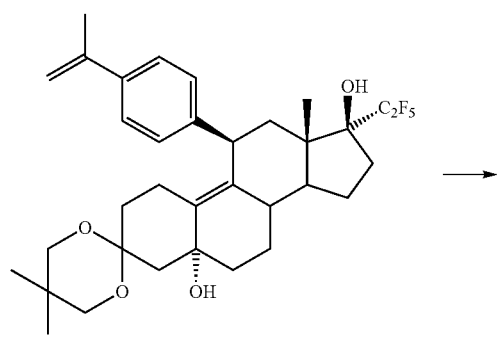

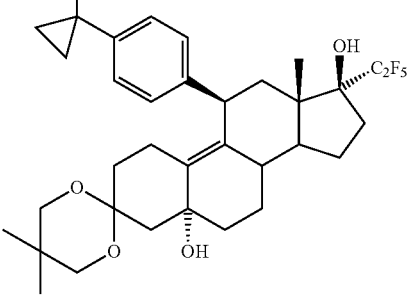

In analogy to Example 1a, 200 mg (0.33 mmol) of the compound prepared according to Example 4b were converted and, after workup and purification, 165 mg (81%) of the title compound were isolated as a colourless foam.

EXAMPLE 4b (5R,8S,11R,13S,14S,17S)-5',5',13-trimethyl-17-(pentafluoroethyl)-11-[4-(prop-1-en-2-yl)phenyl]-1,2,3,4,6,7,8,11,12,13,14,15,16,17-tetradecahydrospiro[cyclopenta[a]phenanthrene-3,2'-[1,3]dioxane]-5,17-diol

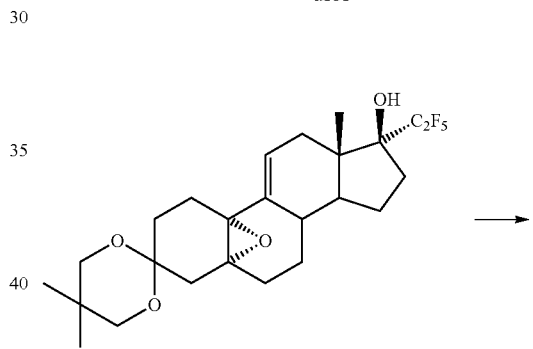

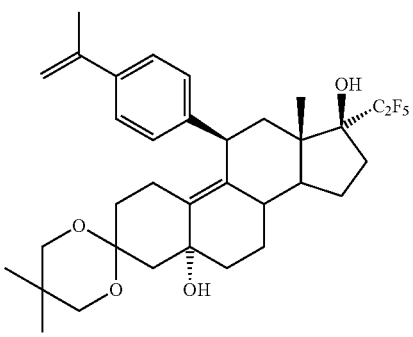

In analogy to Example 2d, 5 g (10.2 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were reacted with the Grignard reagent prepared from 10 g of 1-bromo-4-isopropenylbenzene and, after workup and purification, 4.01 g (65%) of the title compound were isolated as a colourless foam.

EXAMPLE 5

(8S,11R,13S,14S,17S)-17-hydroxy-11-[4-(1-hydroxy-1-methylethyl)phenyl]-13-methyl-17-pentafluoroethyl-1,2,6,7,8,11,12,13,14,15,16,17-dodecahydrocyclopenta[a]phenanthren-3-one

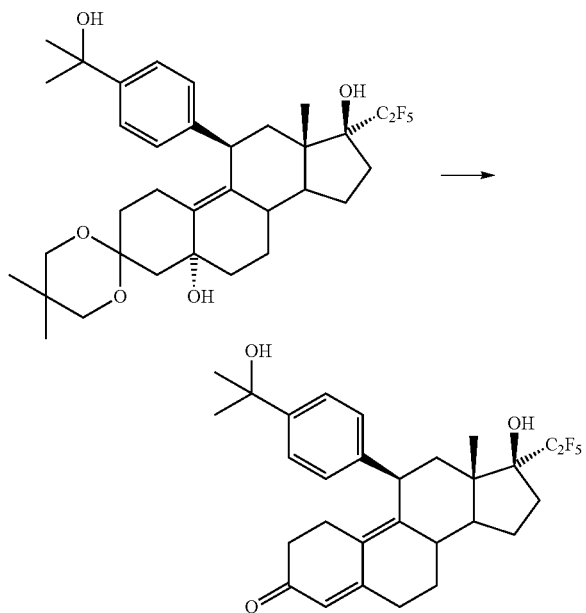

In analogy to Example 1, 20 mg (32 µmol) of the compound prepared according to Example 5a were converted and, after workup and purification, 7.6 mg (46%) of the title compound were isolated as a colourless foam.

$^1$H NMR (CD$_2$Cl$_2$): δ=0.59 (3H), 1.40-1.62 (2H), 1.52 (6H), 1.71-1.87 (3H), 1.98-2.11 (2H), 2.19-2.63 (10H), 2.73 (1H), 4.45 (1H), 5.71 (1H), 7.16 (2H), 7.38 (2H) ppm.

EXAMPLE 5a (5R,8S,11R,13S,14S,17S)-11-[4-(2-hydroxypropan-2-yl)phenyl]-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

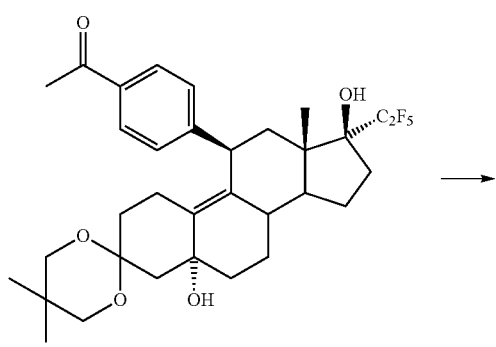

-continued

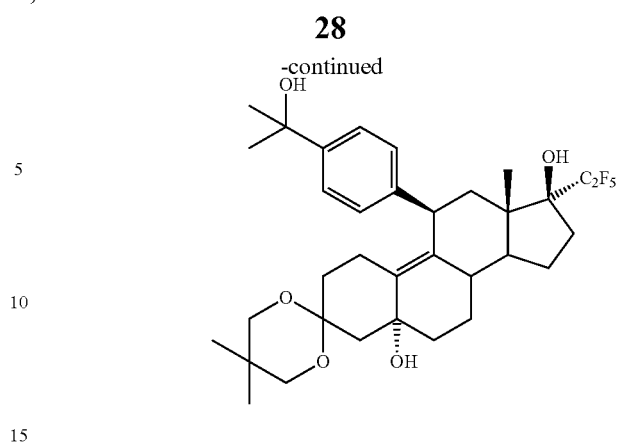

The solution of 23 mg (38 µmol) of the compound prepared according to Example 5b in 1.6 ml of tetrahydrofuran was admixed at 0° C. with 200 µl of a 1.6 molar solution of methyllithium in diethyl ether and stirred for 45 minutes. The mixture was poured into a saturated ammonium chloride solution and extracted repeatedly with ethyl acetate, and the combined organic extracts were washed with saturated sodium chloride solution and dried over sodium sulphate. After filtration and removal of solvent, 23 mg (97%) of the title compound were isolated as a colourless foam, which was converted further without purification.

EXAMPLE 5b

1-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl}ethanone

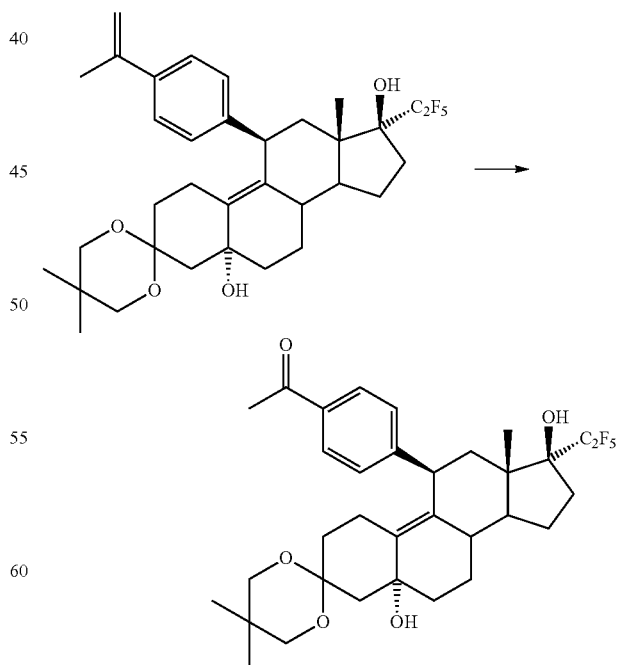

In analogy to Example 2c, 5.5 g (9.0 mmol) of the compound prepared according to Example 5c were converted and, after workup and purification, 4.78 g (87%) of the title compound were isolated as a colourless solid.

EXAMPLE 5c (5R,8S,11R,13S,14S,17S)-5',5',13-trimethyl-17-(pentafluoroethyl)-11-[4-(prop-1-en-2-yl)phenyl]-1,2,3,4,6,7,8,11,12,13,14,15,16,17-tetradecahydrospiro[cyclopenta[a]phenanthrene-3,2'-[1,3]dioxane]-5,17-diol

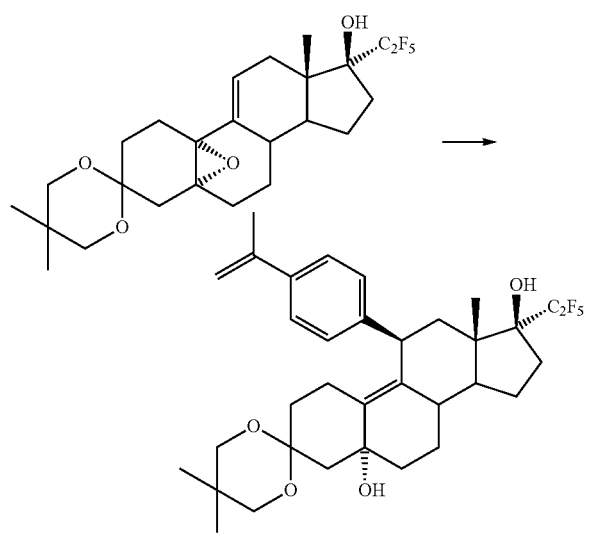

In analogy to Example 2d, 5 g (10.2 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were reacted with the Grignard reagent prepared from 10 g of 1-bromo-4-isopropenylbenzene and, after workup and purification, 4.01 g (65%) of the title compound were isolated as a colourless foam.

EXAMPLE 6

(8S,11R,13S,14S,17S)-17-hydroxy-11-[4-((1R,2R)-2-hydroxymethylcyclopropyl)phenyl]-13-methyl-17-pentafluoroethyl-1,2,6,7,8,11,12,13,14,15,16,17-dodecahydrocyclopenta[a]phenanthren-3-one (A) and (8S,11R,13S,14S,17S)-17-hydroxy-11-[4-((1S,2S)-2-hydroxymethylcyclopropyl)phenyl]-13-methyl-17-pentafluoroethyl-1,2,6,7,8,11,12,13,14,15,16,17-dodecahydrocyclopenta[a]phenanthren-3-one (B)

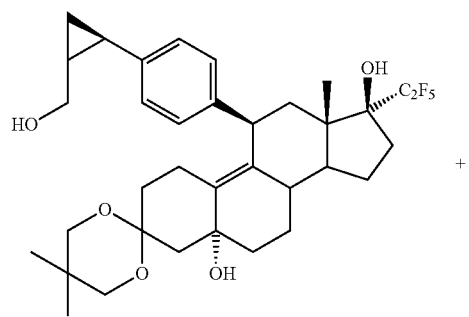

+

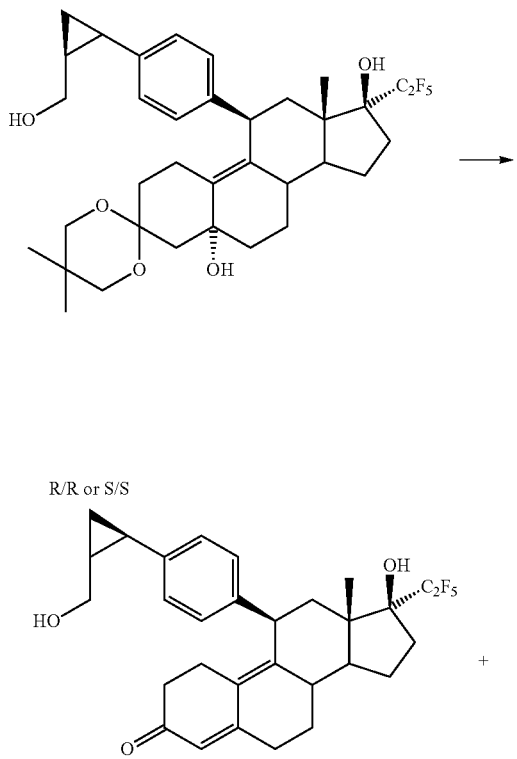

R/R or S/S

S/S or R/R

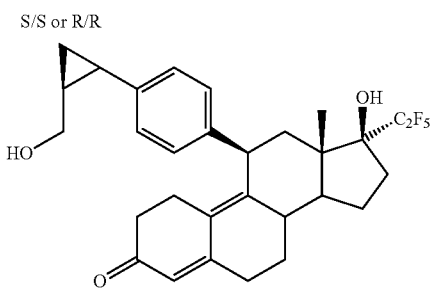

In analogy to Example 1, 22 mg (35 μmol) of a mixture of the compounds prepared according to Example 6a were reacted and, after workup and purification, 3.5 mg (19%) of title compound A or B and 7.9 mg (42%) of title compound B or A were isolated, each as a colourless foam.

$^1$H NMR (CDCl$_3$) of A or B: δ=0.60 (3H), 0.96 (2H), 1.39-1.53 (3H), 1.73-1.89 (4H), 2.03 (1H), 2.05 (1H), 2.16 (1H), 2.23-2.63 (9H), 2.72 (1H), 4.05 (2H), 4.41 (1H), 5.77 (1H), 6.97 (2H), 7.06 (2H) ppm.

$^1$H NMR (CDCl$_3$) of B or A: δ=0.60 (3H), 0.93 (2H), 1.37-1.55 (4H), 1.72-1.86 (4H), 2.05 (1H), 2.11 (1H), 2.23-2.63 (9H), 2.72 (1H), 3.62 (2H), 4.41 (1H), 5.77 (1H), 6.96 (2H), 7.05 (2H) ppm.

EXAMPLE 6a (5R,8S,11R,13S,14S,17S)-11-[4-((1R,2R)-2-hydroxymethylcyclopropyl)phenyl]-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol (A) and (5R,8S,11R,13S,14S,17S)-11-[4-((1S,2S)-2-hydroxymethylcyclopropyl)phenyl]-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol (B)

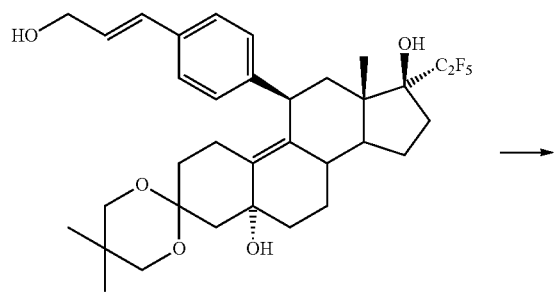

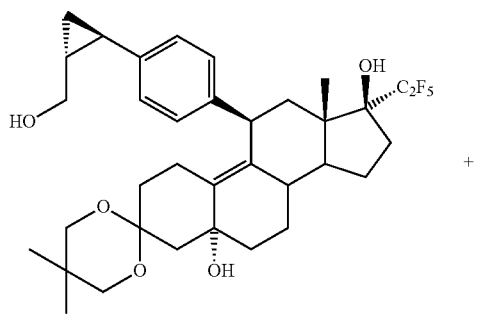

+

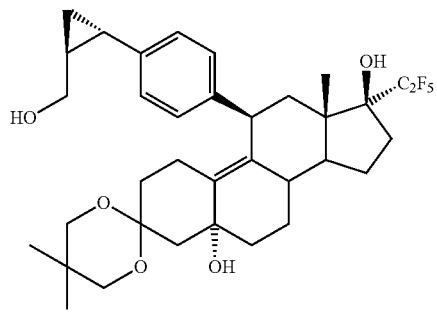

In analogy to Example 1a, 272 mg (0.43 mmol) of the compound prepared according to Example 6b were converted and, after workup and purification by chromatography, 25 mg (11%) of a mixture of the two title compounds were isolated as a colourless foam.

EXAMPLE 6b (5R,8S,11R,13S,14S,17S)-11-{4-[(1E)-3-hydroxyprop-1-en-1-yl]phenyl}-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

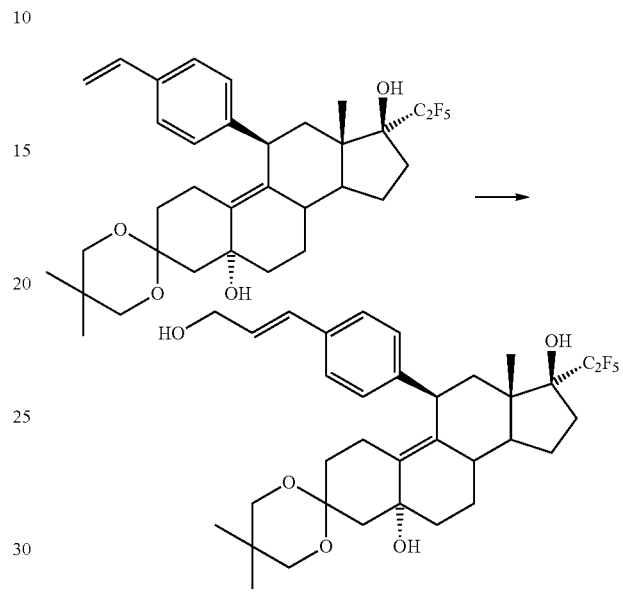

The solution of 1.0 g (1.68 mmol) of the compound prepared according to Example 2d in 16.5 ml of dichloromethane was admixed with 0.57 ml of allyl alcohol, 145 mg of [[1,3-bis(2,4,6-trimethylphenyl)-2-imidazolidinyl]methyl]dichloro(phenylmethylene)(tricyclohexylphosphoranyl)ruthenium, and heated under reflux for 4.5 hours. The mixture was purified by chromatography, and 163 mg (16%) of the title compound were isolated as a colourless foam.

EXAMPLE 7

(8S,11R,13S,14S,17S)-17-hydroxy-13-methyl-17-pentafluoroethyl-11-[4-(2-pyridin-3-ylethyl)phenyl]-1,2,6,7,8,11,12,13,14,15,16,17-dodecahydrocyclopenta[a]phenanthren-3-one

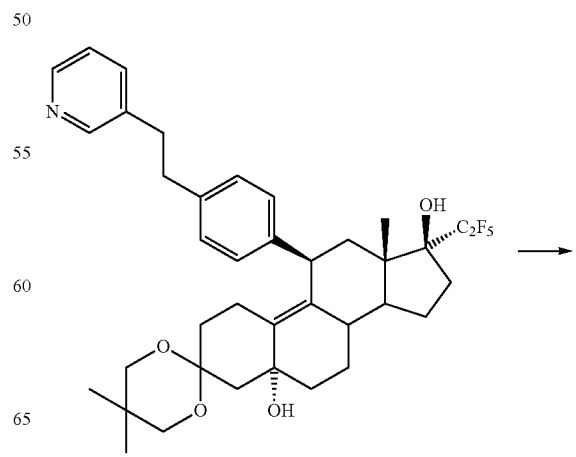

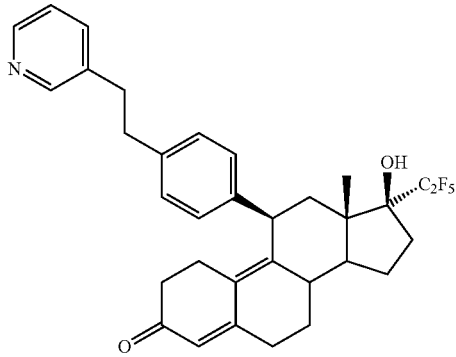

In analogy to Example 1, 54 mg (80 µmol) of the compound prepared according to Example 7a were converted and, after workup and purification, 16.3 mg (36%) of the title compound were isolated as a colourless foam.

$^1$H NMR (CDCl$_3$): δ=0.59 (3H), 1.39-1.57 (2H), 1.71-1.87 (3H), 2.05 (1H), 2.21-2.63 (10H), 2.73 (1H), 2.90 (4H), 4.40 (1H), 5.77 (1H), 6.99 (2H), 7.03 (2H), 7.19 (1H), 7.43 (1H), 8.24 (1H), 8.39 (1H) ppm.

EXAMPLE 7a (5R,8S,11R,13S,14S,17S)-11-[4-(2-pyridin-3-yl-ethyl)phenyl]-5'5,13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

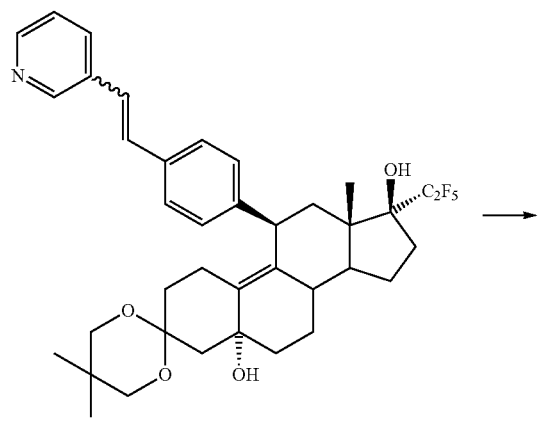

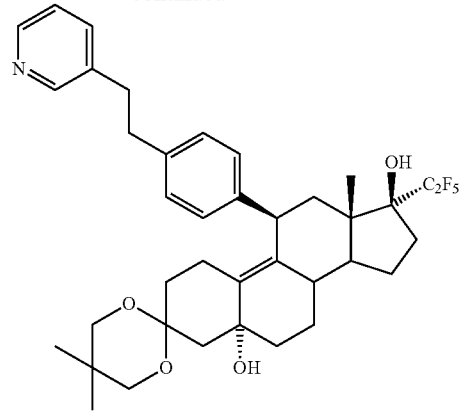

In analogy to Example 2a, 57 mg (85 µmol) of the compound prepared according to Example 7b were converted and, after workup and purification, 54 mg (94%) of the title compound were isolated as a colourless foam.

EXAMPLE 7b (5R,8S,11R,13S,14S,17S)-5',5',13-trimethyl-17-(pentafluoroethyl)-11-{4-[(E/Z)-2-(pyridin-3-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

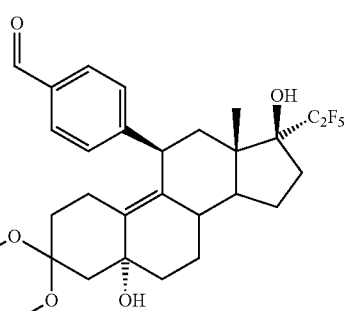

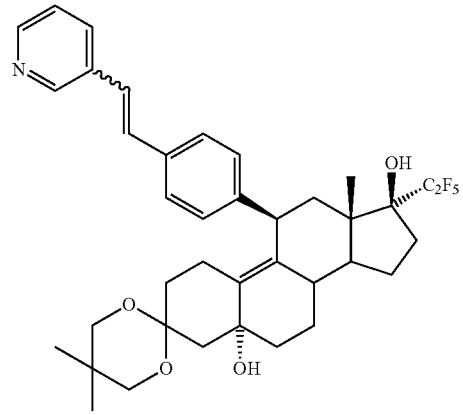

In analogy to Example 2b, 250 mg (0.42 mmol) of the compound prepared according to Example 2c were converted using diethyl pyridin-3-ylmethylphosphonate and, after workup and purification, 170 mg (60%) of a mixture of the two title compounds were isolated as a colourless foam.

EXAMPLE 8

(8S,11R,13S,14S,17S)-17-hydroxy-13-methyl-17-pentafluoroethyl-11-[4-(2-pyridin-4-ylethyl)phenyl]-1,2,6,7,8,11,12,13,14,15,16,17-dodecahydrocyclopenta[a]phenanthren-3-one

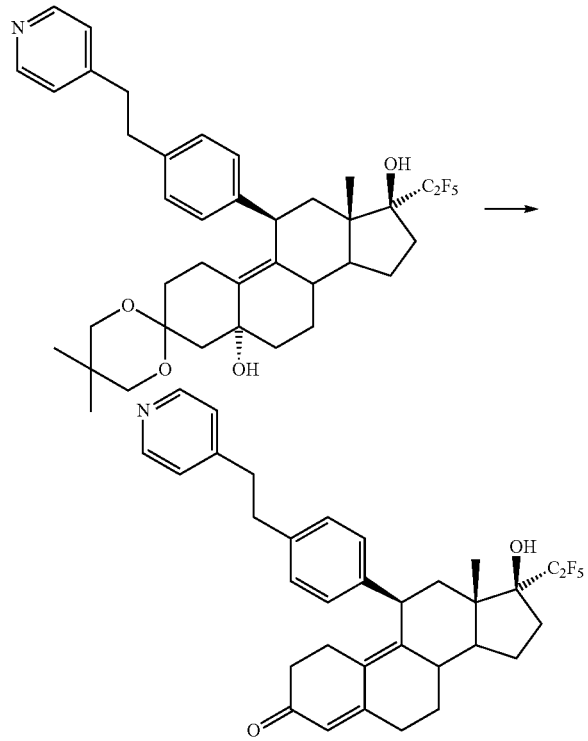

In analogy to Example 1, 80 mg (0.12 mmol) of the compound prepared according to Example 8a were converted and, after workup and purification, 23 mg (34%) of the title compound were isolated as a colourless foam.

$^1$H NMR (CDCl$_3$): δ=0.57 (3H), 1.36-1.89 (5H), 2.05 (1H), 2.20-2.65 (9H), 2.73 (1H), 2.90 (4H), 3.00 (1H). 4.41 (1H), 5.77 (1H), 6.92-7.11 (6H), 8.40 (2H) ppm.

EXAMPLE 8a (5R,8S,11R,13S,14S,17S)-11-[4-(2-pyridin-4-ylethyl)phenyl]-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

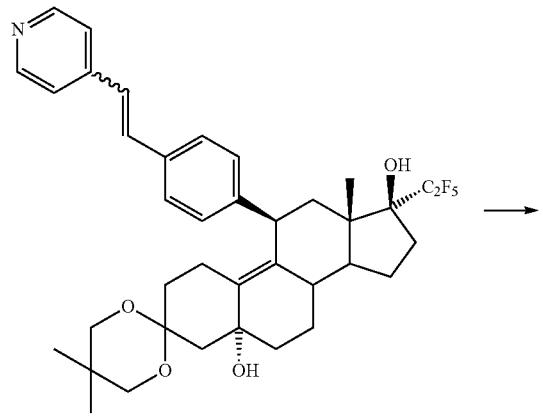

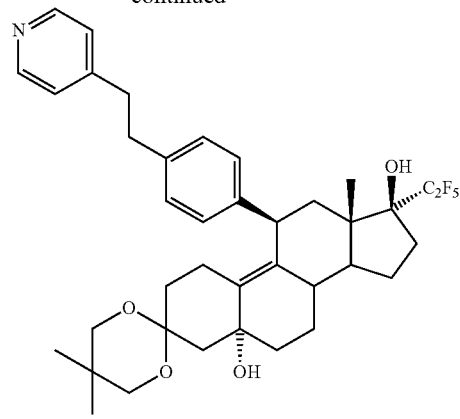

In analogy to Example 2a, 82 mg (0.12 mmol) of the compound prepared according to Example 8b were converted and, after workup and purification, 80 mg (97%) of the title compound were isolated as a colourless foam.

EXAMPLE 8b (5R,8S,11R,13S,14S,17S)-5',5',13-trimethyl-17-(pentafluoroethyl)-11-{4-[(E/Z)-2-(pyridin-4-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

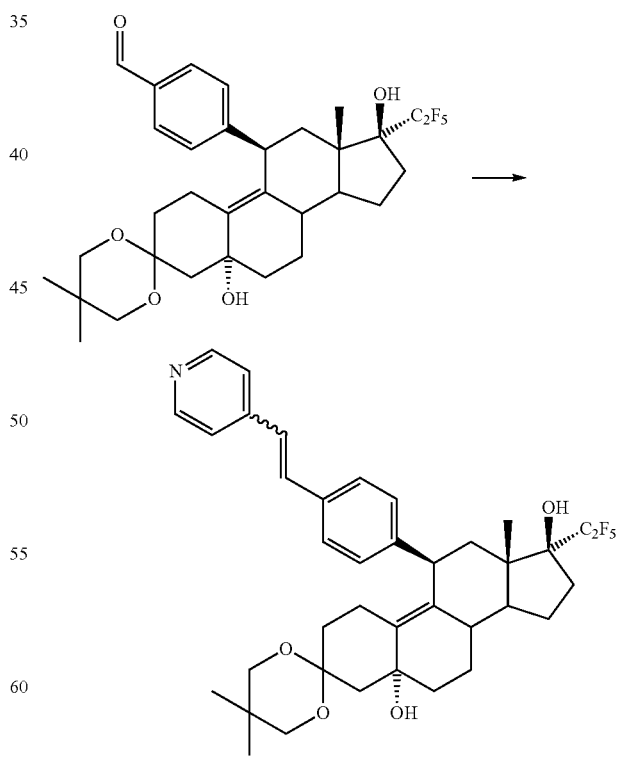

In analogy to Example 2b, 200 mg (0.33 mmol) of the compound prepared according to Example 2c were converted using diethyl pyridin-4-ylmethylphosphonate and, after workup and purification, 182 mg (81%) of a mixture of the two title compounds were isolated as a colourless foam.

EXAMPLE 9

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propionitrile

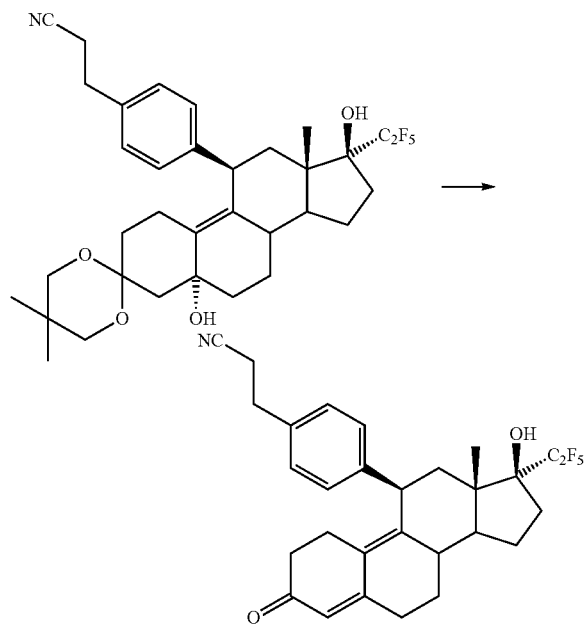

In analogy to Example 1, 70 mg (0.11 mmol) of the compound prepared according to Example 9a were converted and, after workup and purification, 46.3 mg (79%) of the title compound were isolated as a colourless foam.

$^1$H NMR (CDCl$_3$): δ=0.59 (3H), 1.39-1.55 (2H), 1.72-1.86 (3H), 2.01-2.11 (2H), 2.21-2.65 (11H), 2.74 (1H), 2.92 (2H), 4.43 (1H), 5.78 (1H), 7.15 (4H) ppm.

EXAMPLE 9a

3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)phenyl]propionitrile

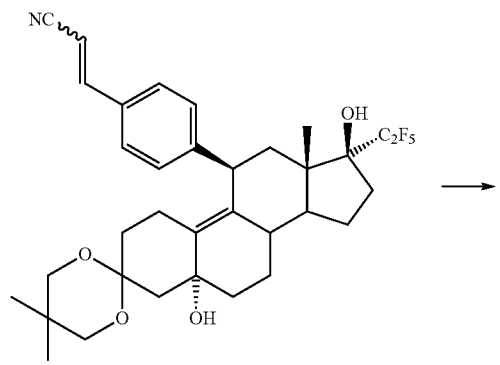

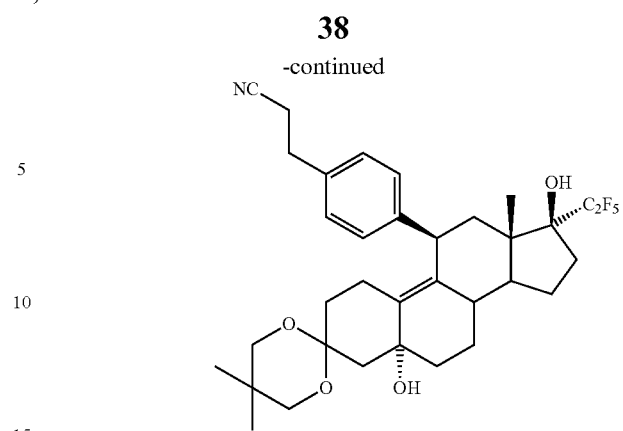

In analogy to Example 2a, 300 mg (0.48 mmol) of the compound prepared according to Example 9b were converted and, after workup and purification, 197 mg (65%) of the title compound were isolated as a colourless foam.

EXAMPLE 9b (2E/Z)-3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl}prop-2-enonitrile

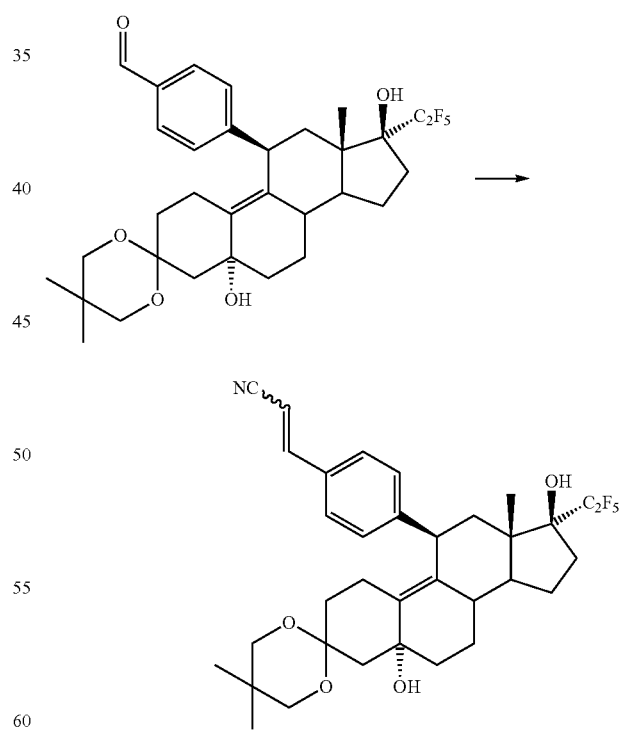

In analogy to Example 2b, 1.0 g (1.67 mmol) of the compound prepared according to Example 2c were converted using diethyl cyanomethylphosphonate and, after workup and purification, 961 mg (93%) of the title compound were isolated as a colourless foam.

EXAMPLE 10

(8S,11R,13S,14S,17S)-11-(3-acetylphenyl)-17-hydroxy-13-methyl-17-pentafluoroethyl-1,2,6,7,8,11,12,13,14,15,16,17-dodecahydrocyclopenta[a]phenanthren-3-one

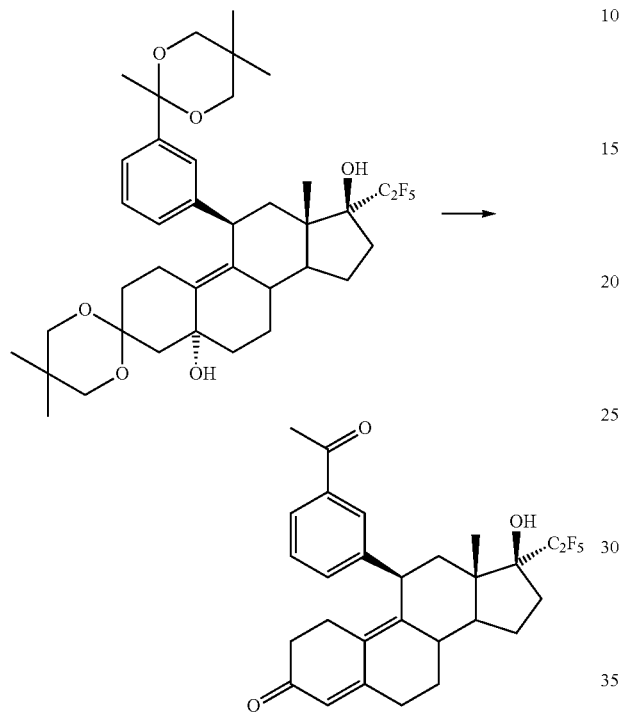

In analogy to Example 1, 15.9 g (22.7 mmol) of the compound prepared according to Example 10a were converted and, after workup and purification, 7.92 g (69%) of the title compound were isolated as a crystalline solid.

$^1$H NMR (CDCl$_3$): δ=0.57 (3H), 1.40-1.57 (2H), 1.73-1.88 (3H), 2.08 (1H), 2.17 (1H), 2.19-2.67 (9H), 2.59 (3H), 2.73 (1H), 4.50 (1H), 5.79 (1H), 7.35-7.41 (2H), 7.75 (1H), 7.85 (1H) ppm.

EXAMPLE 10a (5R,8S,11R,13S,14S,17S)-3,3-dimethoxy-13-methyl-17-pentafluoroethyl-11-[3-(2,5,5-trimethyl-[1,3]dioxan-2-yl)phenyl]-1,2,3,4,6,7,8,11,12,13,14,15,16,17-tetradecahydrospiro[cyclopenta[a]phenanthrene-3,2'-[1,3]dioxane]-5,17-diol

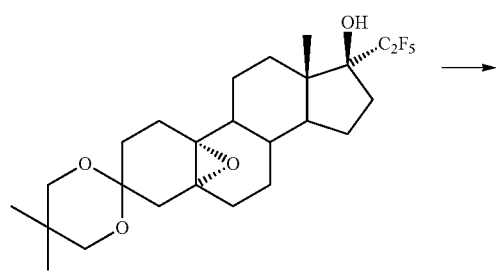

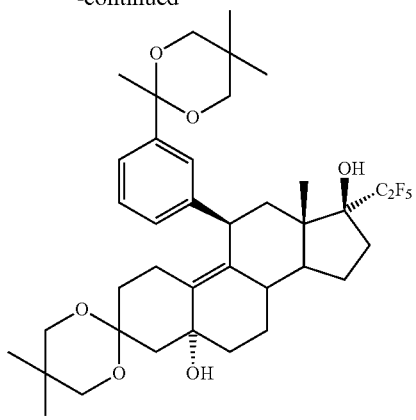

In analogy to Example 2d, 14 g (28.4 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were reacted with the Grignard reagent prepared from 33.1 g of 2-(3-bromophenyl)-2,5,5-trimethyl-1,3-dioxane and, after workup and purification, 17.7 g (89%) of the title compound were isolated as a colourless foam.

EXAMPLE 11

(8S,11R,13S,14S,17S)-17-hydroxy-11-[3-((RS)-1-hydroxyethyl)phenyl]-13-methyl-17-pentafluoroethyl-1,2,6,7,8,11,12,13,14,15,16,17-dodecahydrocyclopenta[a]phenanthren-3-one

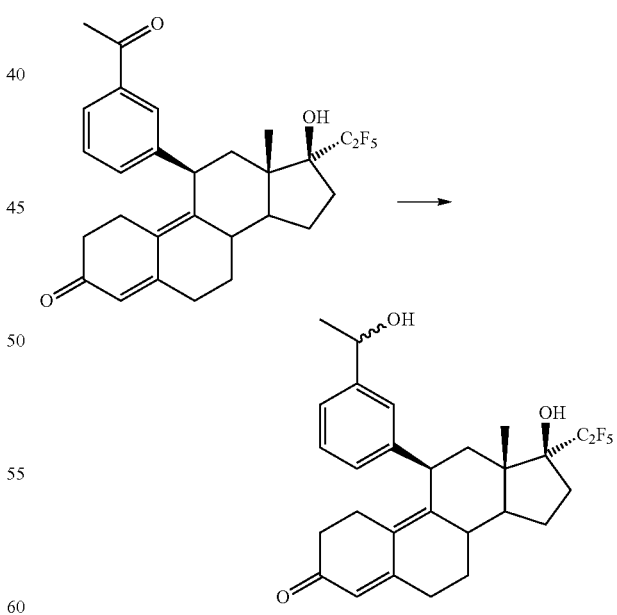

The solution of 100 mg (0.2 mmol) of the compound prepared according to Example 10 in 1.5 ml of isopropanol was admixed with 5.5 mg of yttrium(III) isopropoxide and heated to 95° C. for 6 hours. The mixture was concentrated and the residue was purified by chromatography. 54 mg (53%) of the title compounds were isolated as a colourless foam.

$^1$H NMR (CDCl$_3$): δ=0.54 (3H), 1.30-1.53 (3H), 1.48 (3H), 1.55-2.15 (8H), 2.19-2.56 (6H), 4.19-4.40 (2H), 4.87 (1H), 5.52+5.54 (1H), 7.09 (1H), 7.14 (1H), 7.22 (1H), 7.27 (1H) ppm.

EXAMPLE 12

(8S,11R,13S,14S,17S)-11-(3-cyclopropylphenyl)-17-hydroxy-13-methyl-17-pentafluoroethyl-1,2,6,7,8,11,12,13,14,15,16,17-dodecahydrocyclopenta[a]phenanthren-3-one

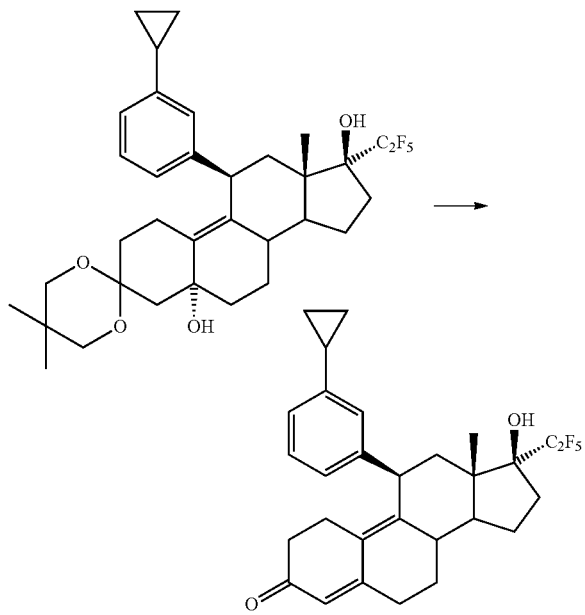

In analogy to Example 1, 108 mg (0.17 mmol) of the compound prepared according to Example 12a were converted and, after workup and purification, 50 mg (59%) of the title compound were isolated as a colourless foam.

$^1$H NMR (CDCl$_3$): δ=0.61 (3H), 0.65 (2H), 0.96 (2H), 1.41-1.56 (2H), 1.75-1.90 (4H), 2.02-2.11 (2H), 2.24-2.63 (9H), 2.73 (1H), 4.41 (1H), 5.78 (1H), 6.81 (1H), 6.91 (1H), 6.94 (1H), 7.14 (1H) ppm.

EXAMPLE 12a (5R,8S,11R,13S,14S,17S)-11-(3-cyclopropylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

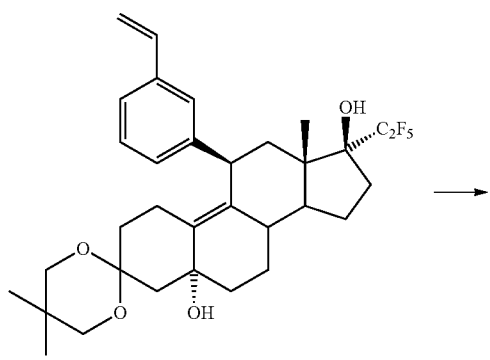

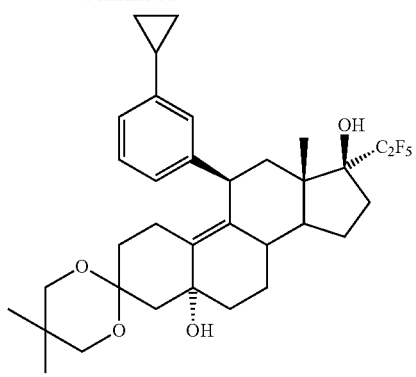

In analogy to Example 1a, 100 mg (0.17 mmol) of the compound prepared according to Example 12b were converted and, after workup and purification, 100 mg (98%) of the title compound were isolated as a colourless foam.

EXAMPLE 12b (5R,8S,11R,13S,14S,17S)-11-(3-ethenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

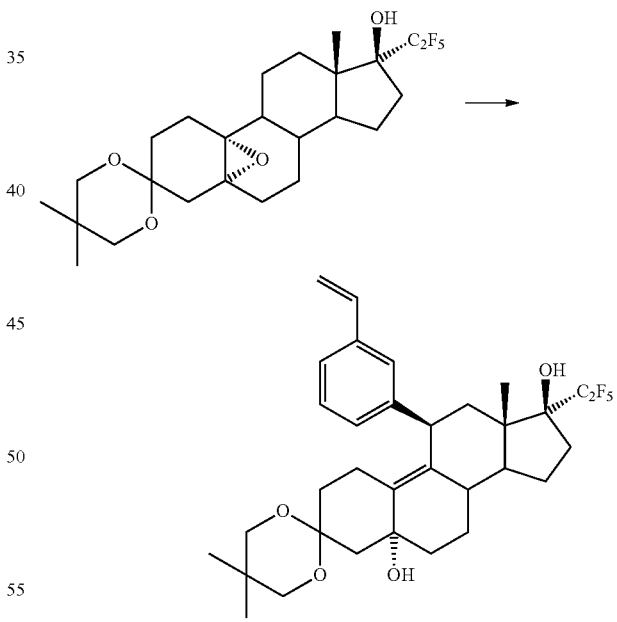

In analogy to Example 2d, 15 g (30.5 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were reacted with the Grignard reagent prepared from 12 ml of 3-bromostyrene and, after workup and purification, 16.6 g (92%) of the title compound were isolated as a colourless foam.

EXAMPLE 13

(8S,11R,13S,14S,17S)-17-hydroxy-13-methyl-11-[3-(1-methylcyclopropyl)phenyl]-17-pentafluoroethyl-1,2,6,7,8,11,12,13,14,15,16,17-dodecahydrocyclopenta[a]phenanthren-3-one

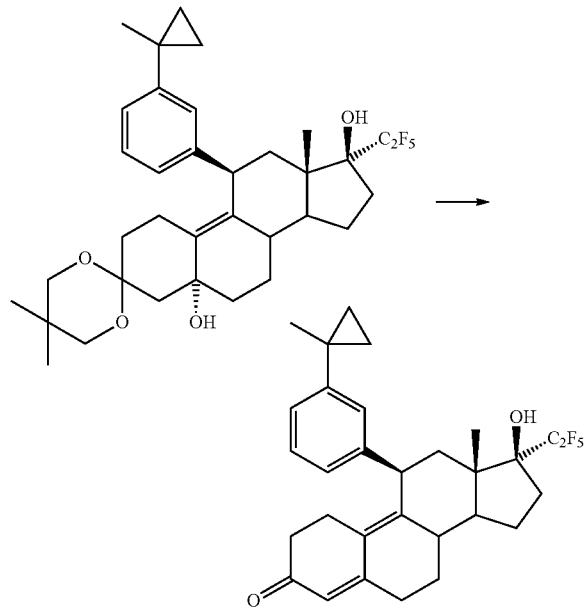

In analogy to Example 1, 110 mg (0.18 mmol) of the compound prepared according to Example 13a were converted and, after workup and purification, 50 mg (55%) of the title compound were isolated as a colourless foam.

$^1$H NMR (CDCl$_3$): δ=0.60 (3H), 0.74 (2H), 0.81 (2H), 1.38 (3H), 1.42-1.55 (2H), 1.75-1.86 (3H), 2.02-2.11 (2H), 2.23-2.64 (9H), 2.73 (1H), 4.43 (1H), 5.79 (1H), 6.93 (1H), 7.03 (1H), 7.07 (1H), 7.17 (1H) ppm.

EXAMPLE 13a (5R,8S,11R,13S,14S,17S)-5',5',13-trimethyl-11-[3-(1-methylcyclopropyl)phenyl]-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

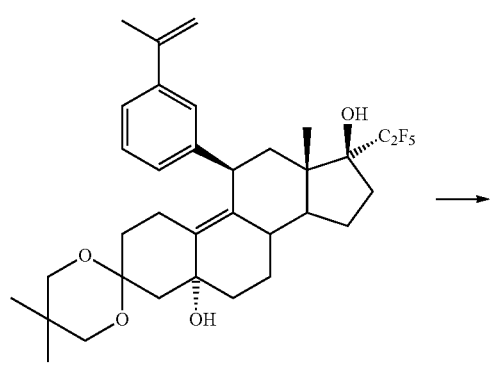

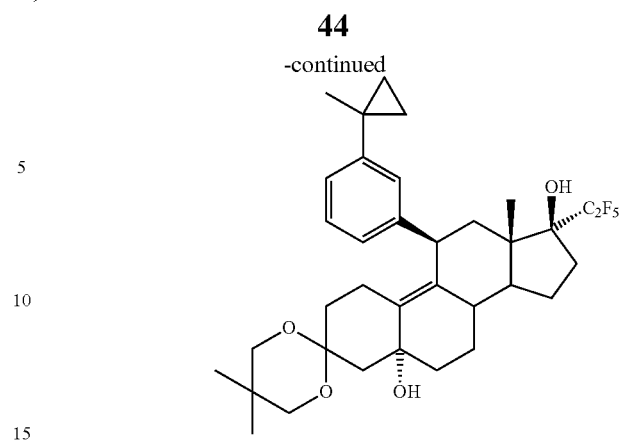

In analogy to Example 1a, 100 mg (0.16 mmol) of the compound prepared according to Example 13b were converted and, after workup and purification, 100 mg (98%) of the title compound were isolated as a colourless foam.

EXAMPLE 13b (5R,8S,11R,13S,14S,17S)-11-(3-isopropenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

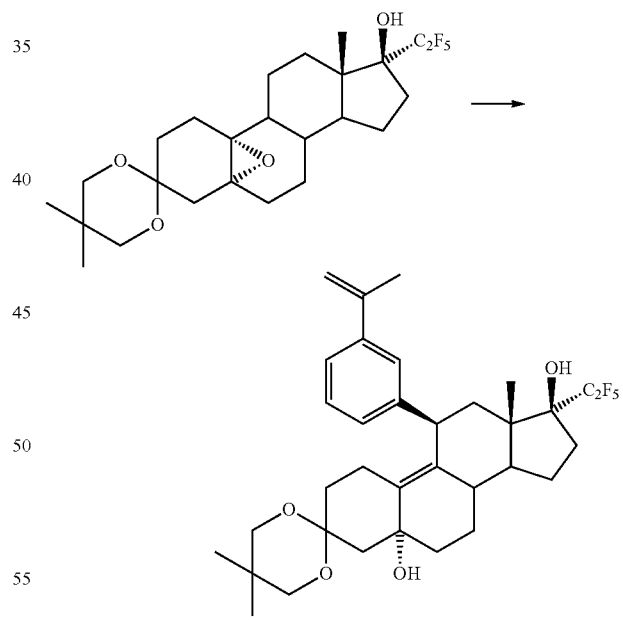

In analogy to Example 2d, 5.9 g (12.0 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were reacted with the Grignard reagent prepared from 11.9 g of 1-bromo-3-isopropenylbenzene and, after workup and purification, 5.36 g (73%) of the title compound were isolated as a colourless foam.

EXAMPLE 14

(8S,11R,13S,14S,17S)-17-hydroxy-11-[3-(2-hydroxyethyl)phenyl]-13-methyl-17-pentafluoroethyl-1,2,6,7,8,11,12,13,14,15,16,17-dodecahydrocyclopenta[a]phenanthren-3-one

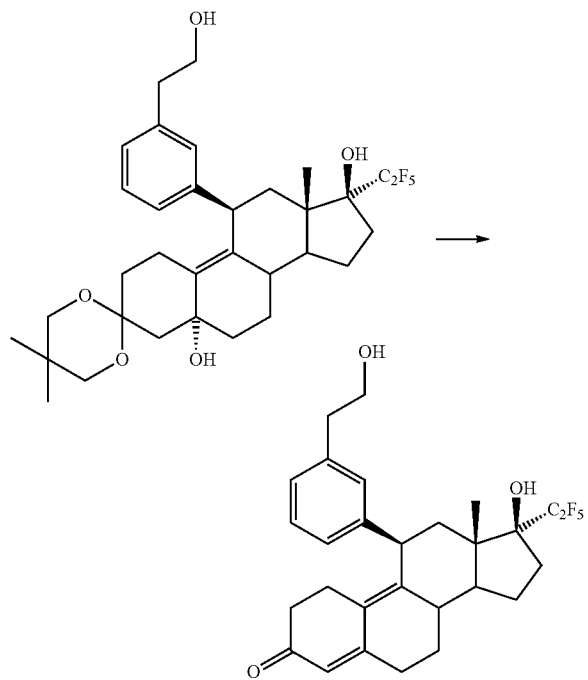

In analogy to Example 1, 50 mg (81 µmol) of the compound prepared according to Example 14a were converted and, after workup and purification, 31.2 mg (75%) of the title compound were isolated as a colourless foam.

$^1$H NMR (CDCl$_3$): δ=0.59 (3H), 1.41-1.55 (2H), 1.74-1.86 (3H), 2.06 (1H), 2.20-2.64 (10H), 2.74 (1H), 2.85 (2H), 3.51 (1H), 3.84 (2H), 4.43 (1H), 5.78 (1H), 7.00 (1H), 7.04 (1H), 7.08 (1H), 7.22 (1H) ppm.

EXAMPLE 14a (5R,8S,11R,13S,14S,17S)-5',5',13-trimethyl-11-[3-(2-hydroxyethyl)phenyl]-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

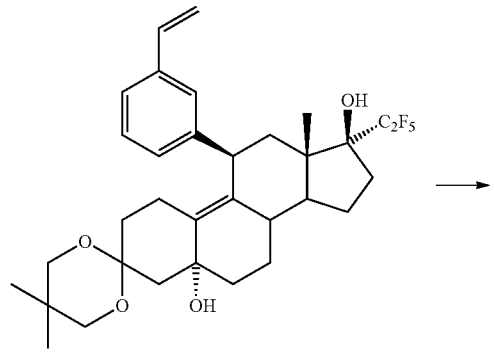

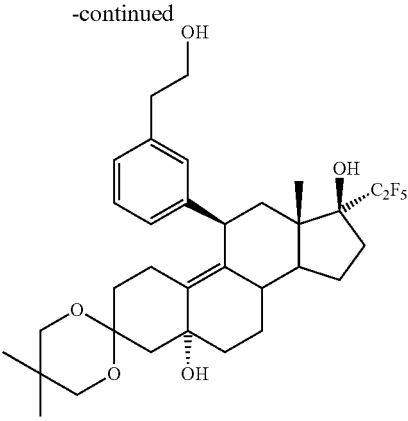

To the solution of 500 mg (0.84 mmol) of the compound prepared according to Example 14b in 5 ml of tetrahydrofuran were added dropwise 6.3 ml of a 0.5 molar solution of 9-borabicyclo[3.3.1]nonane in tetrahydrofuran, and the mixture was stirred at 23° C. for 4 hours. The mixture was cooled to 3° C., 2.8 ml of a 5% sodium hydroxide solution and 0.72 ml of a 30% hydrogen peroxide solution were added, and the mixture was stirred overnight. It was extracted repeatedly with ethyl acetate, washed with water and a saturated sodium thiosulphate solution and dried over sodium sulphate. The residue obtained after filtration and solvent removal was purified by chromatography. 346 mg (67%) of the title compound were isolated as a colourless foam.

EXAMPLE 14b (5R,8S,11R,13S,14S,17S)-11-(3-ethenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

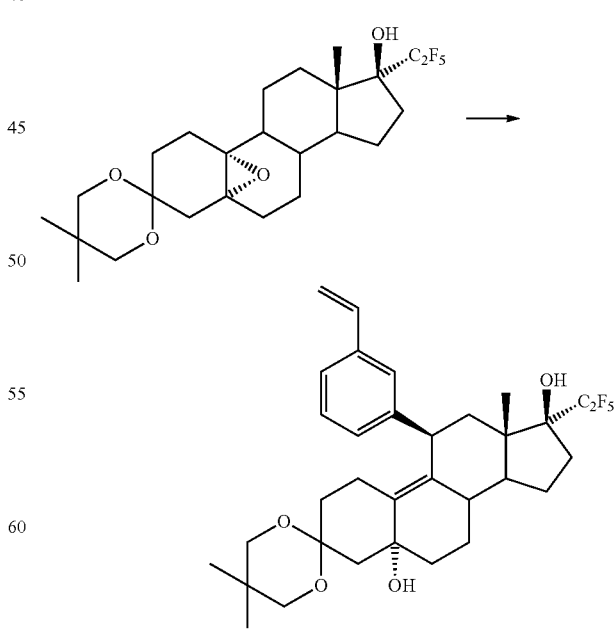

In analogy to Example 2d, 15 g (30.5 mmol) of (5R,8S,10R,13S,14S,17S)-17-(pentafluoroethyl)-5,10-epoxy-5',5', 13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were reacted with the Grignard reagent prepared from 12 ml of 3-bromostyrene and, after workup and purification, 16.6 g (92%) of the title compound were isolated as a colourless foam.

EXAMPLE 15

(8S,11R,13S,14S,17S)-17-hydroxy-11-[4-(2-hydroxy-1-hydroxymethyl-1-methylethyl)phenyl]-13-methyl-17-pentafluoroethyl-1,2,6,7,8,11,12,13,14,15,16,17-dodecahydrocyclopenta[a]phenanthren-3-one (A) and (8S,11R,13S,14S,17S)-17-hydroxy-13-methyl-17-pentafluoroethyl-11-[4-(2,2,5-trimethyl-[1,3]dioxan-5-yl)phenyl]-1,2,6,7,8,11,12,13,14,15,16,17-dodecahydrocyclopenta[a]phenanthren-3-one (B)

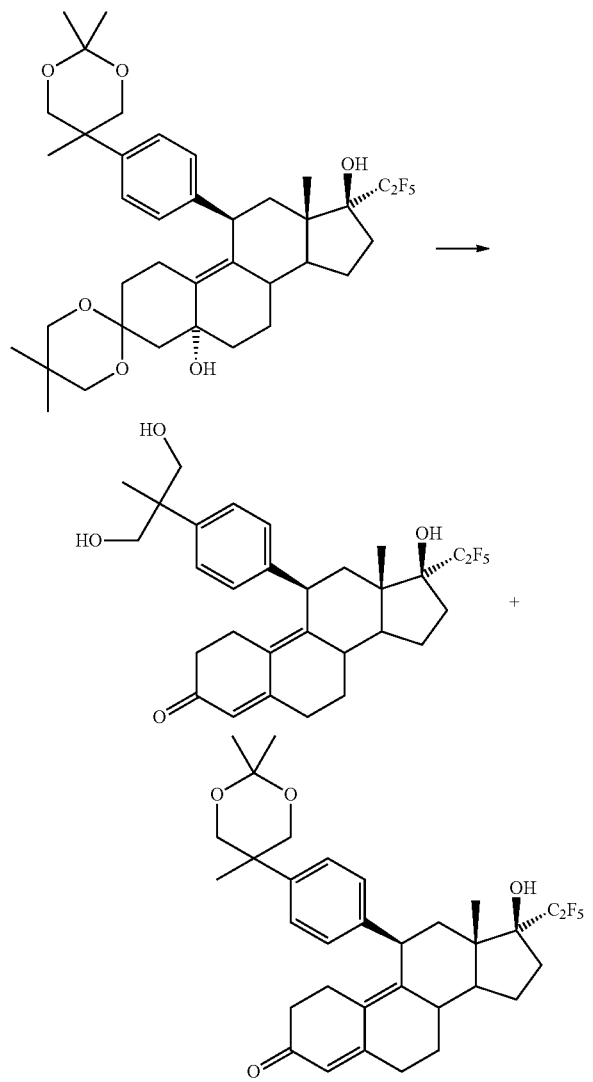

In analogy to Example 1, 200 mg (290 µmol) of the compound prepared according to Example 15a were reacted and, after workup and purification, 55 mg (35%) of title compound A and 40 mg (24%) of title compound B were isolated, each as a colourless foam.

$^1$H NMR (CDCl$_3$) of A: δ=0.58 (3H), 1.27 (3H), 1.38-1.57 (2H), 1.71-1.87 (3H), 1.99-2.18 (3H), 2.27 (1H), 2.22-2.64 (9H), 2.74 (1H), 3.81 (2H), 3.95 (2H), 4.43 (1H), 5.78 (1H), 7.17 (2H), 7.33 (2H) ppm.

$^1$H NMR (CDCl$_3$) of B: δ=0.59 (3H), 1.41 (3H), 1.44 (3H), 1.48 (3H), 1.36-1.56 (2H), 1.74-1.85 (3H), 2.01-2.10 (2H), 2.25-2.63 (9H), 2.74 (1H), 3.73 (2H), 4.09 (2H), 4.43 (1H), 5.78 (1H), 7.14 (2H), 7.25 (2H) ppm.

EXAMPLE 15a (5R,8S,11R,13S,14S,17S)-5',5',13-trimethyl-17-pentafluoroethyl-11-[4-(2,5,5-trimethyl-[1,3]dioxan-2-yl)phenyl]-2,3,4,6,7,8,11,12,13,14,15,16,17-tetradecahydro-1H-spiro[cyclopenta[a]phenanthrene-3,2'-[1,3]dioxane]-5,17-diol

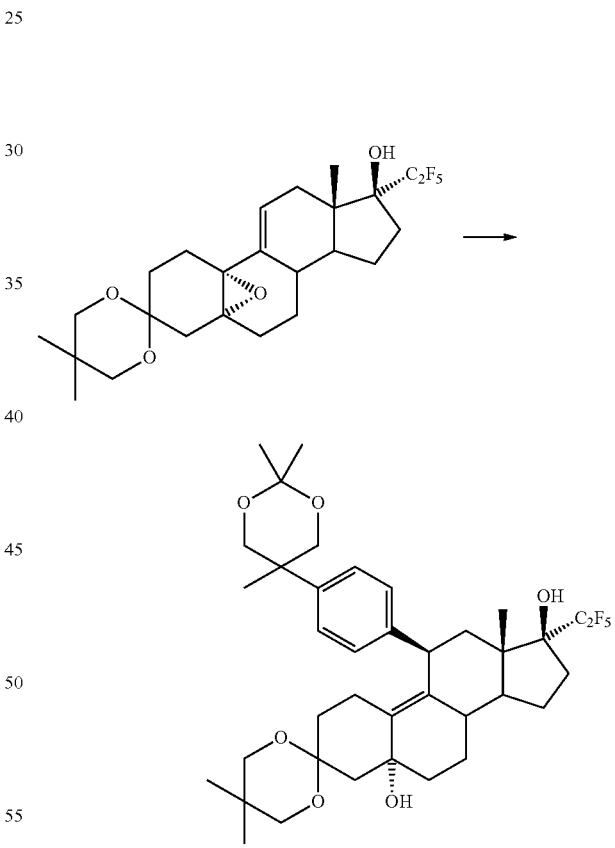

In analogy to Example 2d, 500 mg (1.02 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were converted using freshly prepared 4-(2,5,5-trimethyl-[1,3]dioxan-2-yl)phenylmagnesium bromide and, after workup and purification, 617 mg (87%) of the title compound were isolated as a colourless foam.

EXAMPLE 16

(8S,11R,13S,14S,17S)-17-hydroxy-11-[4-(2-hydroxy-1-hydroxymethylethyl)phenyl]-13-methyl-17-pentafluoroethyl-1,2,6,7,8,11,12,13,14,15,16,17-dodecahydrocyclopenta[a]phenanthren-3-one

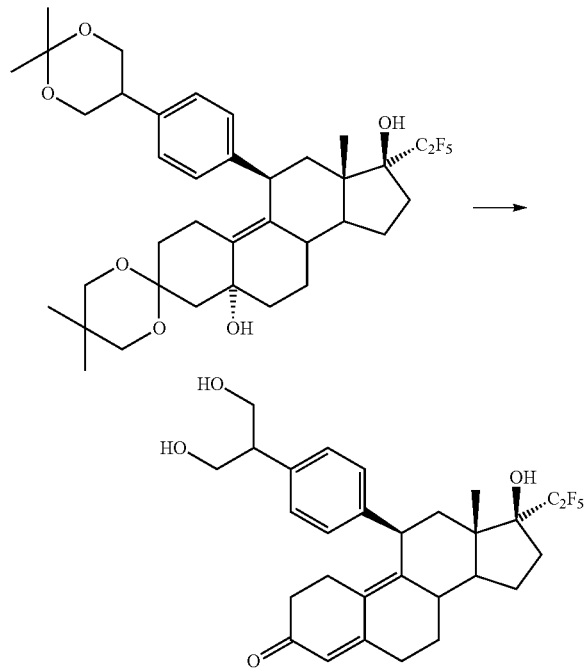

In analogy to Example 1, 200 mg (290 µmol) of the compound prepared according to Example 16a were converted and, after workup and purification, 74 mg (47%) of the title compound were isolated as a colourless foam.

$^1$H NMR (CDCl$_3$): δ=0.58 (3H), 1.40-1.57 (2H), 1.70-1.89 (3H), 2.05 (1H), 2.13-2.66 (12H), 2.73 (1H), 3.07 (1H), 3.84-4.06 (4H), 4.43 (1H), 5.78 (1H), 7.14 (4H) ppm.

EXAMPLE 16a (5R,8S,11R,13S,14S,17S)-5',5',13-trimethyl-17-pentafluoroethyl-11-[4-(5,5-dimethyl-[1,3]dioxan-2-yl)phenyl]-2,3,4,6,7,8,11,12,13,14,15,16,17-tetradecahydro-1H-spiro[cyclopenta[a]phenanthrene-3,2'-[1,3]dioxane]-5,17-diol

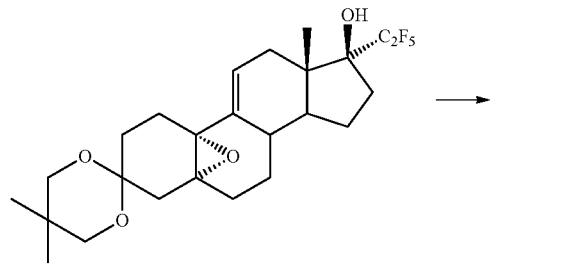

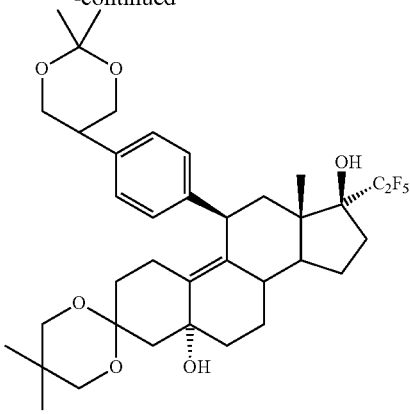

In analogy to Example 2d, 1.4 g (2.84 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, were converted using freshly prepared 4-(5,5-dimethyl-[1,3]dioxan-2-yl)phenylmagnesium bromide and, after workup and purification, 1.43 g (73%) of the title compound were isolated as a colourless foam.

EXAMPLE 17

1-ethyl-3-[4-((8S,11R,13S,14S,17S)-17-hydroxy-13-methyl-3-oxo-17-pentafluoroethyl-2,3,6,7,8,11,12,13,14,15,16,17-dodecahydro-M-cyclopenta[a]phenanthren-11-yl)benzyl]urea

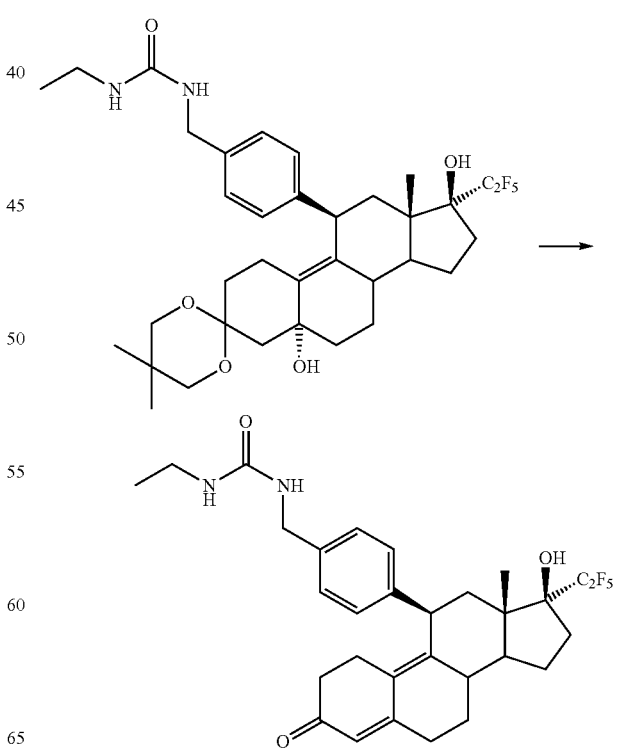

In analogy to Example 1, 44 mg (max. 67 μmol) of the compound prepared according to Example 17a were converted and, after workup and purification, 16 mg (43%) of the title compound were isolated as a colourless foam.

$^1$H NMR (CDCl$_3$): δ=0.57 (3H), 1.07 (3H), 1.36-1.56 (2H), 1.71-1.89 (3H), 2.05 (1H), 2.14-2.64 (9H), 2.70 (1H), 3.09-3.24 (3H), 4.20 (1H), 4.29 (1H), 4.40 (1H), 4.60 (1H), 4.91 (1H), 5.75 (1H), 7.10 (2H), 7.15 (2H) ppm.

EXAMPLE 17a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-ethyl urea

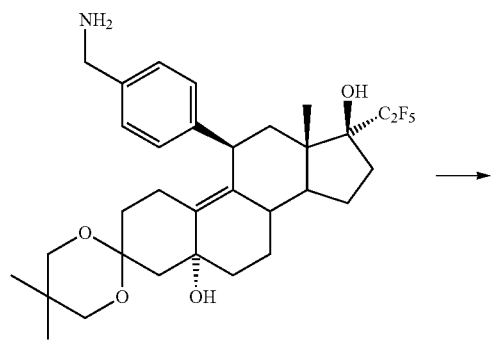

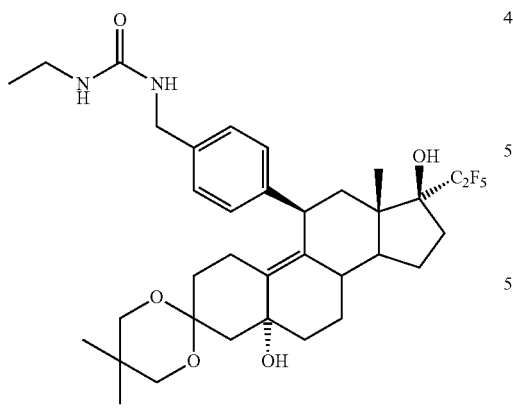

The solution of 40 mg (67 μmol) of the compound prepared according to Example 17b in 0.5 ml of dichloromethane was admixed with 5.5 μl of ethyl isocyanate and stirred at 23° C. for 1 hour. The mixture was concentrated and the resulting crude product was converted further without purification.

EXAMPLE 17b (5R,8S,11R,13S,14S,17S)-11-(4-aminomethylphenyl)-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxane]-5,17-diol

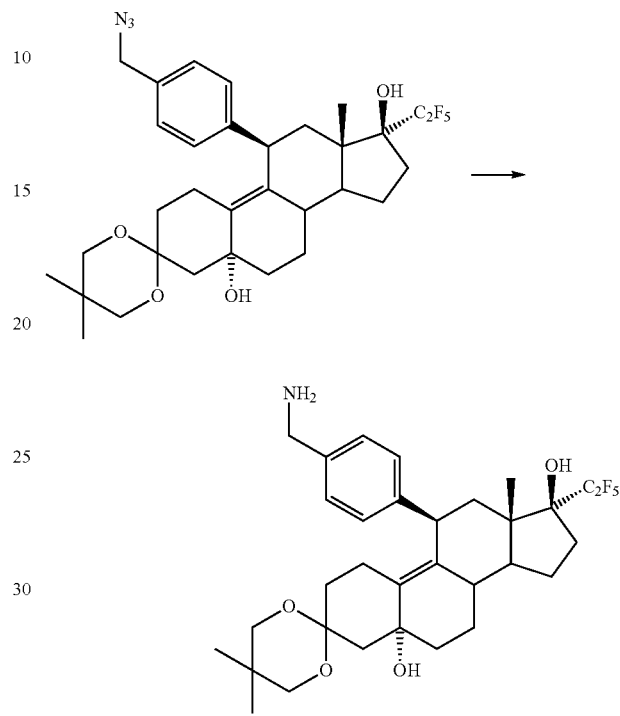

The solution of 1.8 g (2.88 mmol) of the compound prepared according to Example 17c in 50 ml of tetrahydrofuran was admixed with 8 ml of water, 0.56 ml of trimethylphosphine, and stirred at 23° C. for 4 hours. 6 ml of a 25% ammonia solution was added, and the mixture was stirred at 23° C. for a further 16 hours and concentrated. The title compound obtained as a crude product was converted further without purification.

EXAMPLE 17c (5R,8S,11R,13S,14S,17S)-11-(4-azidomethylphenyl)-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxane-5,17-diol

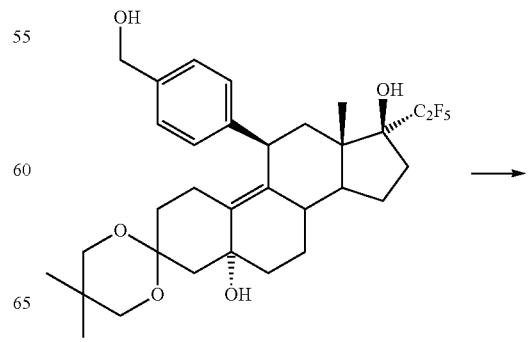

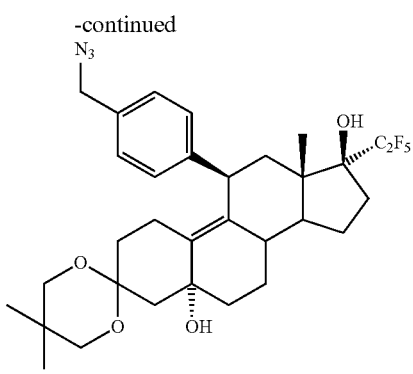

The solution of 2.0 g (3.33 mmol) of the compound prepared according to Example 17d in 50 ml of tetrahydrofuran was admixed at 3° C. with 1 ml of diphenylphosphoryl azide, 0.58 ml of 1,8-diazabicyclo[5.4.0]undec-7-ene, and the mixture was left to react at 23° C. for 4 hours and at 60° C. for a further 16 hours. Water was added to the mixture, which was extracted repeatedly with ethyl acetate, and the combined organic extracts were washed with saturated sodium chloride solution and dried over sodium sulphate. The residue obtained after filtration and solvent removal was purified by chromatography. 1.85 g (89%) of the title compound were isolated as a colourless foam.

EXAMPLE 17d (5R,8S,11R,13S,14S,17S)-11-(4-hydroxymethylphenyl)-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxane-5,17-diol

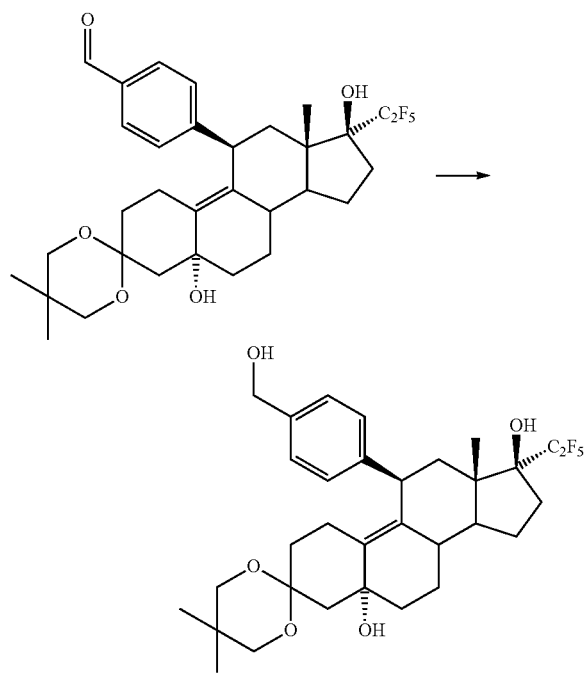

The solution of 2.0 g (3.34 mmol) of the compound prepared according to Example 2c in 12 ml of tetrahydrofuran and 1.2 ml of methanol was admixed at 3° C. with 70 mg of sodium borohydride and stirred for 2.5 hours. The mixture was poured into saturated ammonium chloride solution and extracted repeatedly with ethyl acetate, and the combined organic extracts were washed with saturated sodium chloride solution and dried over sodium sulphate. After filtration and removal of solvent, 2.0 g (100%) of the title compound were isolated as a colourless foam, which was converted further without purification.

EXAMPLE 18

1-allyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

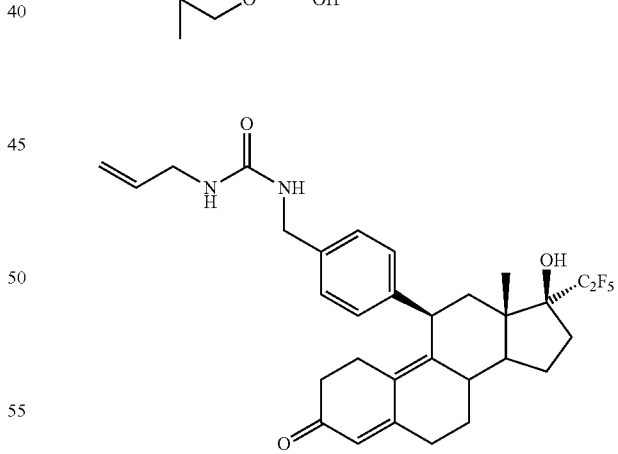

In analogy to Example 1, the crude product prepared according to Example 18a was converted and, after workup and purification, 18.6 mg (48%) of the title compound were isolated as a colourless foam.

$^1$H NMR (CDCl$_3$): δ=0.58 (3H), 1.37-1.56 (2H), 1.71-1.88 (3H), 2.05 (1H), 2.16-2.64 (9H), 2.65-2.77 (2H), 3.78 (2H), 4.22-4.37 (2H), 4.42 (1H), 4.61 (1H), 4.86 (1H), 5.08 (1H), 5.14 (1H), 5.76 (1H), 5.82 (1H), 7.11 (2H), 7.17 (2H) ppm.

EXAMPLE 18a 1-allyl-3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]urea

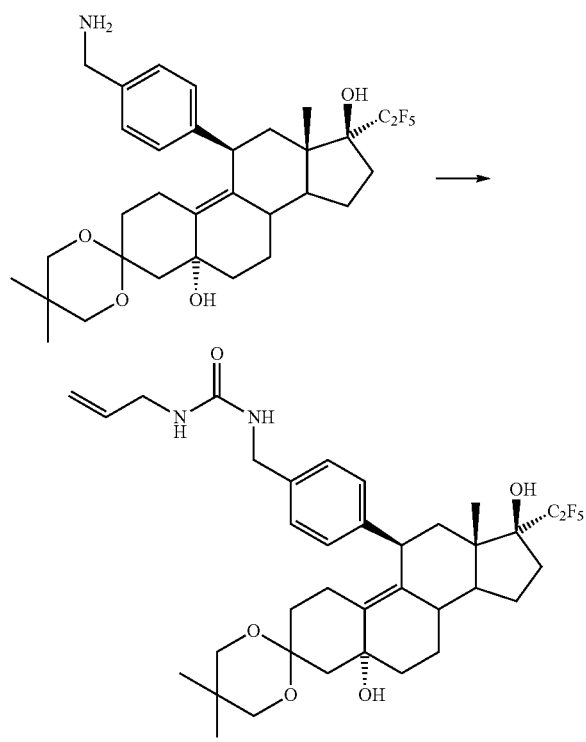

In analogy to Example 17a, 40 mg (67 μmol) of the compound prepared according to Example 17b were converted using allyl isocyanate. The crude product isolated after workup was converted further without purification.

EXAMPLE 19

1-isopropyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

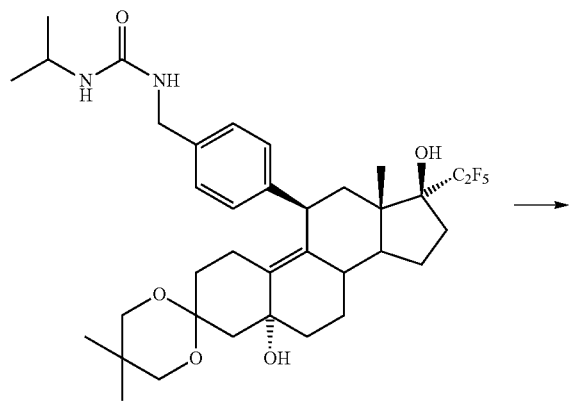

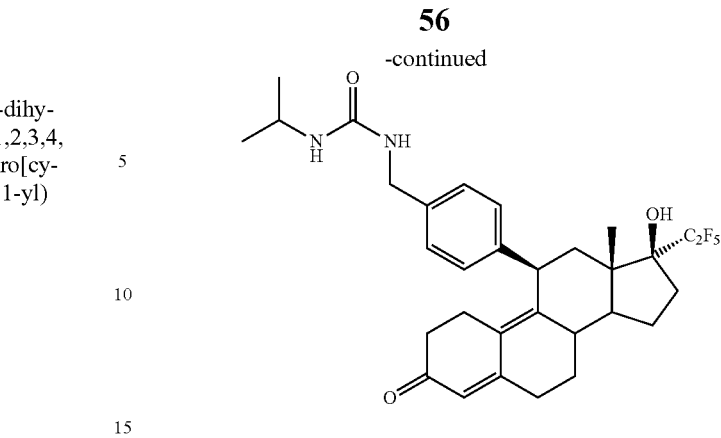

In analogy to Example 1, the crude product prepared according to Example 19a was converted and, after workup and purification, 16.9 mg (43%) of the title compound were isolated as a colourless foam.

$^1$H NMR (CDCl$_3$): δ=0.58 (3H), 1.11 (6H), 1.37-1.56 (2H), 1.72-1.88 (3H), 2.05 (1H), 2.16-2.64 (9H), 2.71 (1H), 2.81 (1H), 3.83 (1H), 4.19-4.36 (3H), 4.41 (1H), 4.69 (1H), 5.76 (1H), 7.11 (2H), 7.17 (2H) ppm.

EXAMPLE 19a 1-isopropyl-3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]urea

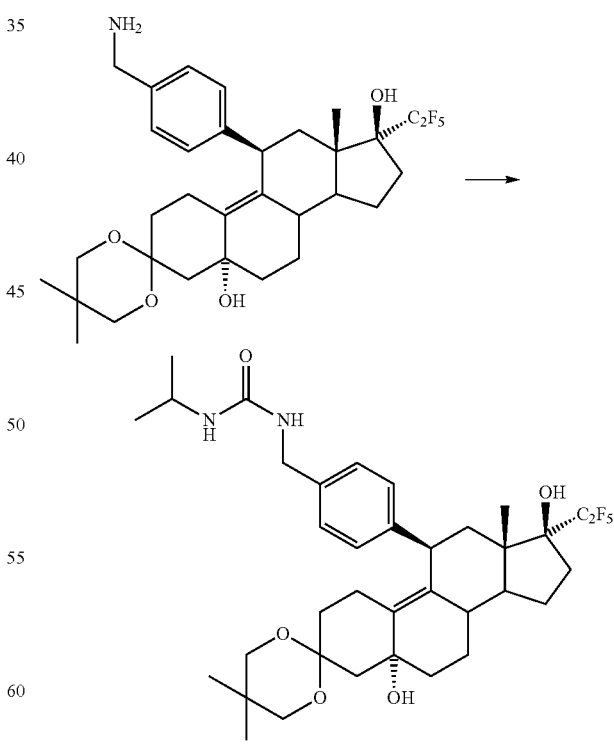

In analogy to Example 17a, 40 mg (67 μmol) of the compound prepared according to Example 17b were converted using isopropyl isocyanate. The crude product isolated after workup was converted further without purification.

EXAMPLE 20

1-tert-butyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

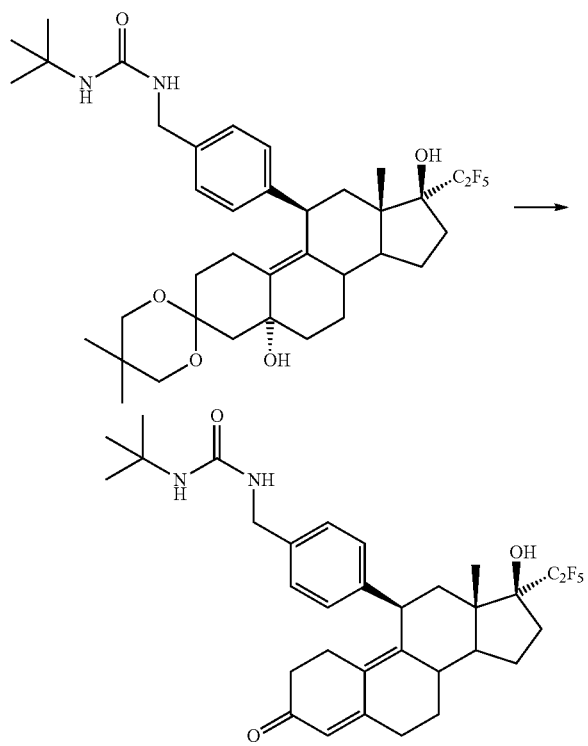

In analogy to Example 1, the crude product prepared according to Example 20a was converted and, after workup and purification, 18.4 mg (46%) of the title compound were isolated as a colourless foam.

$^1$H NMR (CDCl$_3$): δ=0.58 (3H), 1.31 (9H), 1.39-1.56 (2H), 1.72-1.87 (3H), 2.05 (1H), 2.17-2.63 (10H), 2.71 (1H), 4.18-4.34 (3H), 4.42 (1H), 4.53 (1H), 5.77 (1H), 7.11 (2H), 7.18 (2H) ppm.

EXAMPLE 20a 1-tert-butyl-3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]urea

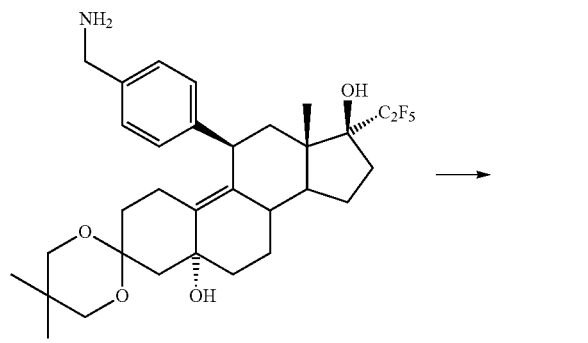

-continued

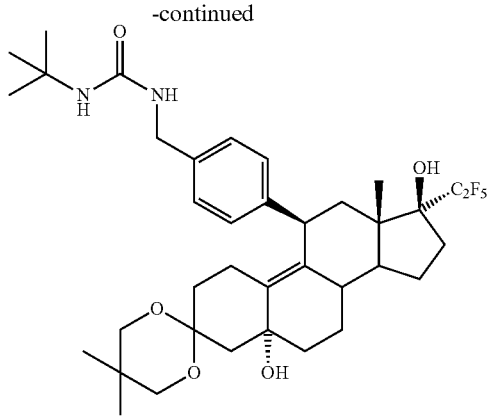

In analogy to Example 17a, 40 mg (67 µmol) of the compound prepared according to Example 17b were converted using tert-butyl isocyanate. The crude product isolated after workup was converted further without purification.

EXAMPLE 21

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}acetic acid ethyl ester

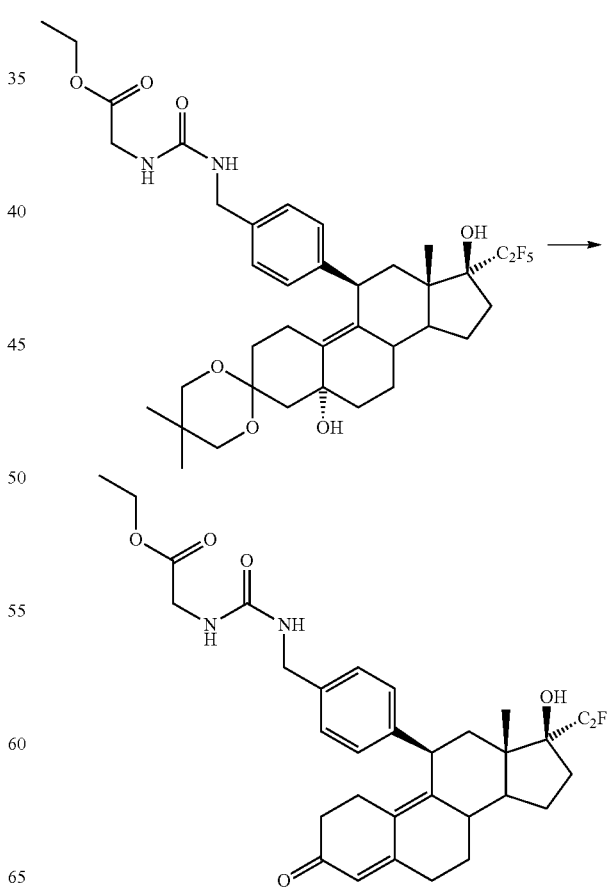

In analogy to Example 1, the crude product prepared according to Example 21a was converted and, after workup and purification, 16.7 mg (40%) of the title compound were isolated as a colourless foam.

$^1$H NMR (CDCl$_3$): δ=0.57 (3H), 1.26 (3H), 1.37-1.55 (2H), 1.71-1.87 (3H), 2.05 (1H), 2.17-2.63 (9H), 2.66 (1H), 2.71 (1H), 3.90-4.06 (3H), 4.13-4.24 (2H), 4.31 (1H), 4.42 (1H), 5.06 (2H), 5.77 (1H), 7.11 (2H), 7.18 (2H) ppm.

EXAMPLE 21a

{3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]ureido}acetic acid ethyl ester

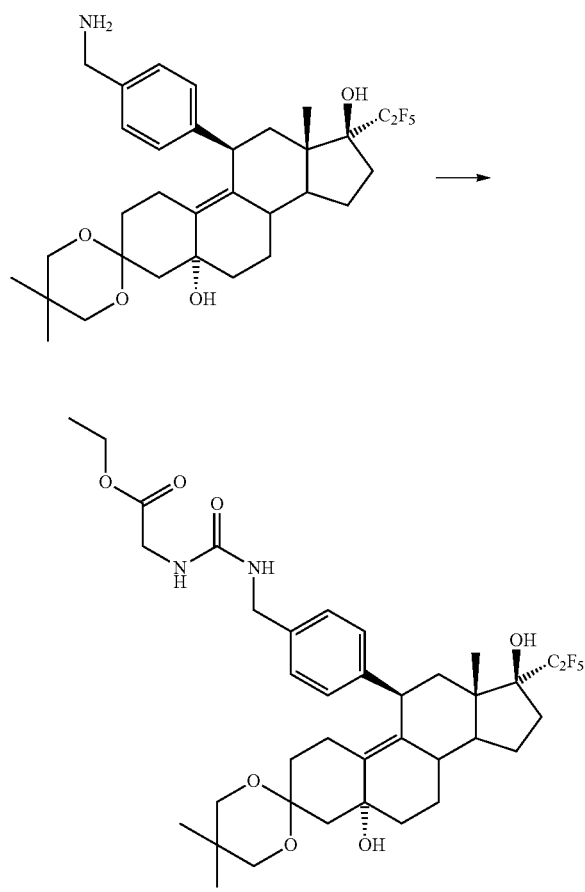

In analogy to Example 17a, 40 mg (67 μmol) of the compound prepared according to Example 17b were converted using ethyl isocyanatoacetate. The crude product isolated after workup was converted further without purification.

EXAMPLE 22

3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}propionic acid ethyl ester

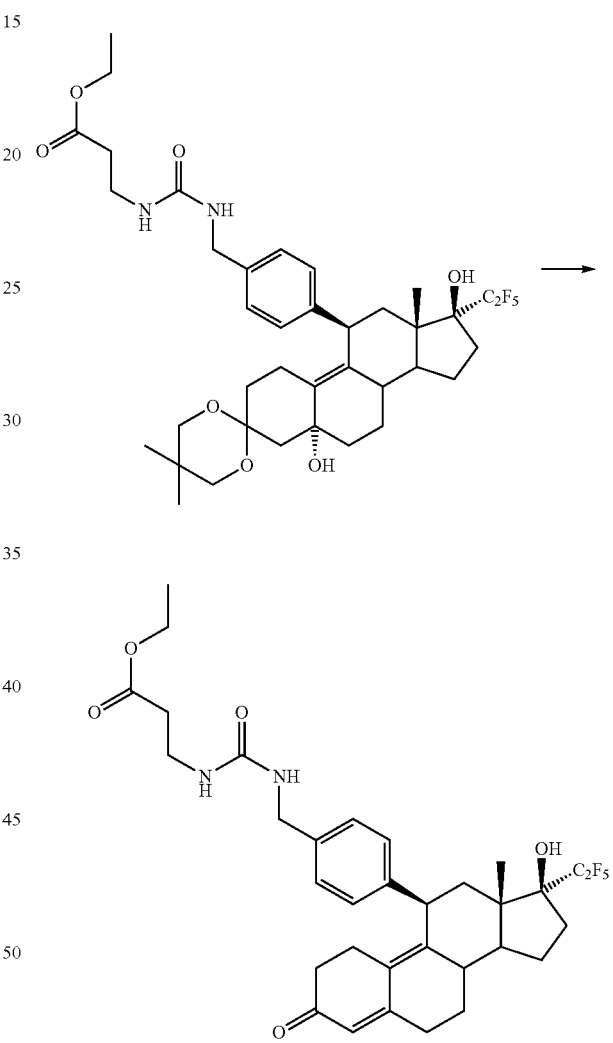

In analogy to Example 1, the crude product prepared according to Example 22a was converted and, after workup and purification, 16.4 mg (38%) of the title compound were isolated as a colourless foam.

$^1$H NMR (CDCl$_3$): δ=0.58 (3H), 1.25 (3H), 1.38-1.56 (2H), 1.71-1.88 (3H), 2.05 (1H), 2.17-2.65 (11H), 2.71 (1H), 2.74 (1H), 3.44 (2H), 4.09 (1H), 4.14 (1H), 4.20-4.35 (2H), 4.42 (1H), 4.82 (1H), 5.05 (1H), 5.77 (1H), 7.11 (2H), 7.17 (2H) ppm.

EXAMPLE 22a

3-{3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]ureido}propionic acid ethyl ester

EXAMPLE 23

1-benzyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

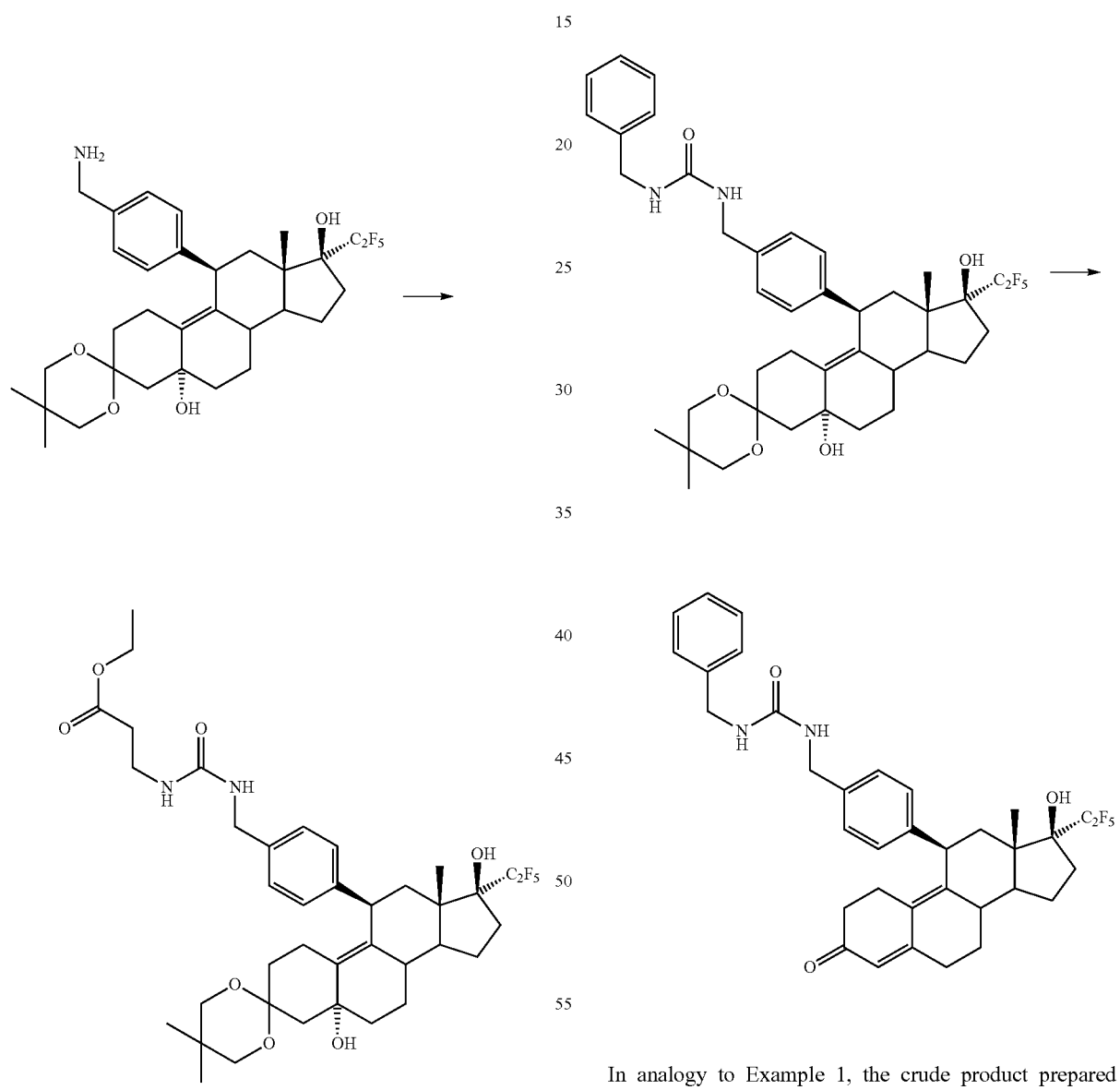

In analogy to Example 17a, 40 mg (67 µmol) of the compound prepared according to Example 17b were converted using ethyl 3-isocyanatopropionate. The crude product isolated after workup was converted further without purification.

In analogy to Example 1, the crude product prepared according to Example 23a was converted and, after workup and purification, 19.1 mg (45%) of the title compound were isolated as a colourless foam.

$^1$H NMR (CDCl$_3$): δ=0.56 (3H), 1.38-1.55 (2H), 1.71-1.87 (3H), 2.05 (1H), 2.13-2.63 (10H), 2.69 (1H), 4.21-4.36 (4H), 4.40 (1H), 4.80-4.89 (2H), 5.75 (1H), 7.09 (2H), 7.14 (2H), 7.20-7.33 (5H) ppm.

EXAMPLE 23a 1-benzyl-3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]urea

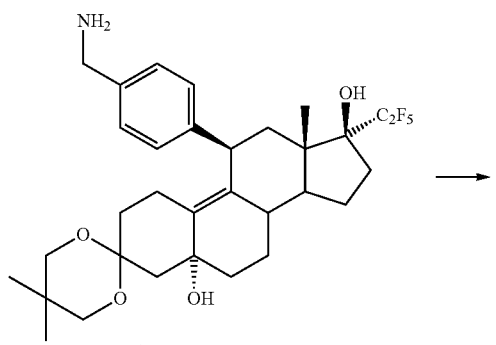

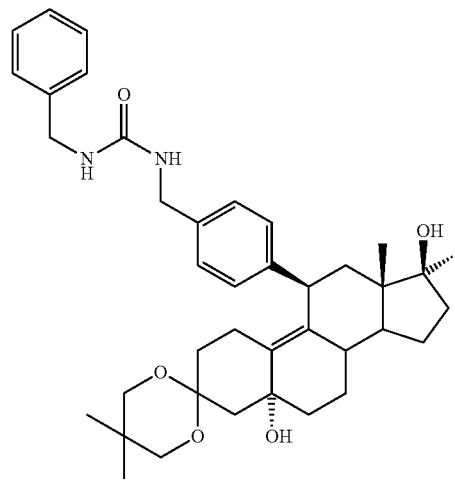

In analogy to Example 17a, 40 mg (67 μmol) of the compound prepared according to Example 17b were converted using benzyl isocyanate. The crude product isolated after workup was converted further without purification.

EXAMPLE 24

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-phenyl urea

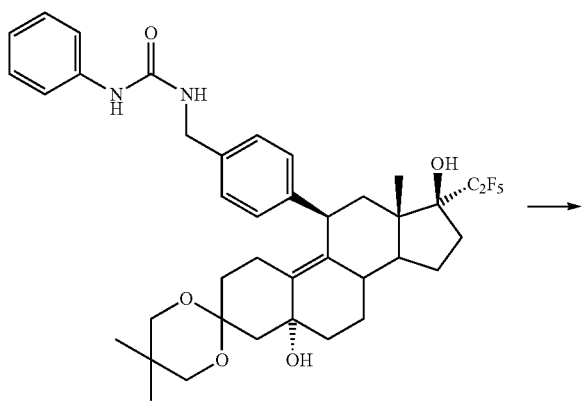

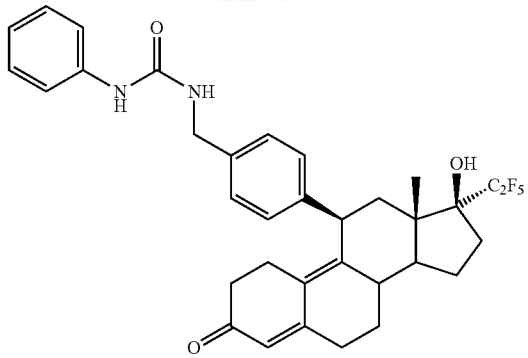

In analogy to Example 1, the crude product prepared according to Example 24a was converted and, after workup and purification, 18.7 mg (46%) of the title compound were isolated as a colourless foam.

$^1$H NMR (CDCl$_3$): δ=0.54 (3H), 1.37-1.54 (2H), 1.70-1.87 (3H), 2.03 (1H), 2.11-2.61 (9H), 2.66 (1H), 2.82 (1H), 4.20-4.43 (3H), 5.58 (1H), 5.75 (1H), 7.00 (1H), 7.07 (2H), 7.14 (2H), 7.21-7.30 (5H) ppm.

EXAMPLE 24a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-phenylurea

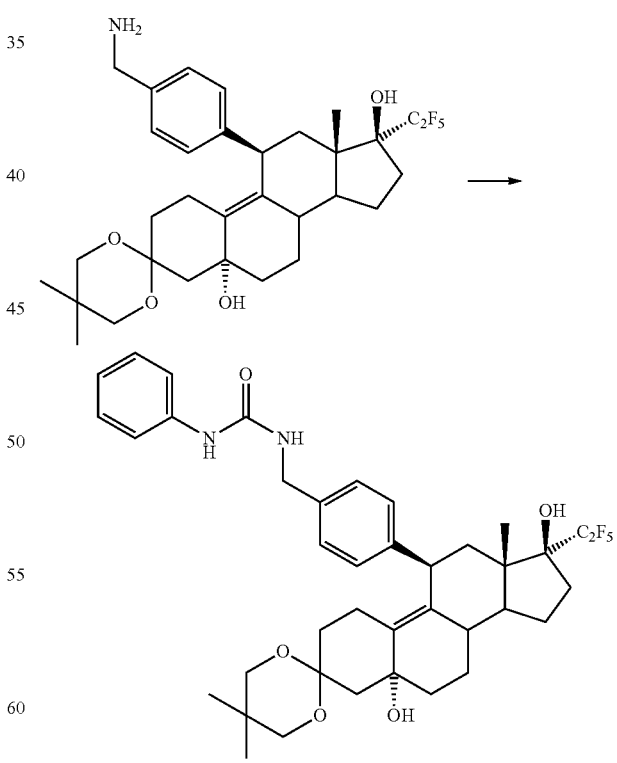

In analogy to Example 17a, 40 mg (67 μmol) of the compound prepared according to Example 17b were converted using phenyl isocyanate. The crude product isolated after workup was converted further without purification.

EXAMPLE 25

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-p-tolylurea

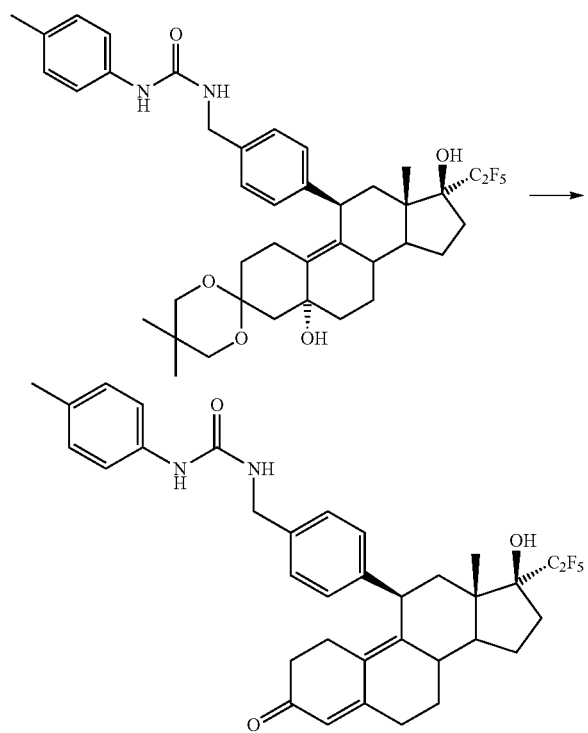

In analogy to Example 1, the crude product prepared according to Example 25a was converted and, after workup and purification, 14.6 mg (35%) of the title compound were isolated as a colourless foam.

$^1$H NMR (CD$_3$OD): δ=0.58 (3H), 1.35-1.57 (2H), 1.69-1.84 (3H), 2.09 (1H), 2.15-2.47 (5H), 2.25 (3H), 2.53-2.73 (4H), 2.79 (1H), 4.33 (2H), 4.51 (1H), 5.73 (1H), 7.04 (2H), 7.17-7.28 (6H) ppm.

EXAMPLE 25a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-p-tolylurea

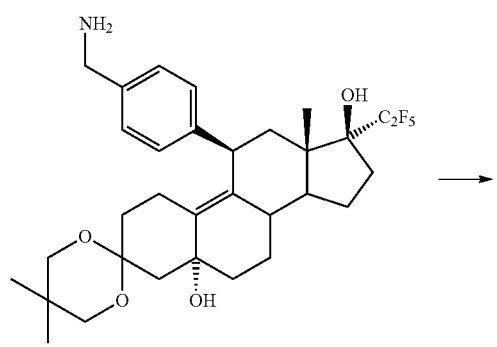

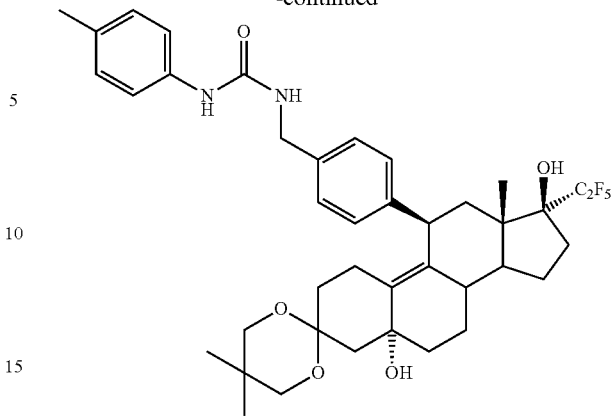

In analogy to Example 17a, 40 mg (67 μmol) of the compound prepared according to Example 17b were converted using 4-tolyl isocyanate. The crude product isolated after workup was converted further without purification.

EXAMPLE 26

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}acetic acid

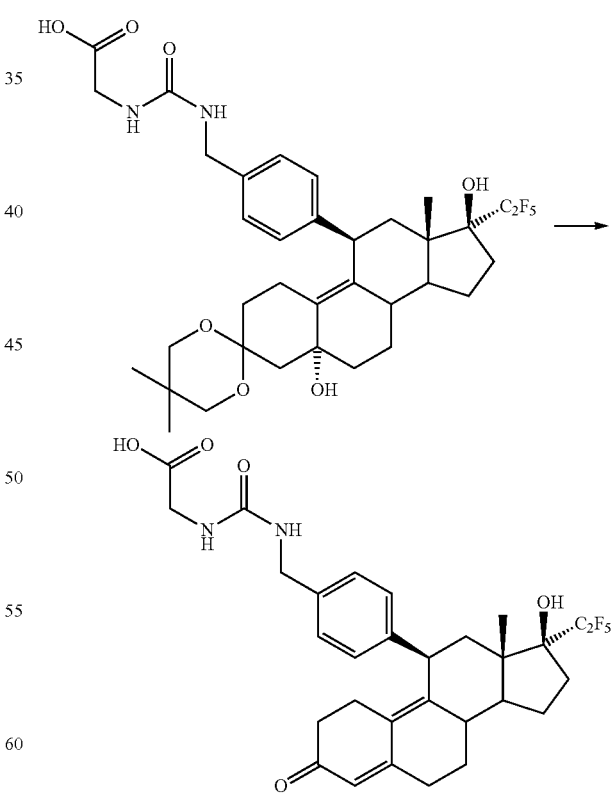

In analogy to Example 1, 58 mg (83 μmol) of the compound prepared according to Example 26a were converted and, after workup and purification, 22 mg (45%) of the title compound were isolated as a colourless foam.

$^1$H NMR (CD$_3$OD): δ=0.57 (3H), 1.36-1.54 (2H), 1.70-1.82 (3H), 2.09 (1H), 2.16-2.46 (5H), 2.55-2.72 (4H), 2.79 (1H), 3.70 (2H), 4.26 (2H), 4.50 (1H), 5.73 (1H), 7.17 (2H), 7.22 (2H) ppm.

EXAMPLE 26a

{3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]ureido}acetic acid

EXAMPLE 27

3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}propionic acid

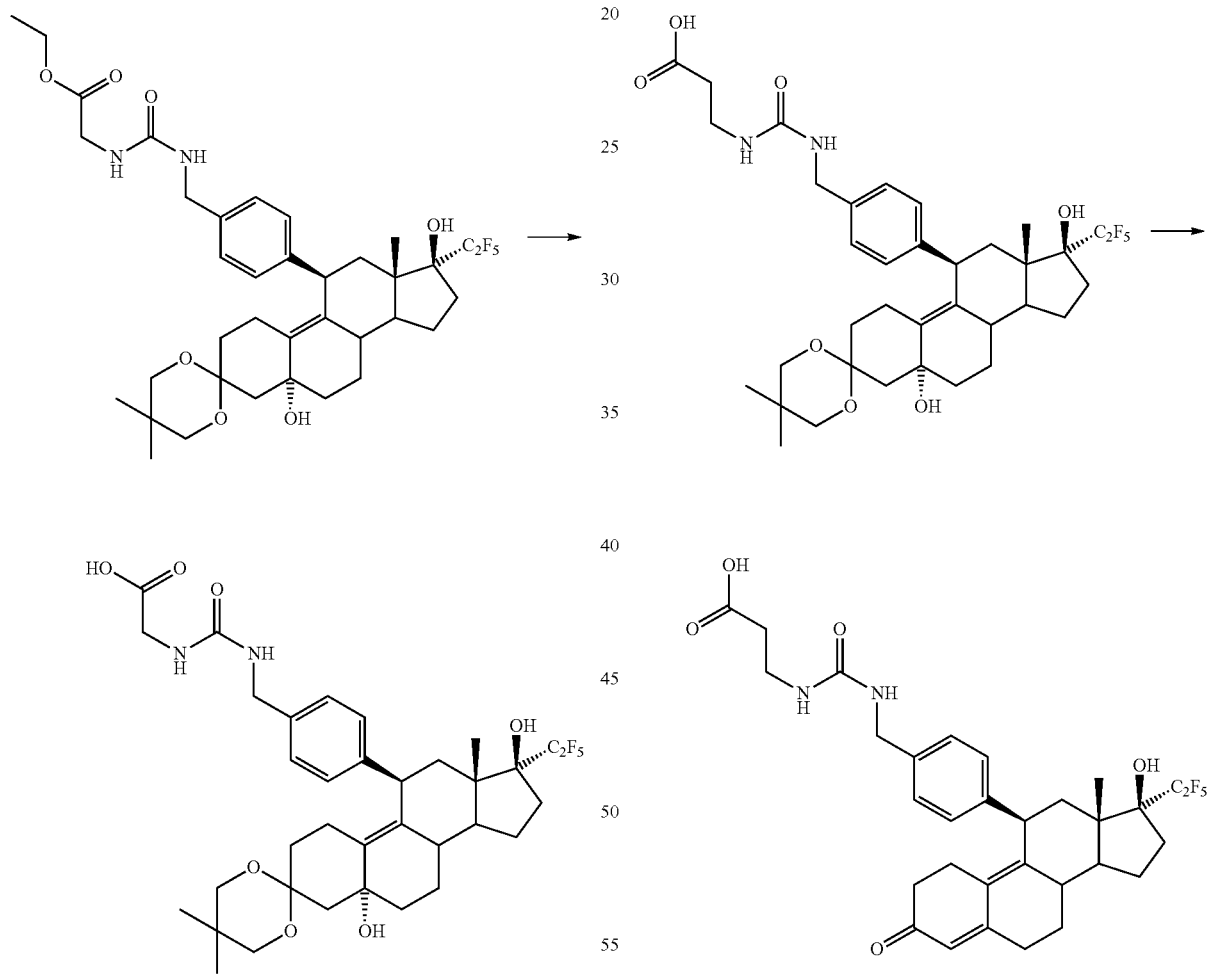

The solution of 85 mg (120 μmol) of the compound prepared according to Example 21a in a mixture of 1 ml of tetrahydrofuran and 1 ml of ethanol was admixed with 1 ml of a 5% aqueous lithium hydroxide solution and stirred at 23° C. for 3 hours. The mixture was diluted with water, acidified by adding 1 molar hydrochloric acid, saturated with sodium chloride and extracted repeatedly with diethyl ether, and the combined organic extracts were dried over sodium sulphate. After filtration and removal of solvent, 64 mg (78%) of the title compound were isolated as a colourless foam.

In analogy to Example 1, 62 mg (87 μmol) of the compound prepared according to Example 27a were converted and, after workup and purification, 22 mg (42%) of the title compound were isolated as a colourless foam.

$^1$H NMR (CD$_3$OD): δ=0.57 (3H), 1.36-1.54 (2H), 1.70-1.82 (3H), 2.09 (1H), 2.16-2.45 (7H), 2.55-2.71 (4H), 2.79 (1H), 3.35 (2H), 4.24 (2H), 4.49 (1H), 5.73 (1H), 7.18 (4H) ppm.

EXAMPLE 27a

3-{3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]ureido}propionic acid

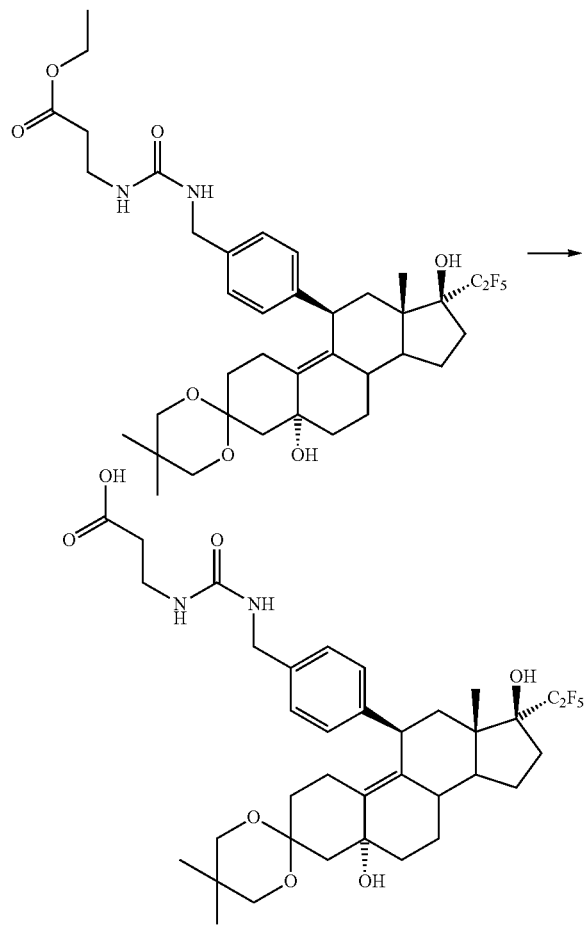

In analogy to Example 26a, 87 mg (120 µmol) of the compound prepared according to Example 22a were converted and, after workup, 68 mg (81%) of the title compound were isolated as a colourless foam.

EXAMPLE 28

(8S,11R,13S,14S,17S)-11-(4-azidomethylphenyl)-17-hydroxy-13-methyl-17-pentafluoroethyl-1,2,6,7,8,11,12,13,14,15,16,17-dodecahydrocyclopenta[a]phenanthren-3-one

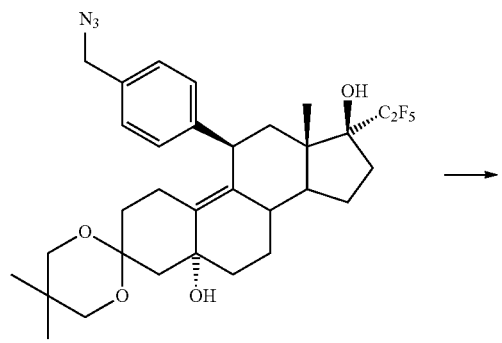

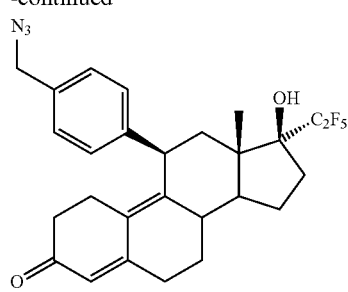

In analogy to Example 1, 50 mg (80 µmol) of the compound prepared according to Example 17c were converted and, after workup and purification, 26.6 mg (64%) of the title compound were isolated as a colourless foam.

$^1$H NMR (CDCl$_3$): δ=0.58 (3H), 1.39-1.58 (2H), 1.72-1.88 (3H), 2.00-2.16 (2H), 2.20-2.66 (9H), 2.74 (1H), 4.31 (2H), 4.46 (1H), 5.79 (1H), 7.16 (2H), 7.24 (2H) ppm.

EXAMPLE 29

(8S,11R,13S,14S,17S)-17-hydroxy-13-methyl-17-pentafluoroethyl-11-[4'-(1H-tetrazol-5-yl)biphenyl-4-yl]-1,2,6,7,8,11,12,13,14,15,16,17-dodecahydrocyclopenta[a]phenanthren-3-one

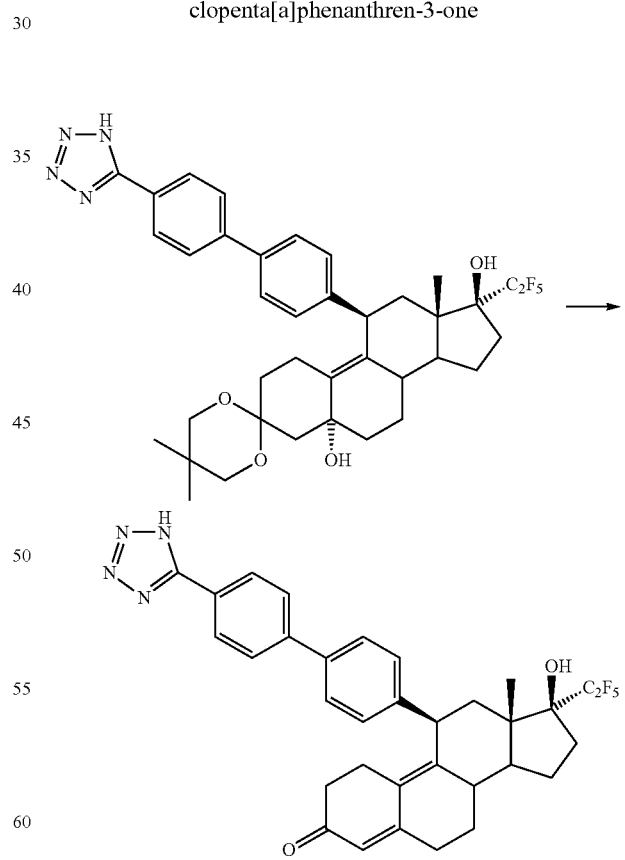

In analogy to Example 1, 63 mg (88 µmol) of the compound prepared according to Example 29a were converted and, after workup and purification, 18 mg (34%) of the title compound were isolated as a colourless foam.

$^1$H NMR (CD$_3$OD): δ=0.65 (3H), 1.39-1.60 (2H), 1.72-1.85 (3H), 2.11 (1H), 2.24-2.49 (5H), 2.58-2.77 (4H), 2.85 (1H), 4.58 (1H), 5.75 (1H), 7.34 (2H), 7.62 (2H), 7.69 (2H), 8.07 (2H) ppm.

EXAMPLE 29a (5R,8S,11R,13S,14S,17S)-5',5',13-trimethyl-17-pentafluoroethyl-11-[4'-(1H-tetrazol-5-yl)biphenyl-4-yl]-2,3,4,6,7,8,11,12,13,14,15,16,17-tetradecahydro-1H-spiro[cyclopenta[a]phenanthrene-3,2'-[1,3]dioxane]-5,17-diol

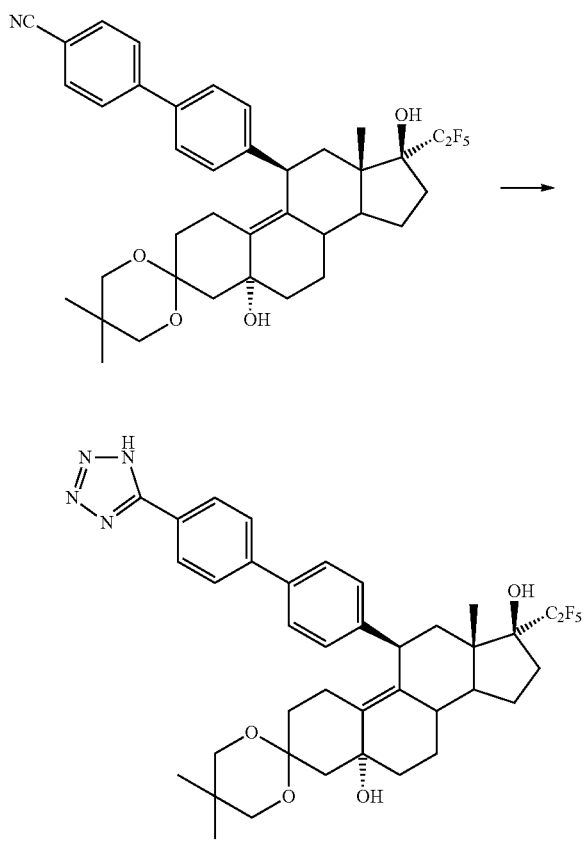

The suspension of 300 mg (0.45 mmol) of (5R,8S,11R,13S,14S,17S)-5',5',13-trimethyl-17-pentafluoroethyl-11-[4'-cyanobiphenyl-4-yl]-2,3,4,6,7,8,11,12,13,14,15,16,17-tetradecahydro-1H-spiro[cyclopenta[a]phenanthrene-3,2'-[1,3]dioxane]-5,17-diol, which was prepared by the process described in DE 19706061, 570 mg of sodium azide, 15 mg of ammonium chloride and 6 ml of dimethylformamide was heated at a bath temperature of 150° C. for 16 hours. The mixture was concentrated, taken up in a 1:1 mixture of dichloromethane and ethanol, and filtered through Celite, and the concentrated filtrate was purified by chromatography. 63 mg (20%) of the title compound were isolated as a colourless foam.

EXAMPLE 30

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzonitrile

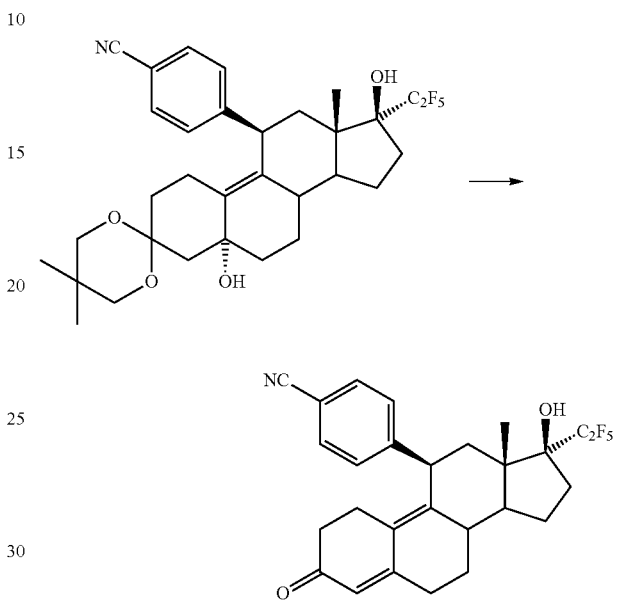

In analogy to Example 1, 50 mg (84 μmol) of the compound prepared according to Example 30a were converted and, after workup and purification, 24 mg (58%) of the title compound were isolated as a colourless foam.

$^1$H NMR (CDCl$_3$): δ=0.55 (3H), 1.40-1.56 (2H), 1.74-1.89 (3H), 2.08 (1H), 2.16 (1H), 2.17-2.65 (9H), 2.71 (1H), 4.48 (1H), 5.81 (1H), 7.32 (2H), 7.59 (2H) ppm.

EXAMPLE 30a 4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)benzonitrile

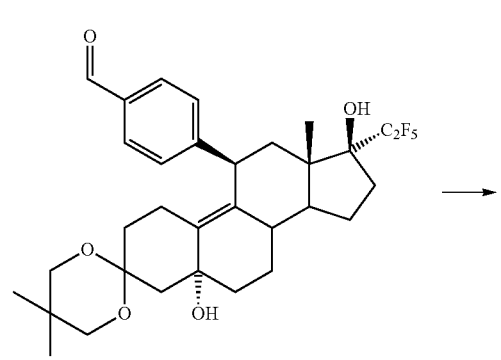

-continued

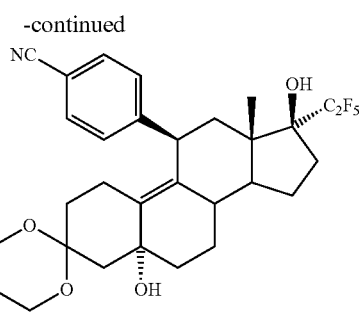

The suspension of 505 mg (0.84 mmol) of the compound prepared according to Example 2c in 2.6 ml of a 25% aqueous ammonia solution was admixed with 10 ml of tetrahydrofuran, 669 mg of iodine, and heated at a bath temperature of 60° C. for 21 hours. It was extracted with ethyl acetate, washed with water, a semisaturated sodium thiosulphate solution, saturated sodium chloride solution, and dried over sodium sulphate. The residue obtained after filtration and removal of solvent was purified by chromatography on silica gel. 434 mg (86%) of the title compound were isolated as a colourless foam.

EXAMPLE 31

(8S,11R,13S,14S,17S)-17-hydroxy-13-methyl-17-pentafluoroethyl-11-[4-(1H-tetrazol-5-yl)phenyl]-1,2,6,7,8,11,12,13,14,15,16,17-dodecahydrocyclopenta[a]phenanthren-3-one

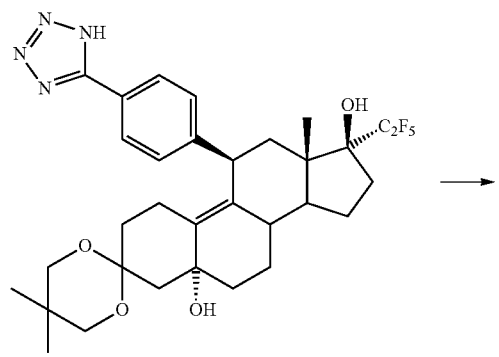

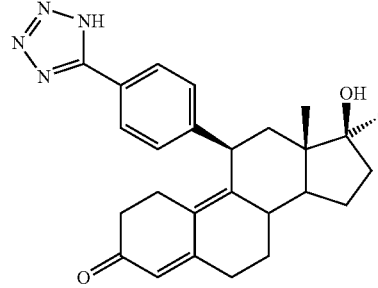

In analogy to Example 1, 26 mg (41 μmol) of the compound prepared according to Example 31a were converted and, after workup and purification, 8.1 mg (37%) of the title compound were isolated as a colourless foam.

$^1$H NMR (CD$_3$OD): δ=0.64 (3H), 1.38-1.60 (2H), 1.71-1.86 (3H), 2.12 (1H), 2.22-2.49 (5H), 2.56-2.79 (4H), 2.85 (1H), 4.58 (1H), 5.76 (1H), 7.34 (2H), 7.94 (2H) ppm.

EXAMPLE 31a (5R,8S,11R,13S,14S,17S)-5',5',13-trimethyl-17-pentafluoroethyl-11-[4-(1H-tetrazol-5-yl)phenyl]-2,3,4,6,7,8,11,12,13,14,15,16,17-tetradecahydro-1H-spiro[cyclopenta[a]phenanthrene-3,2'-[1,3]dioxane]-5,17-diol

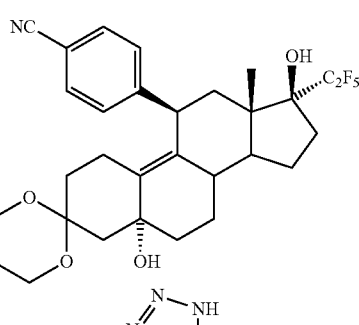

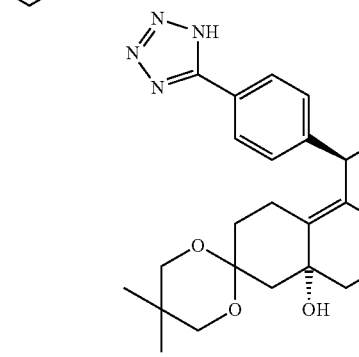

In analogy to Example 29a, 100 mg (0.17 mmol) of the compound prepared according to Example 30a were converted and, after workup and purification, 27 mg (25%) of the title compound were isolated as a colourless foam.

EXAMPLE 32

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-(4-methoxyphenyl)urea

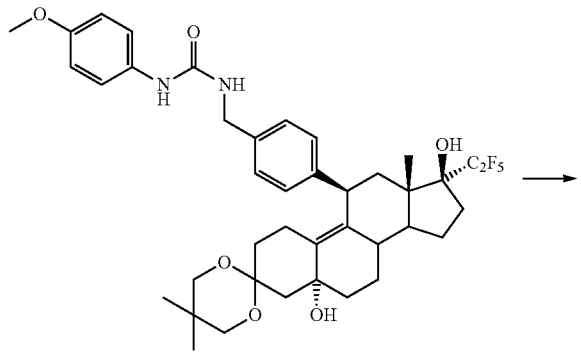

-continued

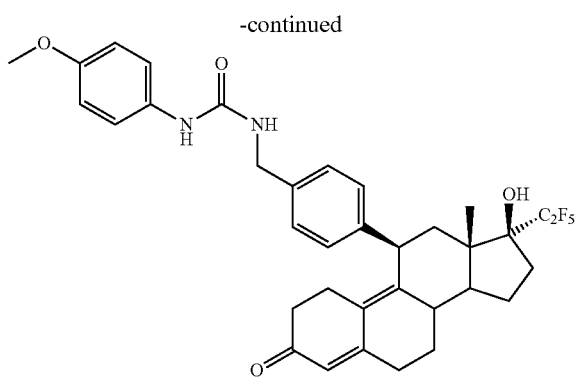

In analogy to Example 1, 50 mg (67 μmol) of the compound prepared according to Example 32a were converted and, after workup and purification, 21 mg (49%) of the title compound were isolated as a colourless foam.

$^1$H NMR (CDCl$_3$): δ=0.56 (3H), 1.37-1.54 (2H), 1.72-1.86 (3H), 2.04 (1H), 2.15-2.62 (9H), 2.66 (1H), 2.70 (1H), 3.77 (3H), 4.34 (2H), 4.40 (1H), 5.19 (1H), 5.76 (1H), 6.49 (1H), 6.82 (2H), 7.06-7.19 (6H) ppm.

EXAMPLE 32a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-(4-methoxyphenyl)urea

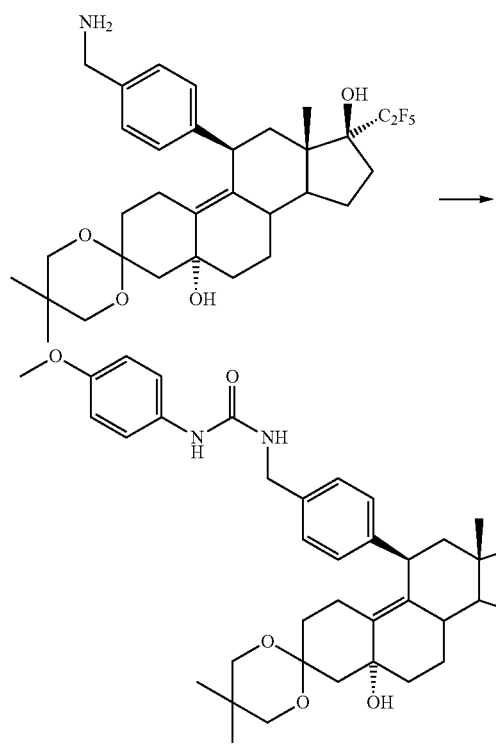

The solution of 40 mg (67 μmol) of the compound prepared according to Example 17b in 1 ml of dichloromethane was admixed with 9 μl of 4-methoxyphenyl isocyanate and stirred at 23° C. for 2 hours. The mixture was concentrated and the resulting residue was converted further without purification.

EXAMPLE 33

1-(4-fluorophenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

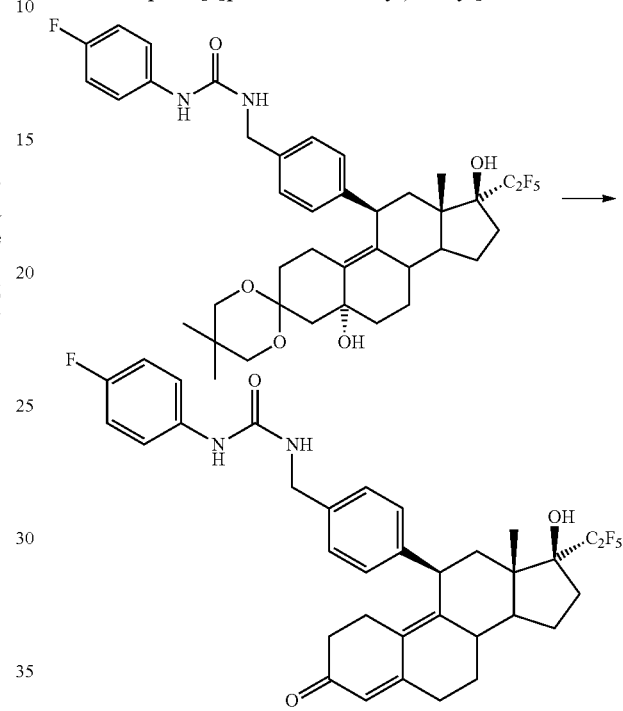

In analogy to Example 1, 49 mg (67 μmol) of the compound prepared according to Example 33a were converted and, after workup and purification, 21 mg (50%) of the title compound were isolated as a colourless foam.

$^1$H NMR (CDCl$_3$): δ=0.54 (3H), 1.36-1.54 (2H), 1.71-1.88 (3H), 2.04 (1H), 2.10-2.72 (10H), 2.88 (1H), 4.27 (2H), 4.39 (1H), 5.59 (1H), 5.75 (1H), 6.90 (2H), 7.02-7.24 (7H) ppm.

EXAMPLE 33a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-(4-fluorophenyl)urea

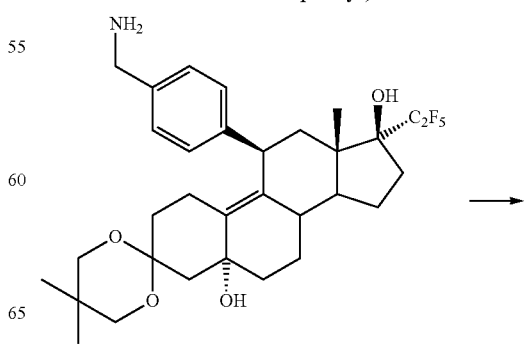

-continued

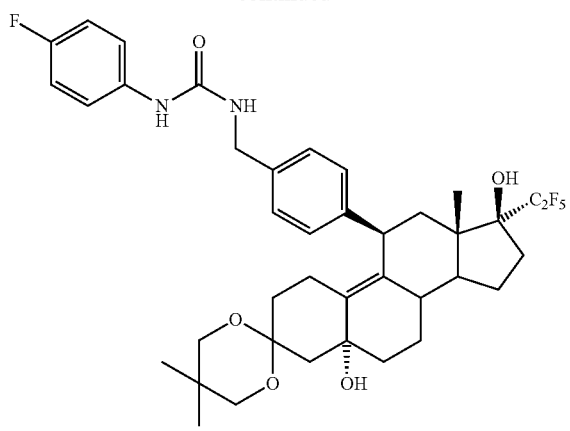

In analogy to Example 32a, 40 mg (67 μmol) of the compound prepared according to Example 17b were converted using 4-fluorophenyl isocyanate and, after workup, 50 mg of the title compound were isolated as a crude product.

EXAMPLE 34

1-(4-chlorophenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

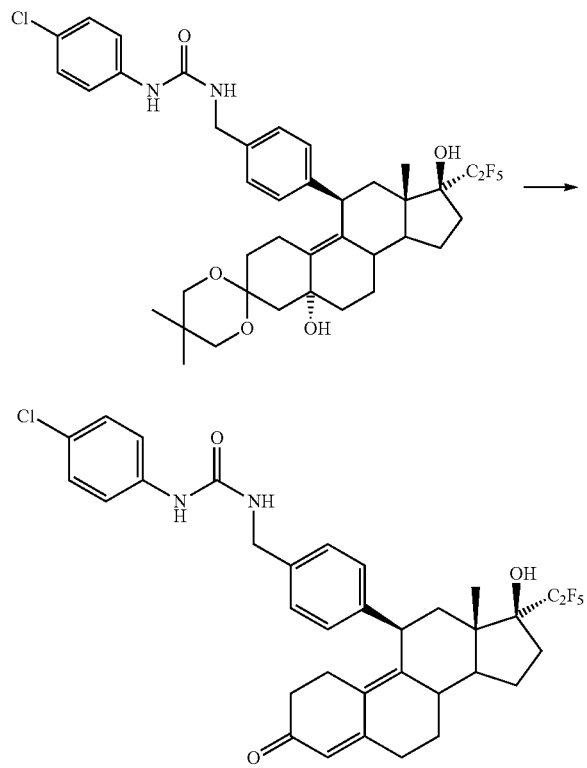

In analogy to Example 1, 50 mg (66 μmol) of the compound prepared according to Example 34a were converted and, after workup and purification, 21 mg (50%) of the title compound were isolated as a colourless foam.

$^1$H NMR (CDCl$_3$): δ=0.51 (3H), 1.34-1.51 (2H), 1.67-1.82 (3H), 2.01 (1H), 2.10-2.61 (11H), 2.67 (1H), 4.30 (2H), 4.37 (1H), 5.73 (1H), 7.02-7.29 (9H) ppm.

EXAMPLE 34a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-(4-chlorophenyl)urea

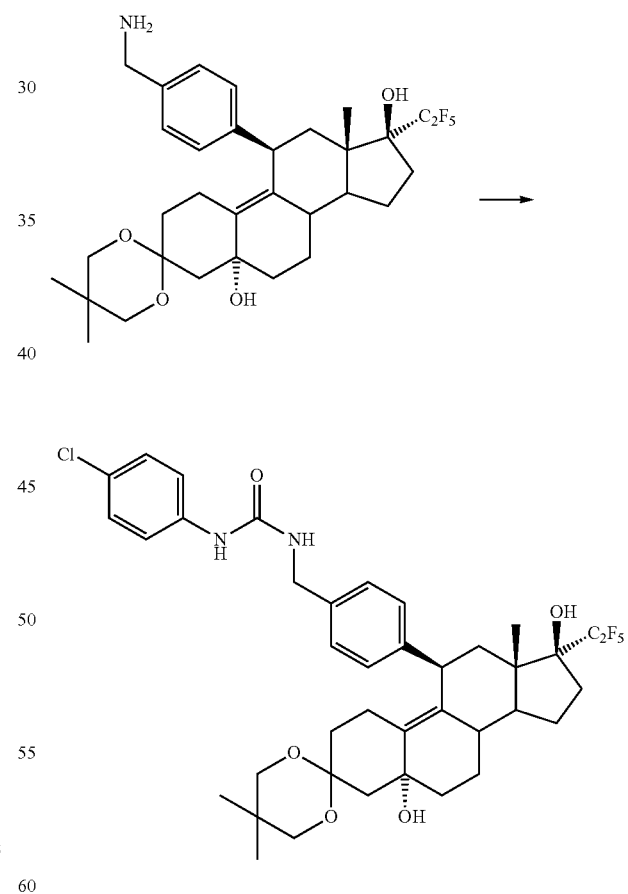

In anlogy to Example 32a, 40 mg (67 μmol) of the compound prepared according to Example 17b were converted using 4-chlorophenyl isocyanate and, after workup, 51 mg of the title compound were isolated as a crude product.

EXAMPLE 35

1-(4-tert-butylphenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

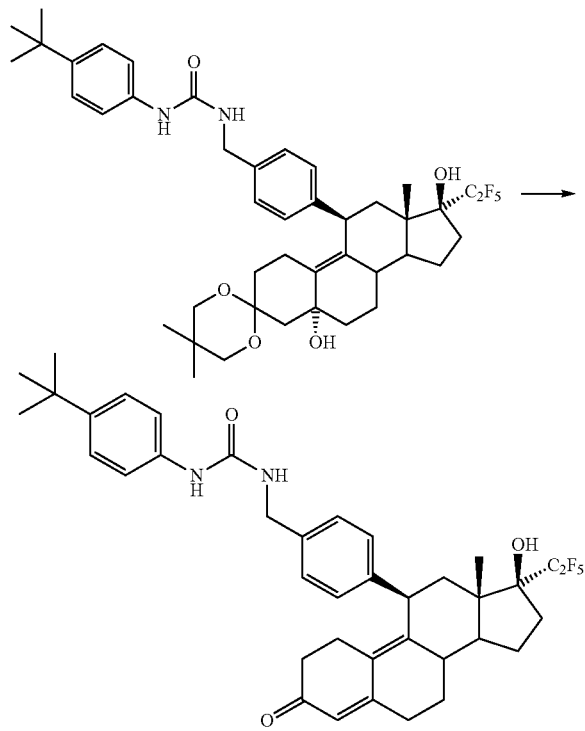

In analogy to Example 1, 51 mg (66 μmol) of the compound prepared according to Example 35a were converted and, after workup and purification, 20.5 mg (46%) of the title compound were isolated as a colourless foam.

$^1$H NMR (CDCl$_3$): δ=0.56 (3H), 1.28 (9H), 1.37-1.55 (2H), 1.71-1.87 (3H), 2.05 (1H), 2.15-2.62 (9H), 2.65 (1H), 2.69 (1H), 4.33 (2H), 4.40 (1H), 5.37 (1H), 5.76 (1H), 6.64 (1H), 7.09 (2H), 7.13-7.21 (4H), 7.30 (2H) ppm.

EXAMPLE 35a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-(4-tert-butylphenyl)urea

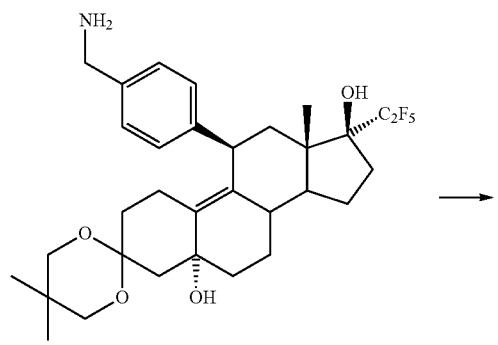

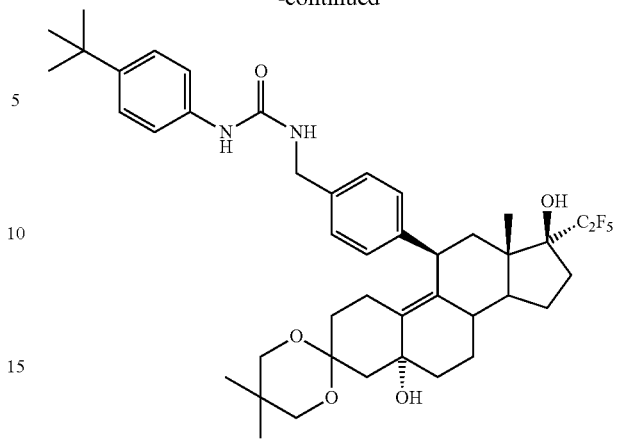

In analogy to Example 32a, 40 mg (67 μmol) of the compound prepared according to Example 17b were converted using 4-tert-butylphenyl isocyanate and, after workup, 52 mg of the title compound were isolated as a crude product.

EXAMPLE 36

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}benzoic acid ethyl ester

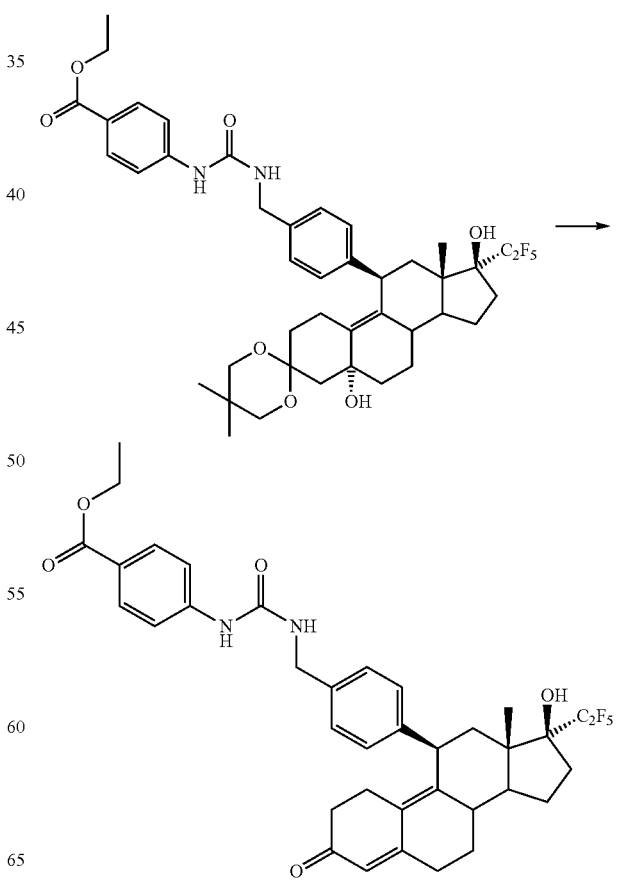

In analogy to Example 1, 67 mg (85 μmol) of the compound prepared according to Example 36a were converted and, after workup and purification, 21 mg (37%) of the title compound were isolated as a colourless foam.

$^1$H NMR (CDCl$_3$): δ=0.58 (3H), 1.36 (3H), 1.39-1.54 (2H), 1.71-1.87 (3H), 1.98-2.22 (3H), 2.27-2.70 (8H), 3.25 (1H), 4.27-4.42 (5H), 5.75 (1H), 6.08 (1H), 7.08 (2H), 7.15 (2H), 7.36 (2H), 7.84 (2H), 7.90 (1H) ppm.

EXAMPLE 36a

{3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]ureido}-4-benzoic acid ethyl ester

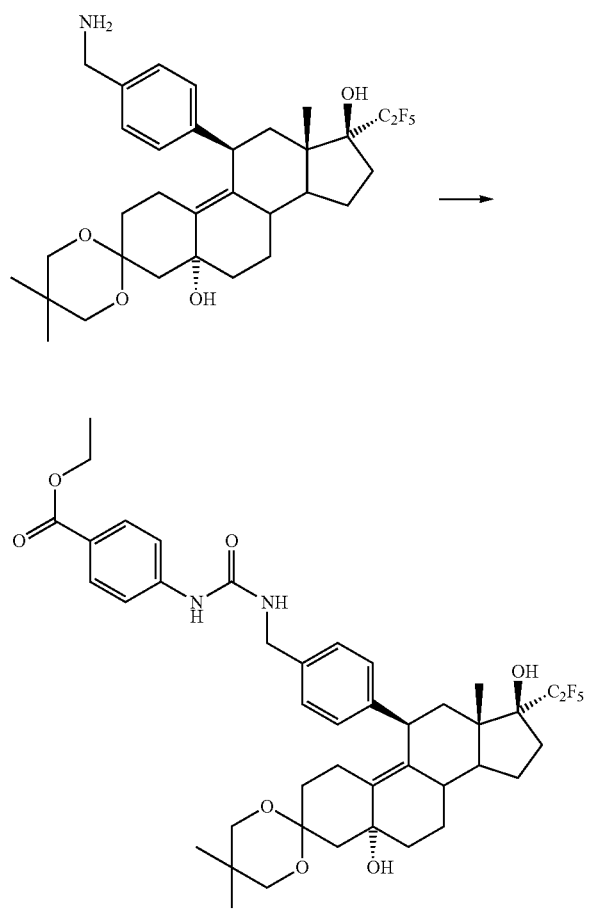

In analogy to Example 32a, 100 mg (0.17 mmol) of the compound prepared according to Example 17b were converted using ethyl 4-isocyanatobenzoate and, after workup, 137 mg of the title compound were isolated as a crude product.

EXAMPLE 37

1-[4-(3,5-dimethylisoxazol-4-yl)phenyl]-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

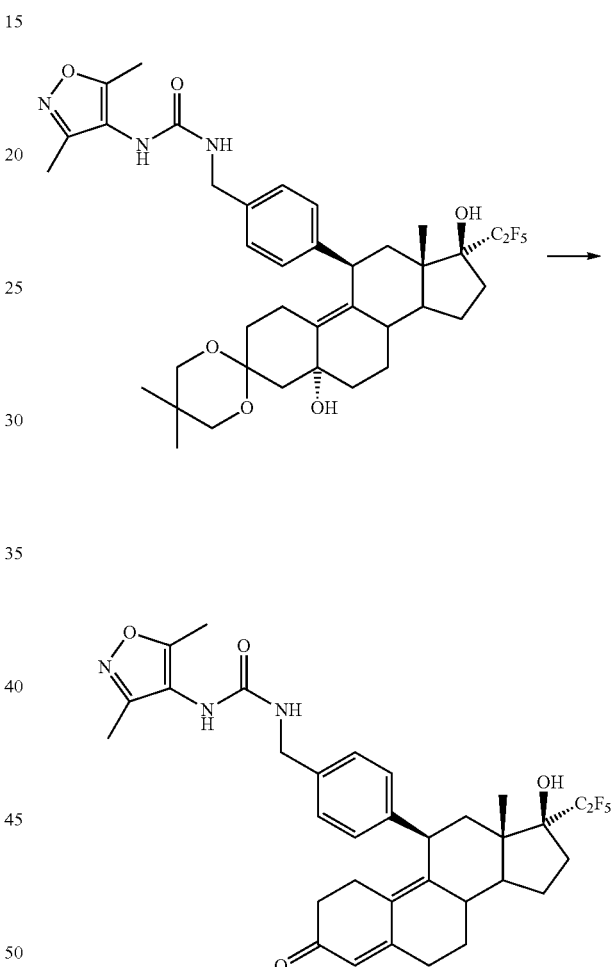

In analogy to Example 1, 49 mg (66 μmol) of the compound prepared according to Example 37a were converted and, after workup and purification, 9.1 mg (22%) of the title compound were isolated as a colourless foam.

$^1$H NMR (CDCl$_3$): δ=0.52 (3H), 1.34-1.53 (2H), 1.68-1.83 (3H), 1.98-2.13 (4H), 2.10 (3H), 2.22-2.62 (9H), 2.27 (3H), 2.69 (1H), 4.30 (2H), 4.39 (1H), 5.75 (1H), 7.05-7.16 (4H) ppm.

EXAMPLE 37a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-(3,5-dimethyl isoxazol-4-yl)urea

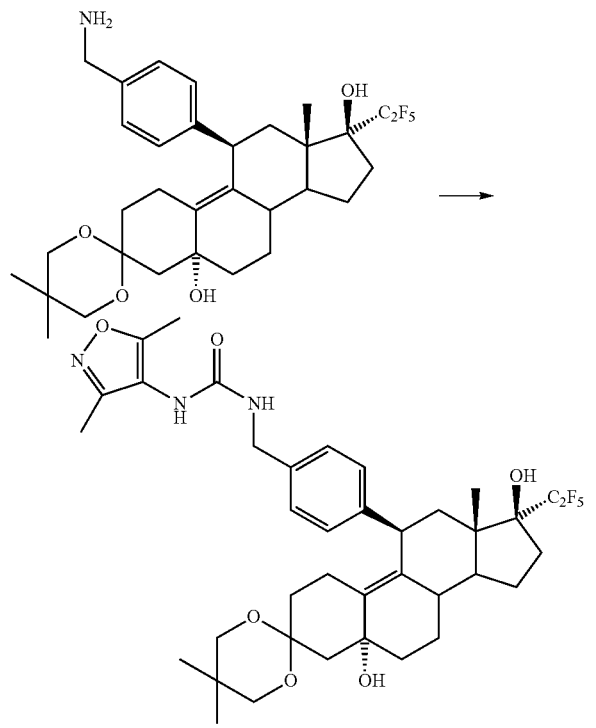

In analogy to Example 32a, 40 mg (67 μmol) of the compound prepared according to Example 17b were converted using 3,5-dimethylisoxazol-4-yl isocyanate and, after workup, 50 mg of the title compound were isolated as a crude product.

EXAMPLE 38

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}benzoic acid

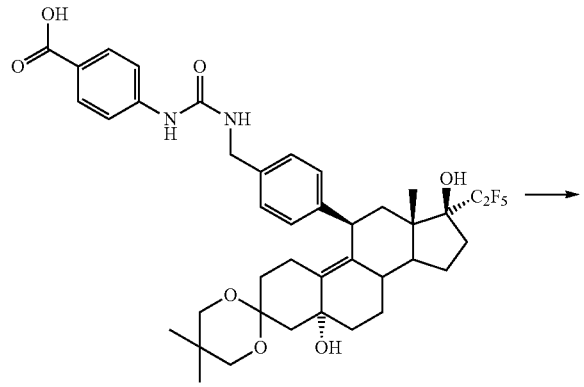

In analogy to Example 1, 71 mg (93 μmol) of the compound prepared according to Example 38a were converted and, after workup and purification, 15 mg (26%) of the title compound were isolated as a colourless foam.

$^1$H NMR (CD$_3$OD): δ=0.57 (3H), 1.25-1.56 (2H), 1.68-1.83 (3H), 2.02-2.46 (6H), 2.53-2.72 (4H), 2.79 (1H), 4.34 (2H), 4.50 (1H), 5.72 (1H), 7.20 (2H), 7.25 (2H), 7.41 (2H), 7.87 (2H) ppm.

EXAMPLE 38a

{3-[4-((5R,8S,11R,13S,14S,17S)-5,17-dihydroxy-17-pentafluoroethyl-5'5,13-trimethyl-1,2,3,4,6,7,8,11,12,13,14,15,16,17-tetradecahydrospiro[cyclopenta[a]phenanthrene-3,2'-[1,3]dioxan]-11-yl)benzyl]ureido}-4-benzoic acid

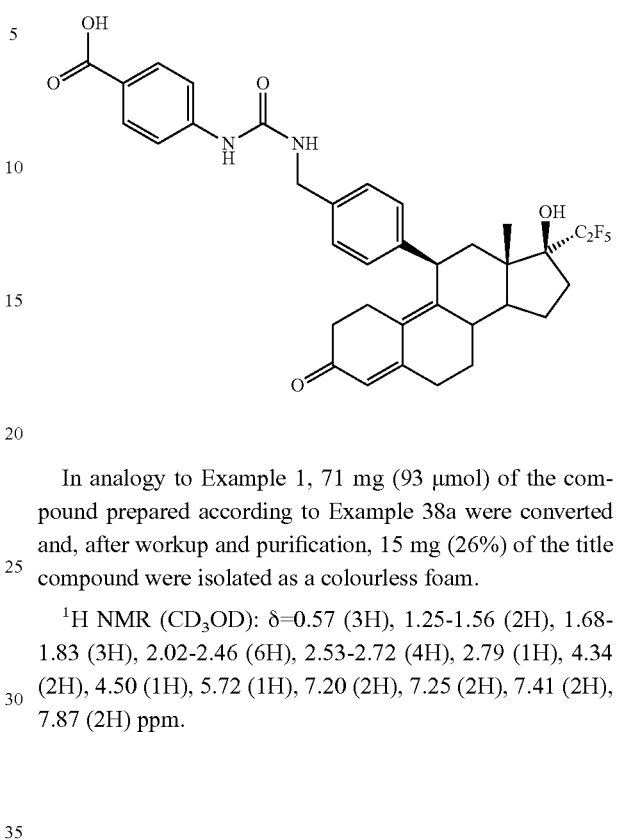

-continued

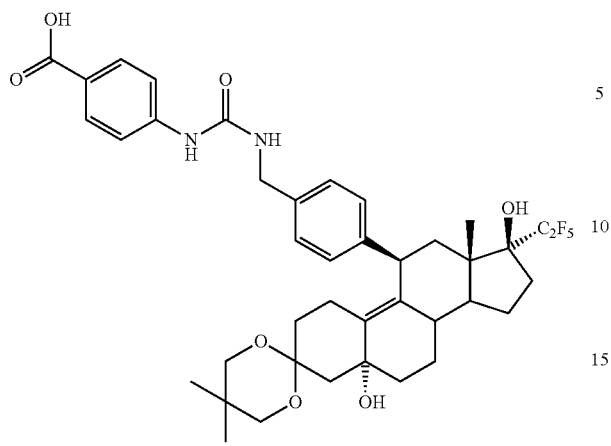

In analogy to Example 26a, 69 mg (87 μmol) of the compound prepared according to Example 36a were converted and, after workup, 71 mg of the title compound were isolated as a crude product.

EXAMPLE 39

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-(4-piperidin-1-ylphenyl)urea

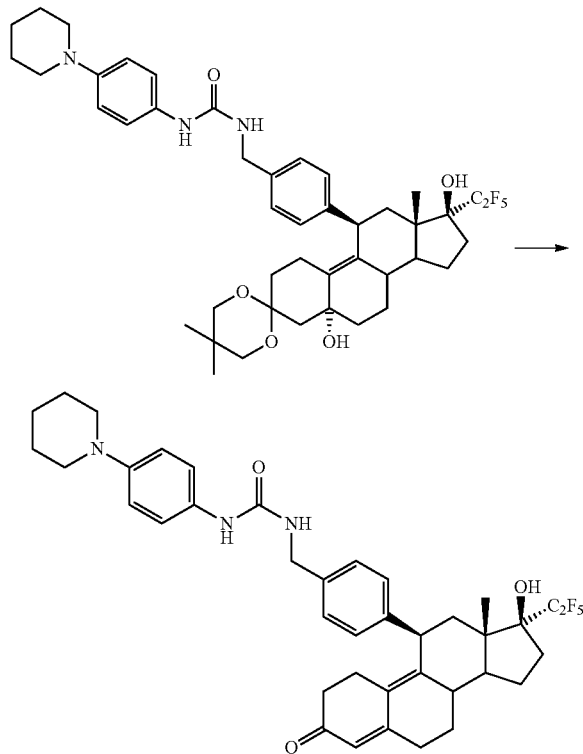

In analogy to Example 1, 27 mg (34 μmol) of the compound prepared according to Example 39a were converted and, after workup and purification, 9.8 mg (42%) of the title compound were isolated as a colourless foam.

$^1$H NMR (CDCl$_3$): δ=0.55 (3H), 1.37-1.86 (11H), 2.04 (1H), 2.16-2.62 (9H), 2.70 (1H), 2.79 (1H), 3.10 (4H), 4.33 (2H), 4.40 (1H), 5.15 (1H), 5.76 (1H), 6.37 (1H), 6.86 (2H), 7.05-7.17 (6H) ppm.

EXAMPLE 39a

1-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl]-3-(4-piperidin-1-ylphenyl)urea

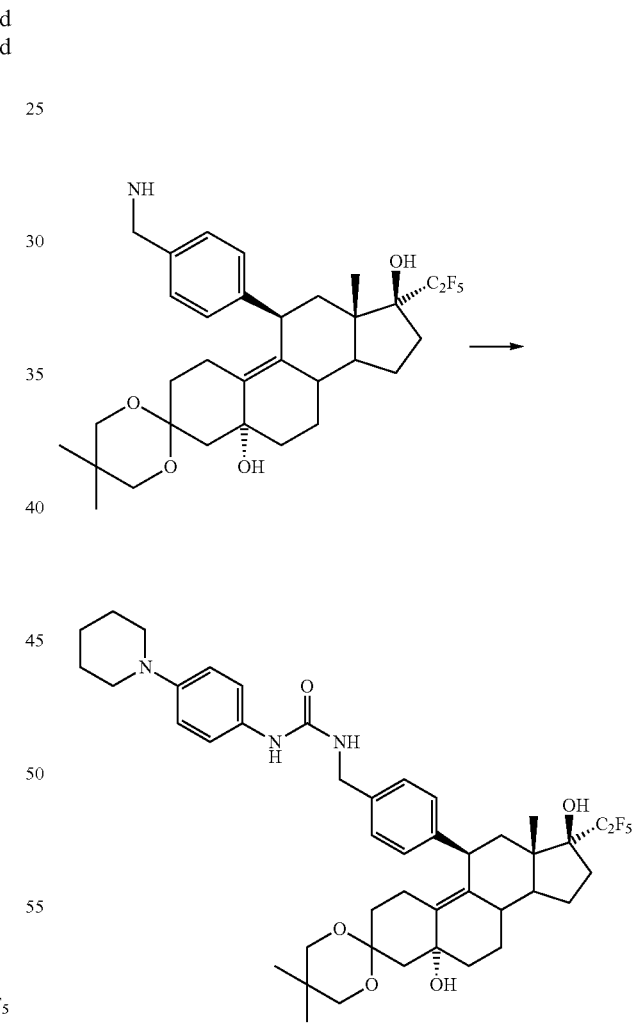

In analogy to Example 32a, 40 mg (67 μmol) of the compound prepared according to Example 17b were converted using 4-piperidinylphenyl isocyanate and, after workup, 55 mg of the title compound were isolated as a crude product.

EXAMPLE 40

(8S,11R,13S,14S,17S)-17-hydroxy-13-methyl-11-[4-(3-methyloxetan-3-yl)phenyl]-17-pentafluoroethyl-1,2,6,7,8,11,12,13,14,15,16,17-dodecahydrocyclopenta[a]phenanthren-3-one

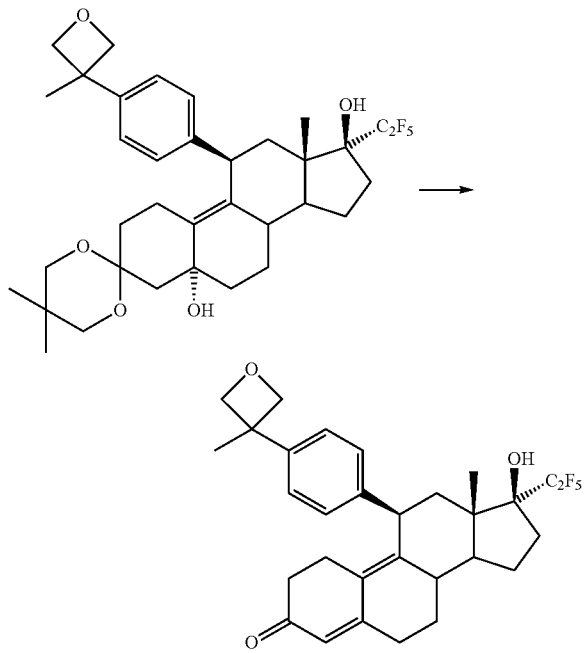

In analogy to Example 1, 59 mg (92 µmol) of the compound prepared according to Example 40a were converted and, after workup and purification, 24 mg (48%) of the title compound were isolated as a colourless foam.

$^1$H NMR (CDCl$_3$): δ=0.60 (3H), 1.40-1.56 (2H), 1.70 (3H), 1.73-1.87 (3H), 2.06 (1H), 2.23-2.63 (10H), 2.75 (1H), 4.44 (1H), 4.63 (2H), 4.91 (2H), 5.78 (1H), 7.15 (4H) ppm.

EXAMPLE 40a (5R,8S,11R,13S,14S,17S)-11-[4-(3-methyloxetan-3-yl)phenyl]-5'5,13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

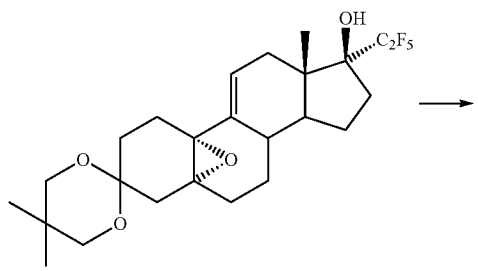

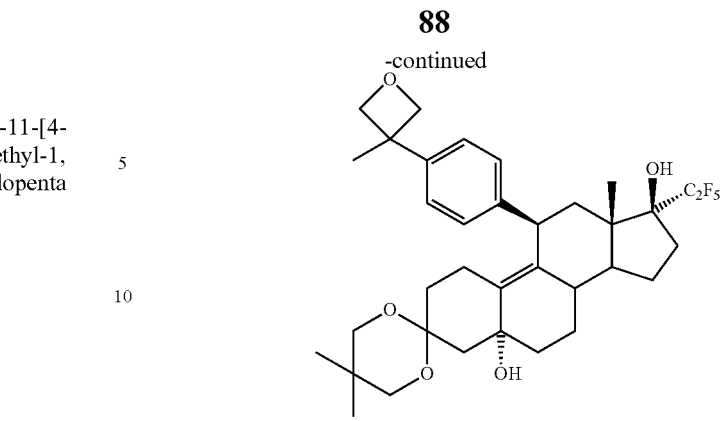

1 ml of a 2 molar solution of isopropylmagnesium chloride in tetrahydrofuran was admixed at 5-10° C. with 1.64 ml of a 2.5 molar solution of n-butyllithium in hexane, and the mixture was stirred at 3° C. for 0.5 hours. The solution of 232 mg of 3-(4-bromophenyl)-3-methyloxetane in 1 ml of tetrahydrofuran was added dropwise and the mixture was stirred at 3° C. for 2 hours. Subsequently, the mixture was admixed with 3 mg of copper(I) chloride and, after 5 minutes, with the solution of 100 mg (0.2 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol, which was prepared by the process described in DE 102006054535, in 1 ml of tetrahydrofuran and the mixture was allowed to warm up to 23° C. within 1.5 hours. It was diluted with ethyl acetate, poured into saturated ammonium chloride solution and admixed with a 25% ammonia solution. The mixture was extracted repeatedly with ethyl acetate, and the combined organic extracts were washed with saturated sodium chloride solution and dried over sodium sulphate. The residue obtained after filtration and solvent removal was purified by chromatography. 59 mg (45%) of the title compound were isolated as a colourless foam.

EXAMPLE 41 ethylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

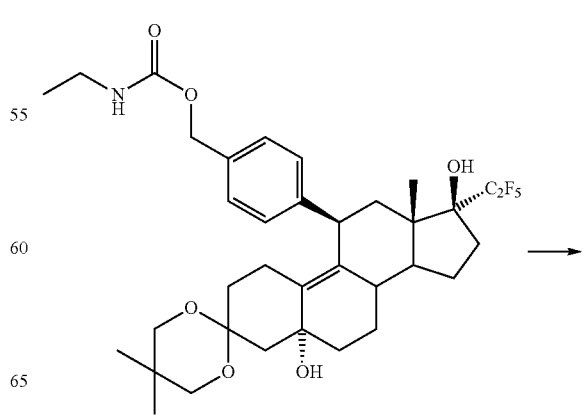

-continued

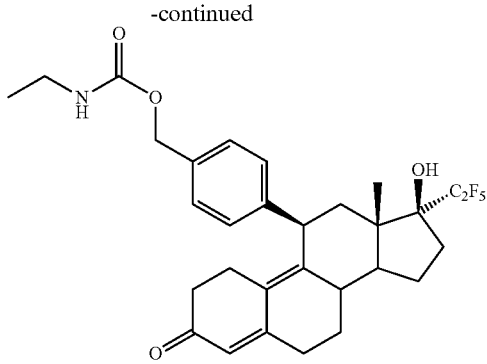

In analogy to Example 1, the crude product prepared in Example 41a was converted and, after workup and purification, 19 mg (50%) of the title compound were isolated as a colourless foam.

$^1$H NMR (CDCl$_3$): δ=0.60 (3H), 1.13 (3H), 1.39-1.57 (2H), 1.73-1.87 (3H), 2.06 (1H), 2.19-2.64 (10H), 2.72 (1H), 3.23 (2H), 4.44 (1H), 4.71 (1H), 5.03 (2H), 5.78 (1H), 7.16 (2H), 7.25 (2H) ppm.

EXAMPLE 41a ethylcarbamic acid 4-((5R,8S,11R,13S,14S,17S)-5,17-dihydroxy-17-pentafluoroethyl-5,5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

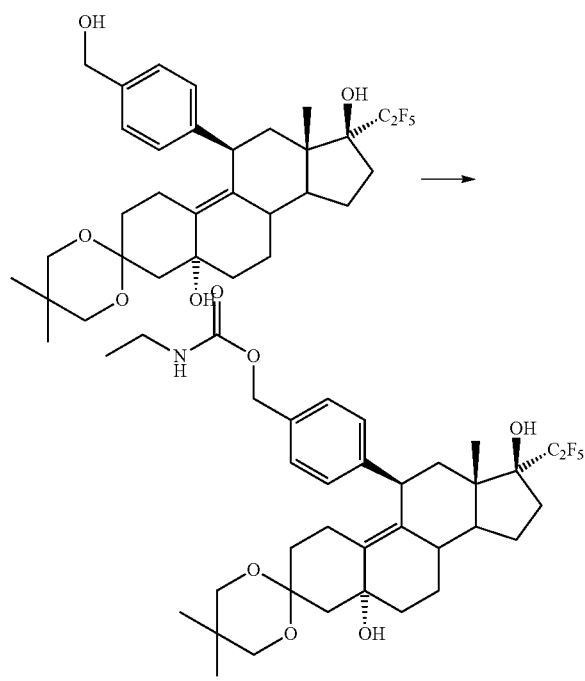

In analogy to Example 32a, 40 mg (67 μmol) of the compound prepared according to Example 17d were converted using ethyl isocyanate and the title compound obtained after workup was converted further as a crude product.

EXAMPLE 42 isopropylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

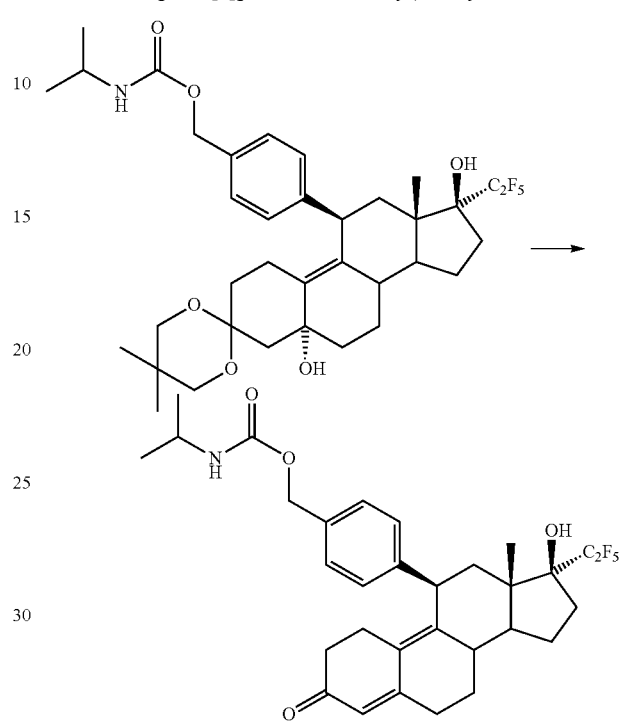

In analogy to Example 1, the crude product prepared in Example 42a was converted and, after workup and purification, 22.3 mg (58%) of the title compound were isolated as a colourless foam.

$^1$H NMR (CDCl$_3$): δ=0.60 (3H), 1.15 (6H), 1.38-1.56 (2H), 1.72-1.87 (3H), 2.06 (1H), 2.20-2.65 (10H), 2.72 (1H), 3.82 (1H), 4.44 (1H), 4.58 (1H), 5.01 (2H), 5.78 (1H), 7.16 (2H), 7.25 (2H) ppm.

EXAMPLE 42a isopropylcarbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

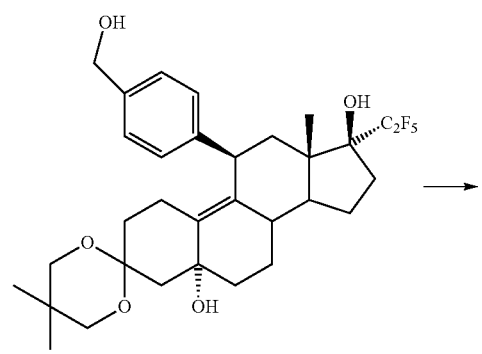

-continued

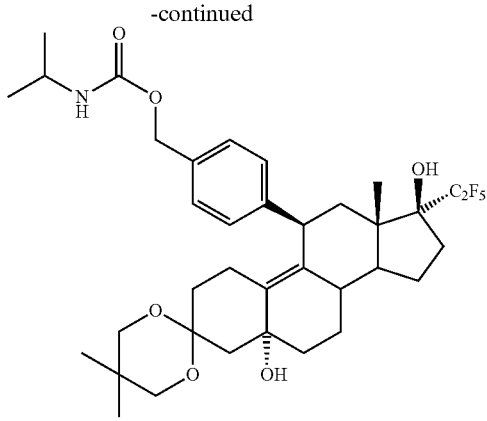

In analogy to Example 32a, 40 mg (67 µmol) of the compound prepared according to Example 17d were converted using isopropyl isocyanate and the title compound obtained after workup was converted further as a crude product.

EXAMPLE 43 allylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

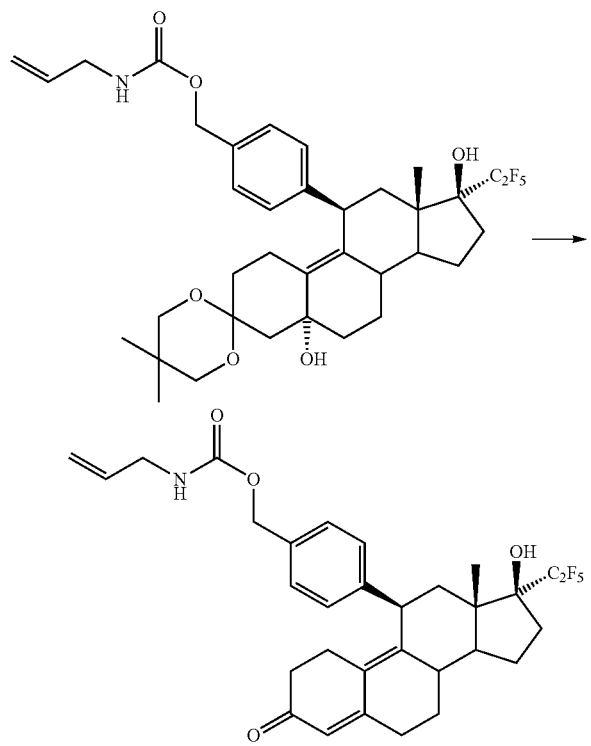

In analogy to Example 1, the crude product prepared in Example 43a was converted and, after workup and purification, 25 mg (63%) of the title compound were isolated as a colourless foam.

$^1$H NMR (CDCl$_3$): δ=0.60 (3H), 1.38-1.56 (2H), 1.72-1.88 (3H), 2.06 (1H), 2.19-2.64 (10H), 2.72 (1H), 3.81 (2H), 4.44 (1H), 4.83 (1H), 5.05 (2H), 5.12 (1H), 5.18 (1H), 5.78 (1H), 5.83 (1H), 7.16 (2H), 7.26 (2H) ppm.

EXAMPLE 43a allylcarbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

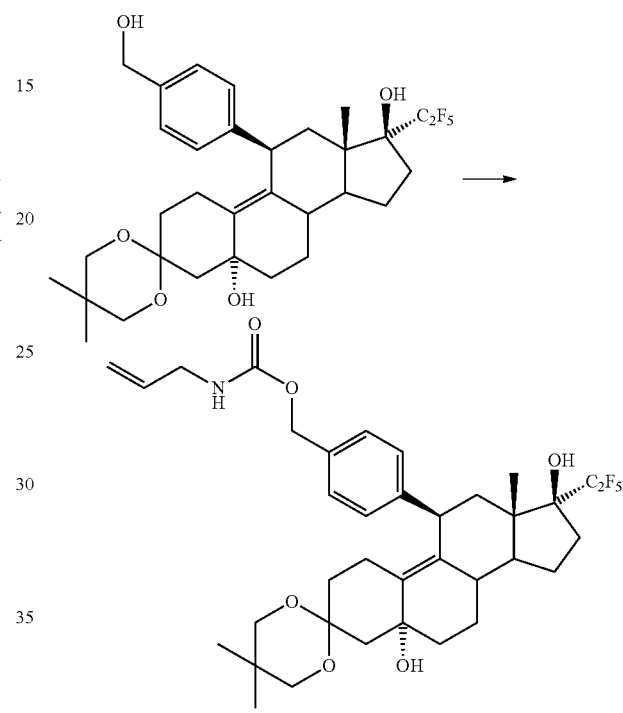

In analogy to Example 32a, 40 mg (67 µmol) of the compound prepared according to Example 17d were converted using allyl isocyanate and the title compound obtained after workup was converted further as a crude product.

EXAMPLE 44 tert-butylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

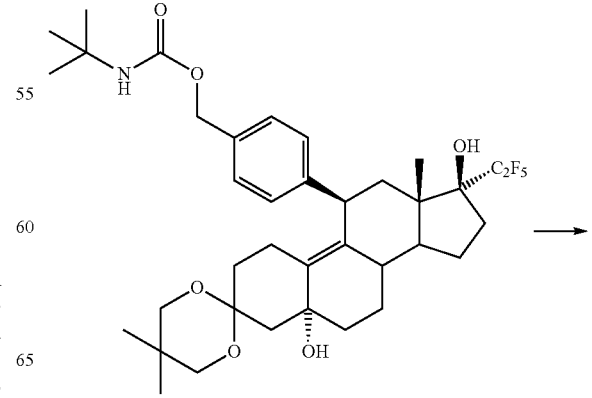

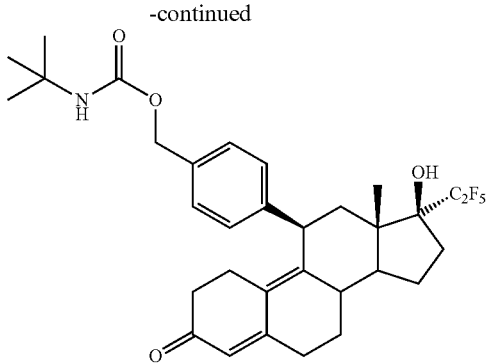

In analogy to Example 1, the crude product prepared in Example 44a was converted and, after workup and purification, 15 mg (38%) of the title compound were isolated as a colourless foam.

$^1$H NMR (CDCl$_3$): δ=0.59 (3H), 1.32 (9H), 1.40-1.56 (2H), 1.73-1.87 (3H), 2.06 (1H), 2.20-2.64 (10H), 2.72 (1H), 4.44 (1H), 4.71 (1H), 4.99 (2H), 5.78 (1H), 7.16 (2H), 7.25 (2H) ppm.

EXAMPLE 44a tert-butylcarbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

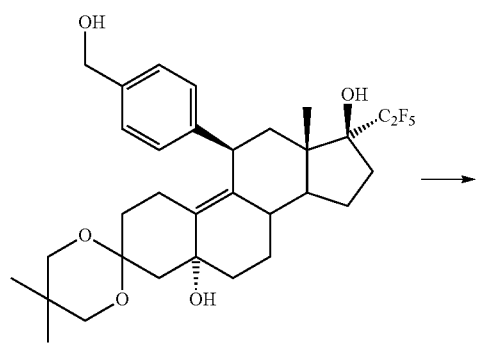

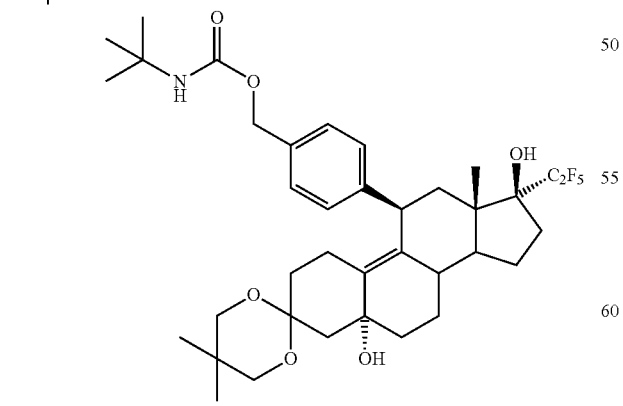

In analogy to Example 32a, 40 mg (67 μmol) of the compound prepared according to Example 17d were converted using tert-butyl isocyanate and the title compound obtained after workup was converted further as a crude product.

EXAMPLE 45

(4-piperidin-1-ylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

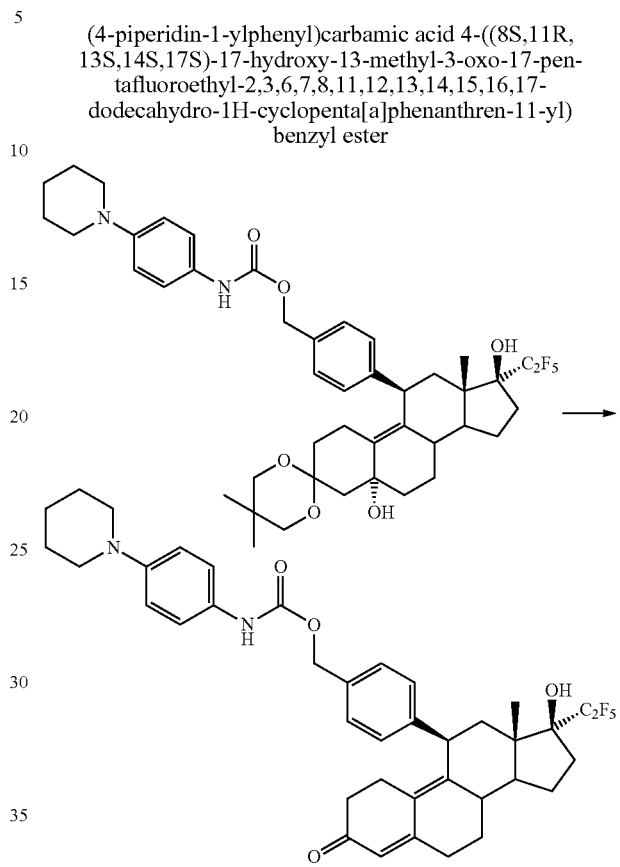

In analogy to Example 1, the crude product prepared in Example 45a was converted and, after workup and purification, 7.8 mg (17%) of the title compound were isolated as a colourless foam.

$^1$H NMR (CDCl$_3$): δ=0.59 (3H), 1.41-1.59 (4H), 1.65-1.85 (7H), 2.06 (1H), 2.12 (1H), 2.22-2.63 (9H), 2.72 (1H), 3.08 (4H), 4.45 (1H), 5.14 (2H), 5.78 (1H), 6.52 (1H), 6.89 (2H), 7.17 (2H), 7.24 (2H), 7.31 (2H) ppm.

EXAMPLE 45a (4-piperidin-1-ylphenyl)carbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

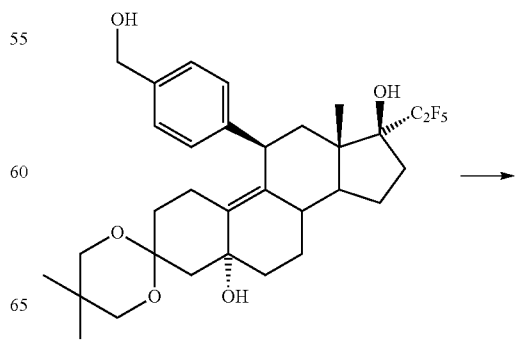

-continued

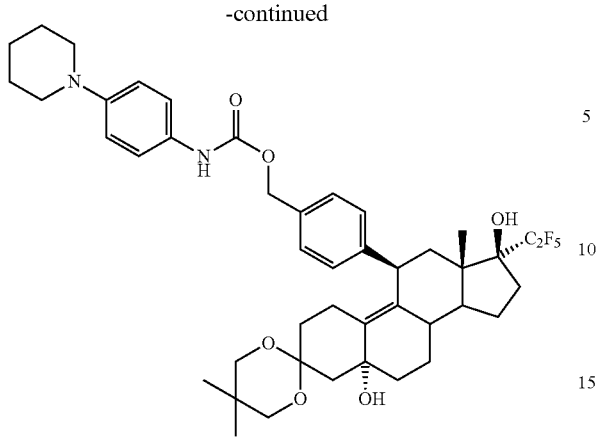

In analogy to Example 32a, 40 mg (67 μmol) of the compound prepared according to Example 17d were converted using 4-piperidinylphenyl isocyanate and the title compound obtained after workup was converted further as a crude product.

EXAMPLE 46 phenylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

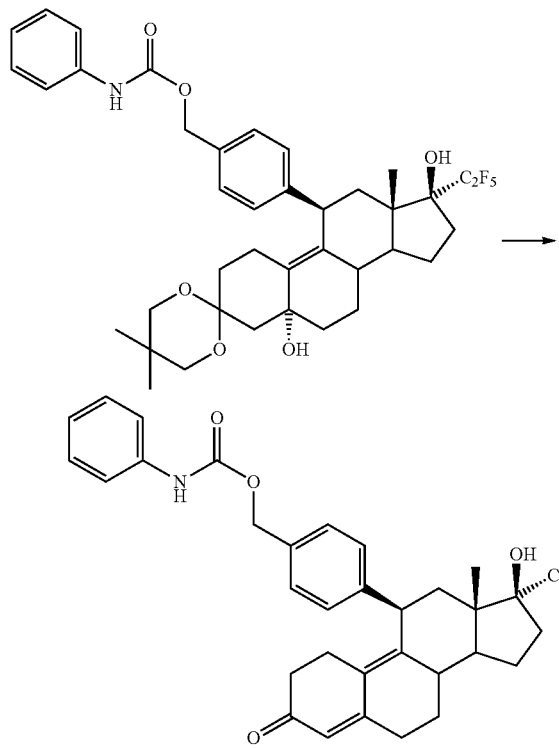

In analogy to Example 1, the crude product prepared in Example 46a was converted and, after workup and purification, 13 mg (34%) of the title compound were isolated as a colourless foam.

$^1$H NMR (CDCl$_3$): δ=0.60 (3H), 1.38-1.56 (2H), 1.73-1.87 (3H), 2.06 (1H), 2.10 (1H), 2.20-2.64 (9H), 2.72 (1H), 4.45 (1H), 5.16 (2H), 5.79 (1H), 6.67 (1H), 7.07 (1H), 7.18 (2H), 7.25-7.40 (6H) ppm.

EXAMPLE 46a phenylcarbamic acid 4-((5R,8S,11R,13S,14S,17S)-5,17-dihydroxy-17-pentafluoroethyl-5,5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

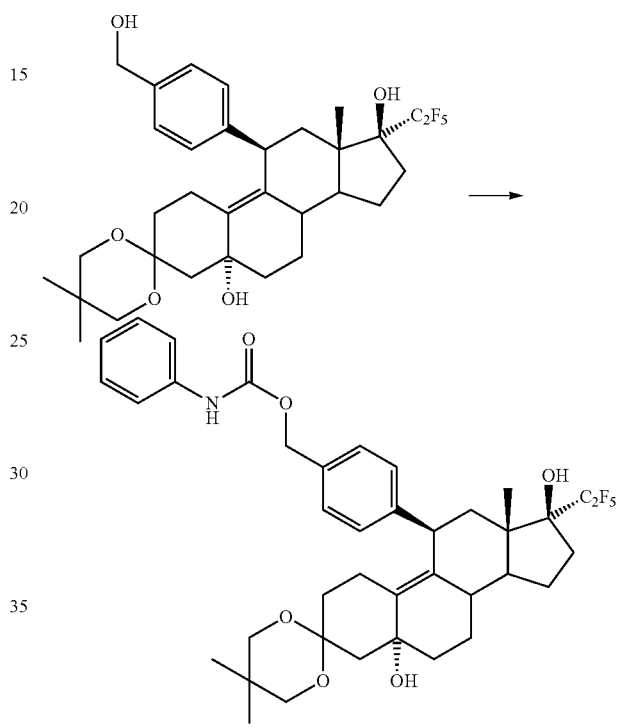

In analogy to Example 32a, 40 mg (67 μmol) of the compound prepared according to Example 17d were converted using phenyl isocyanate and the title compound obtained after workup was converted further as a crude product.

EXAMPLE 47

(4-methoxyphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthr en-11-yl)benzyl ester

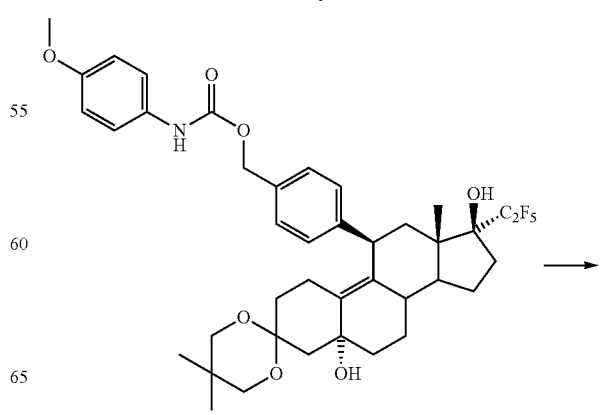

-continued

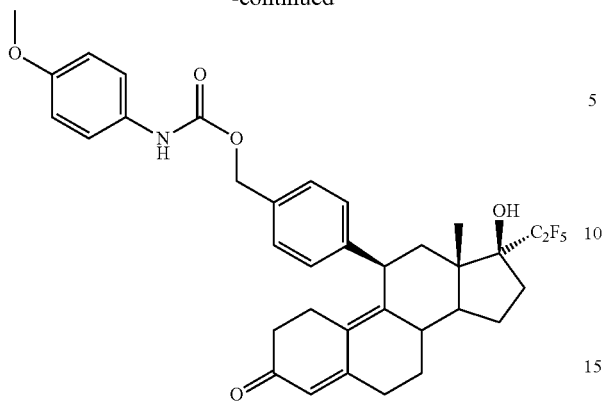

In analogy to Example 1, the crude product prepared in Example 47a was converted and, after workup and purification, 4.5 mg (10%) of the title compound were isolated as a colourless foam.

¹H NMR (CDCl₃): δ=0.60 (3H), 1.40-1.55 (2H), 1.73-1.87 (3H), 2.02 (1H), 2.06 (1H), 2.21-2.64 (9H), 2.72 (1H), 3.78 (3H), 4.45 (1H), 5.15 (2H), 5.78 (1H), 6.53 (1H), 6.85 (2H), 7.18 (2H), 7.28-7.34 (4H) ppm.

EXAMPLE 47a (4-methoxyphenyl)carbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

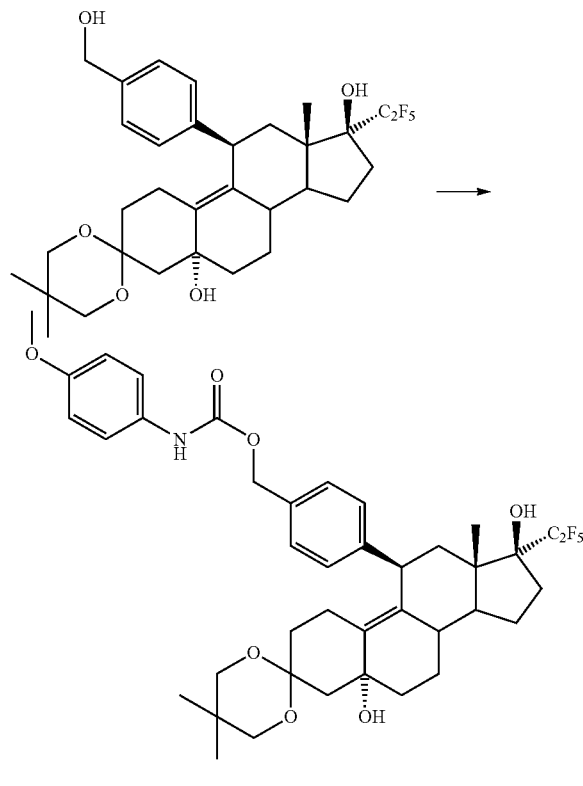

In analogy to Example 32a, 40 mg (67 μmol) of the compound prepared according to Example 17d were converted using 4-methoxyphenyl isocyanate and the title compound obtained after workup was converted further as a crude product.

EXAMPLE 48

(4-methylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

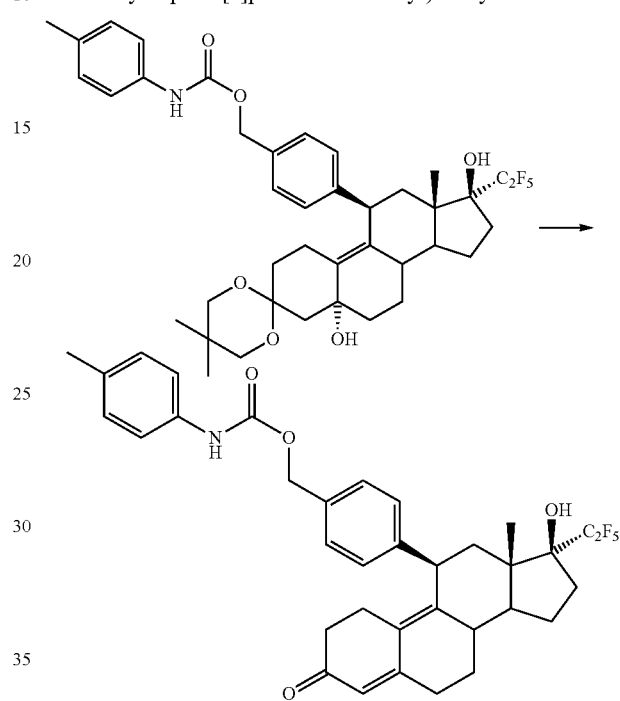

In analogy to Example 1, the crude product prepared in Example 48a was converted and, after workup and purification, 5.9 mg (14%) of the title compound were isolated as a colourless foam.

¹H NMR (CDCl₃): δ=0.60 (3H), 1.39-1.55 (2H), 1.73-1.87 (3H), 2.04 (1H), 2.07 (1H), 2.20-2.64 (9H), 2.30 (3H), 2.72 (1H), 4.45 (1H), 5.15 (2H), 5.78 (1H), 6.58 (1H), 7.10 (2H), 7.18 (2H), 7.25 (2H), 7.32 (2H) ppm.

EXAMPLE 48a (4-methylphenyl)carbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

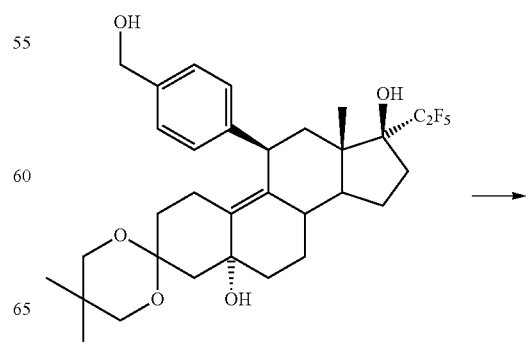

-continued

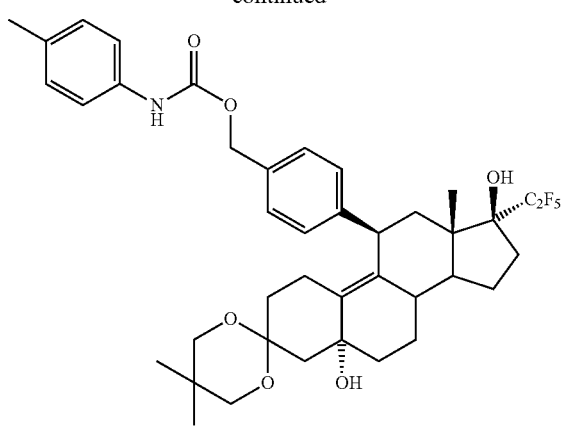

In analogy to Example 32a, 40 mg (67 μmol) of the compound prepared according to Example 17d were converted using 4-tolyl isocyanate and the title compound obtained after workup was converted further as a crude product.

EXAMPLE 49

(4-fluorophenyl)carbamic acid 4-((8S,11R,13S,14S, 17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

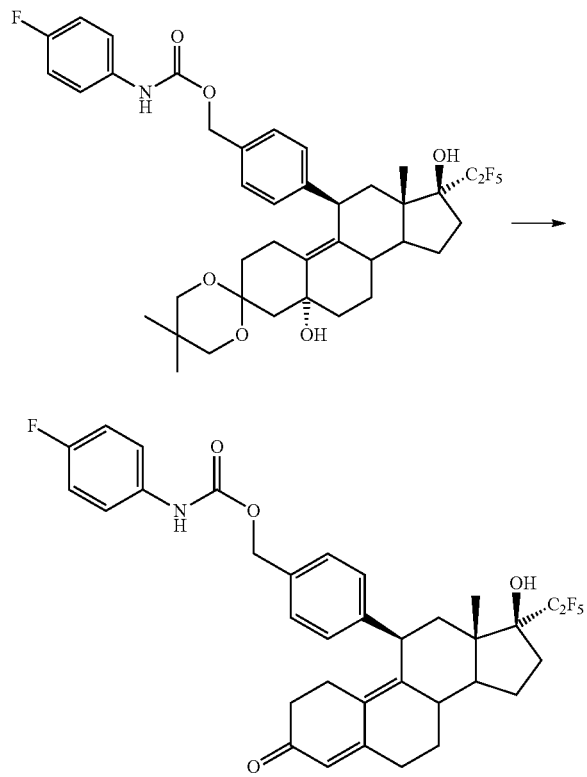

In analogy to Example 1, the crude product prepared in Example 49a was converted and, after workup and purification, 6 mg (14%) of the title compound were isolated as a colourless foam.

$^{1}$H NMR (CDCl$_3$): δ=0.60 (3H), 1.39-1.56 (2H), 1.73-1.87 (3H), 2.05 (1H), 2.07 (1H), 2.20-2.65 (9H), 2.72 (1H), 4.45 (1H), 5.15 (2H), 5.79 (1H), 6.63 (1H), 7.00 (2H), 7.18 (2H), 7.28-7.34 (4H) ppm.

EXAMPLE 49a (4-fluorophenyl)carbamic acid 4-((5R,8S,11R,13S, 14S,17S)-5,17-dihydroxy-17-pentafluoroethyl-5'5, 13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

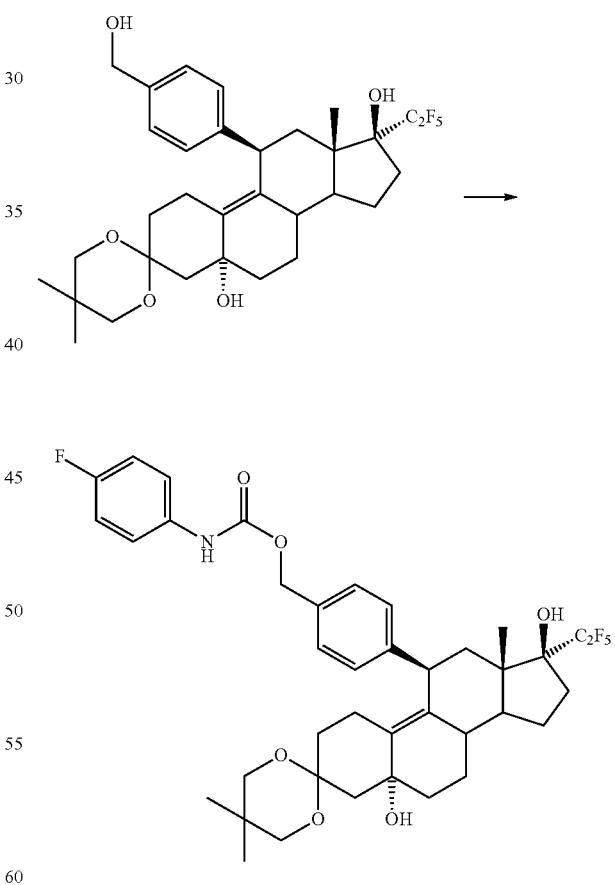

In analogy to Example 32a, 40 mg (67 μmol) of the compound prepared according to Example 17d were converted using 4-fluorophenyl isocyanate and the title compound obtained after workup was converted further as a crude product.

EXAMPLE 50

(4-chlorophenyl)carbamic acid 4-((8S,11R,13S,14S, 17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

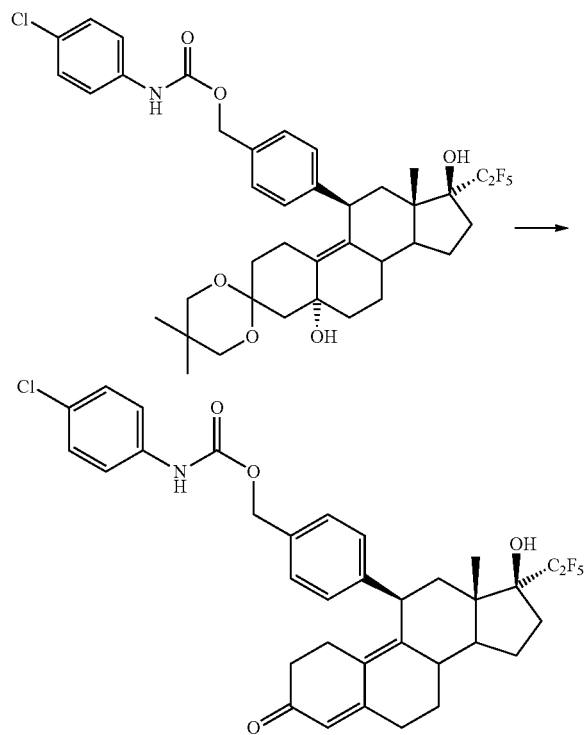

In analogy to Example 1, the crude product prepared in Example 50a was converted and, after workup and purification, 8.5 mg (20%) of the title compound were isolated as a colourless foam.

$^1$H NMR (CDCl$_3$): δ=0.60 (3H), 1.39-1.56 (2H), 1.73-1.87 (3H), 2.06 (1H), 2.07 (1H), 2.19-2.64 (9H), 2.72 (1H), 4.46 (1H), 5.15 (2H), 5.78 (1H), 6.68 (1H), 7.19 (2H), 7.22-7.36 (6H) ppm.

EXAMPLE 50a (4-chlorophenyl)carbamic acid 4-((5R,8S,11R,13S, 14S,17S)-5,17-dihydroxy-17-pentafluoroethyl-5'5, 13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

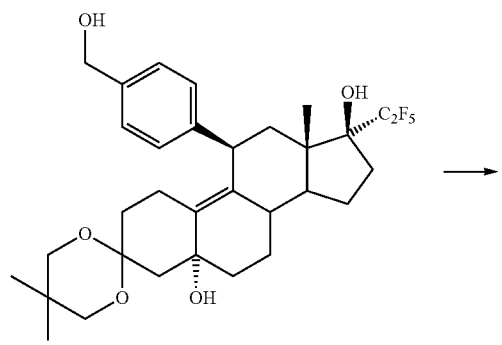

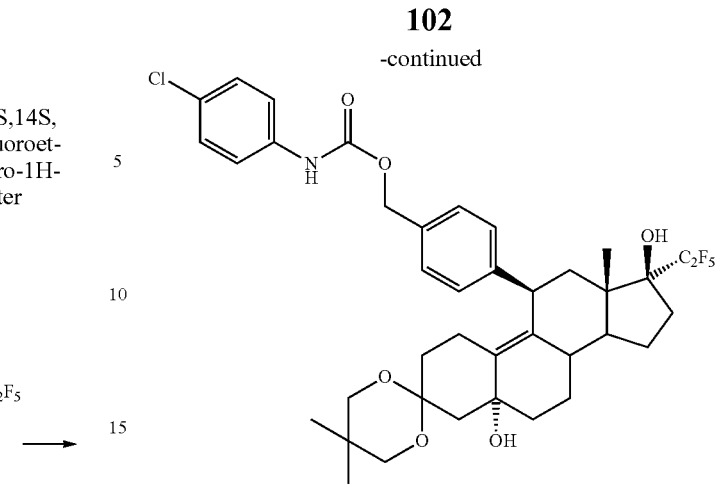

In analogy to Example 32a, 40 mg (67 μmol) of the compound prepared according to Example 17d were converted using 4-chlorophenyl isocyanate and the title compound obtained after workup was converted further as a crude product.

EXAMPLE 51

(4-tert-butylphenyl)carbamic acid 4-((8S,11R,13S, 14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl) benzyl ester

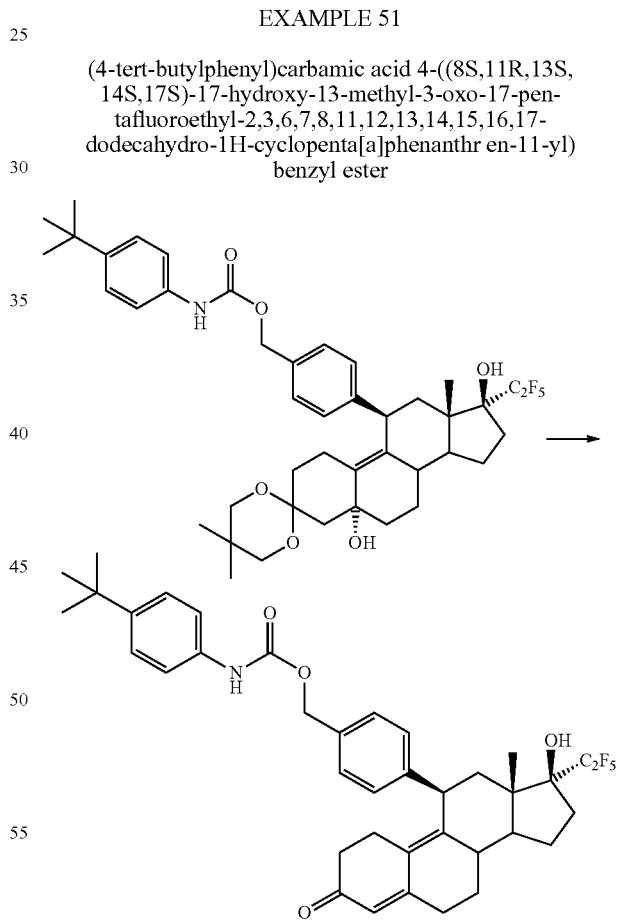

In analogy to Example 1, the crude product prepared in Example 51a was converted and, after workup and purification, 5.2 mg (12%) of the title compound were isolated as a colourless foam.

$^1$H NMR (CDCl$_3$): δ=0.60 (3H), 1.30 (9H), 1.40-1.55 (2H), 1.73-1.87 (3H), 2.02 (1H), 2.06 (1H), 2.21-2.64 (9H), 2.73 (1H), 4.45 (1H), 5.16 (2H), 5.79 (1H), 6.60 (1H), 6.65 (2H), 7.19 (2H), 7.28-7.34 (4H) ppm.

EXAMPLE 51a (4-tert-butylphenyl)carbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

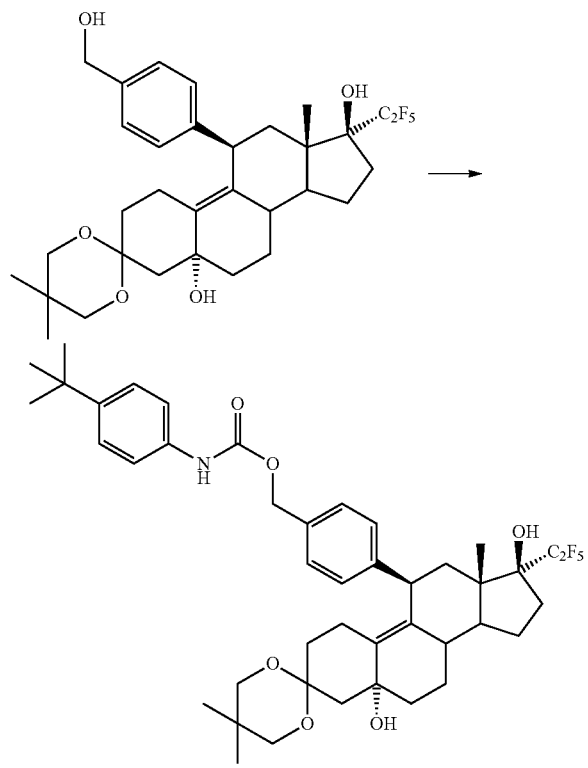

In analogy to Example 32a, 40 mg (67 µmol) of the compound prepared according to Example 17d were converted using tert-butylphenyl isocyanate and the title compound obtained after workup was converted further as a crude product.

EXAMPLE 52

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]benzoic acid ethyl ester

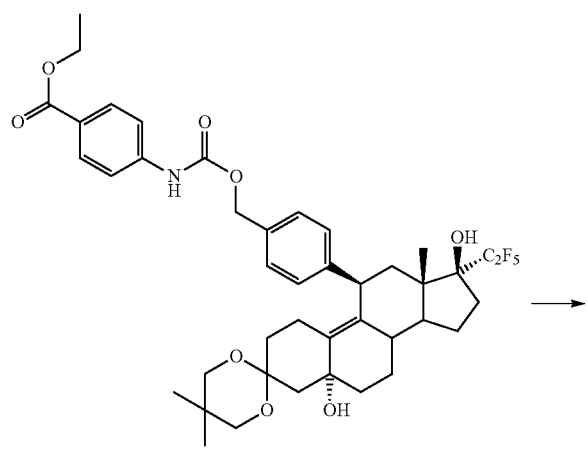

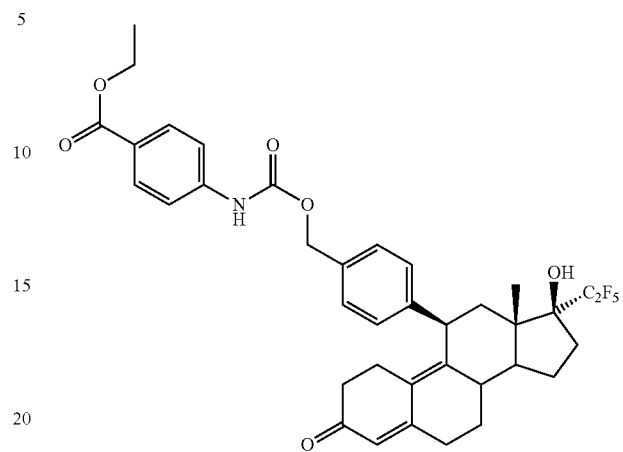

In analogy to Example 1, the crude product prepared in Example 52a was converted and, after workup and purification, 10 mg (24%) of the title compound were isolated as a colourless foam.

$^1$H NMR (CDCl$_3$): δ=0.60 (3H), 1.38 (3H), 1.38-1.55 (2H), 1.74-1.87 (3H), 2.02 (1H), 2.06 (1H), 2.20-2.64 (9H), 2.73 (1H), 4.35 (2H), 4.46 (1H), 5.18 (2H), 5.78 (1H), 6.85 (1H), 7.19 (2H), 7.32 (2H), 7.45 (2H), 7.99 (2H) ppm.

EXAMPLE 52a

4-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyloxycarbonylamino]benzoic acid ethyl ester

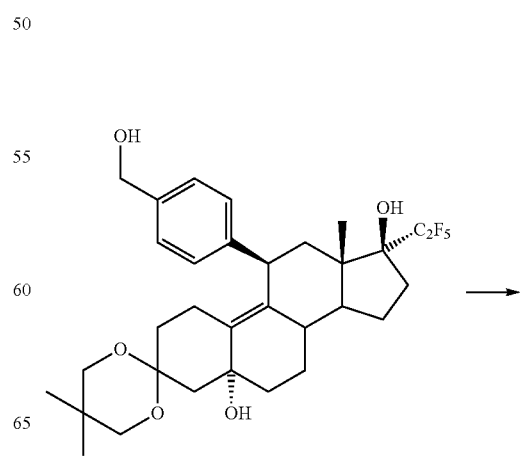

105

-continued

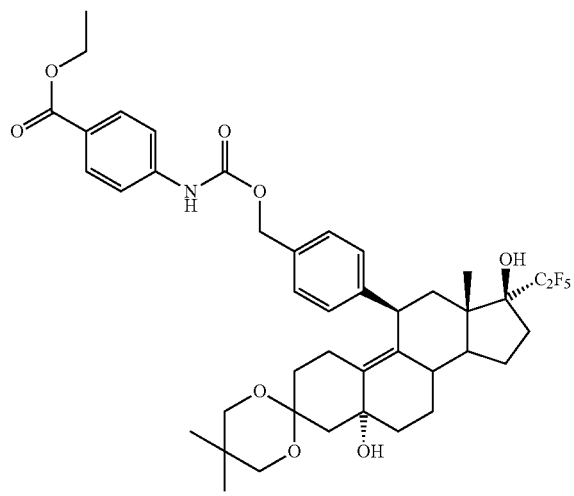

In analogy to Example 32a, 40 mg (67 μmol) of the compound prepared according to Example 17d were converted using ethyl 4-isocyanatobenzoate and the title compound obtained after workup was converted further as a crude product.

EXAMPLE 53

[4-(3,5-dimethylisoxazol-4-yl)phenyl]carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

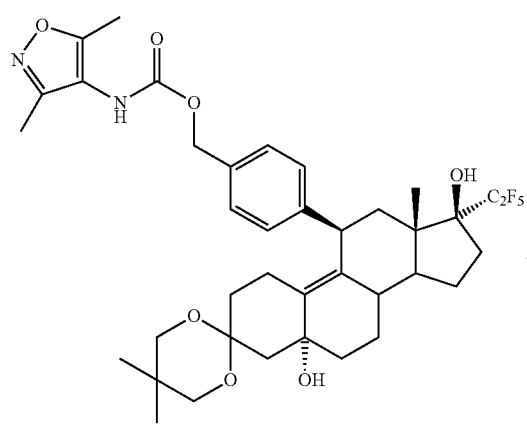

106

-continued

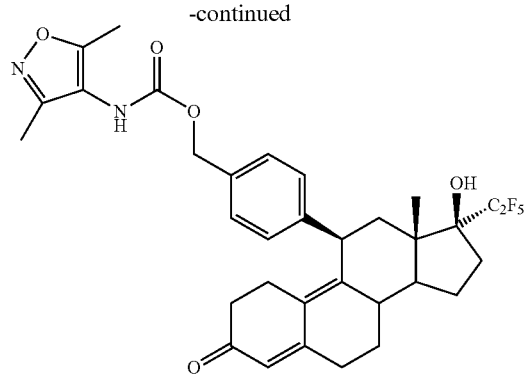

In analogy to Example 1, the crude product prepared in Example 53a was converted and, after workup and purification, 8.6 mg (20%) of the title compound were isolated as a colourless foam.

$^1$H NMR (CDCl$_3$): δ=0.59 (3H), 1.39-1.57 (2H), 1.72-1.88 (3H), 1.99-2.65 (17H), 2.73 (1H), 4.45 (1H), 5.13 (2H), 5.79 (1H), 5.86 (1H), 7.19 (2H), 7.28 (2H) ppm.

EXAMPLE 53a

[4-(3,5-dimethylisoxazol-4-yl)phenyl]carbamic acid 4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyl ester

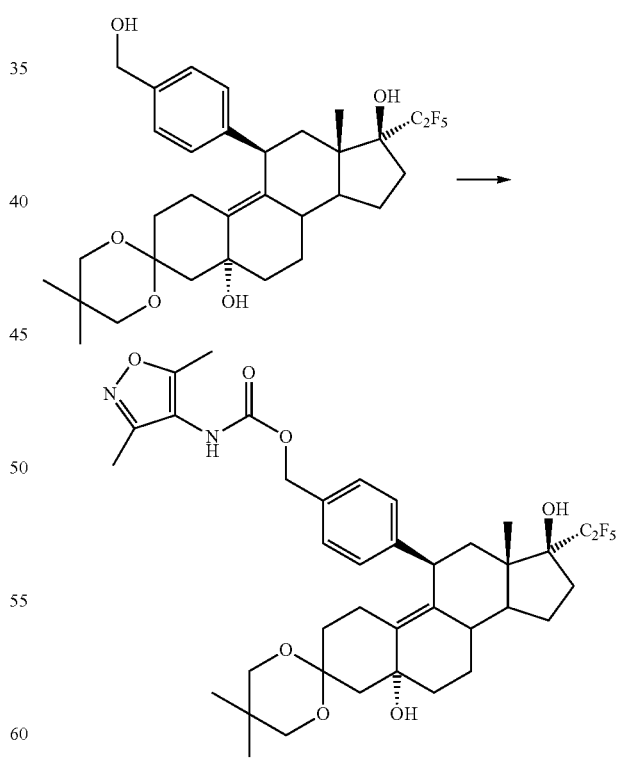

In analogy to Example 32a, 40 mg (67 μmol) of the compound prepared according to Example 17d were converted using 3,5-dimethylisoxazol-4-yl isocyanate and the title compound obtained after workup was converted further as a crude product.

EXAMPLE 54

N-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]nicotinamide

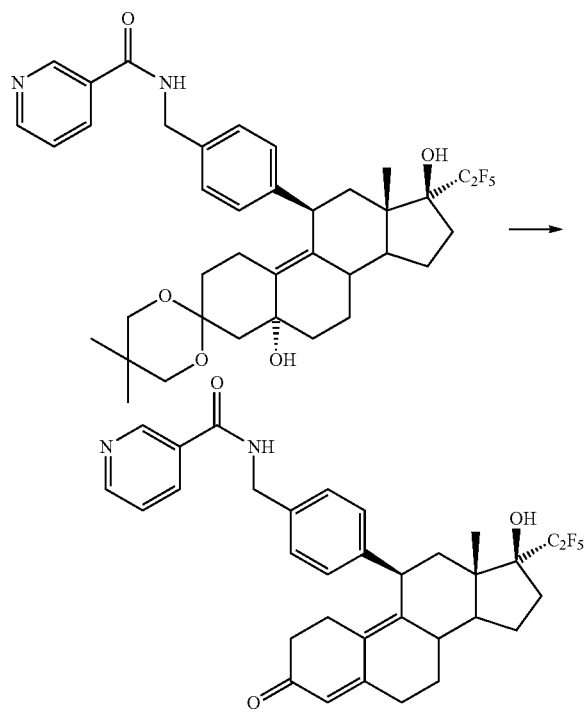

In analogy to Example 1, 48 mg (68 µmol) of the compound prepared according to Example 54a were converted and, after workup and purification, 5.0 mg (13%) of the title compound were isolated as a colourless foam.

$^1$H NMR (CDCl$_3$): δ=0.60 (3H), 1.38-1.56 (2H), 1.72-1.88 (3H), 2.06 (1H), 2.18-2.63 (9H), 2.66 (1H), 2.72 (1H), 4.43 (1H), 4.61 (2H), 5.77 (1H), 6.63 (1H), 7.15 (2H), 7.25 (2H), 7.39 (1H), 8.14 (1H), 8.71 (1H), 8.96 (1H) ppm.

EXAMPLE 54a

N-[4-((5R,8S,11R,13S,14S,17S)-5,17-dihydroxy-17-pentafluoroethyl-5'5,13-trimethyl-1,2,3,4,6,7,8,11,12,13,14,15,16,17-tetradecahydrospiro[cyclopenta[a]phenanthrene-3,2'-[1,3]dioxan]-11-yl)benzyl]nicotinamide

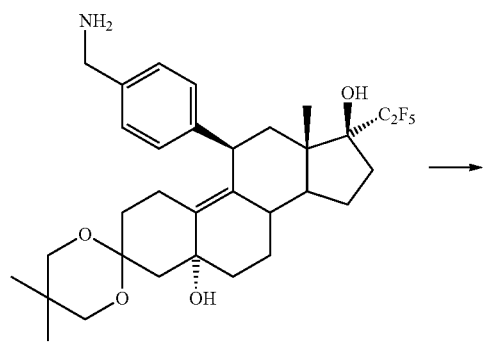

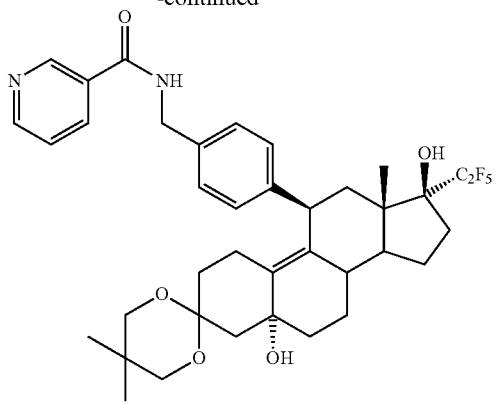

The solution of 40 mg (67 µmol) of the compound prepared according to Example 17b in a mixture of 1 ml of dichloromethane and 20 µl of dimethylformamide was admixed with 9 mg of nicotinyl chloride and stirred at 23° C. for 2 hours. The mixture was concentrated and the resulting crude product was converted further without purification.

EXAMPLE 55

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]propionic acid

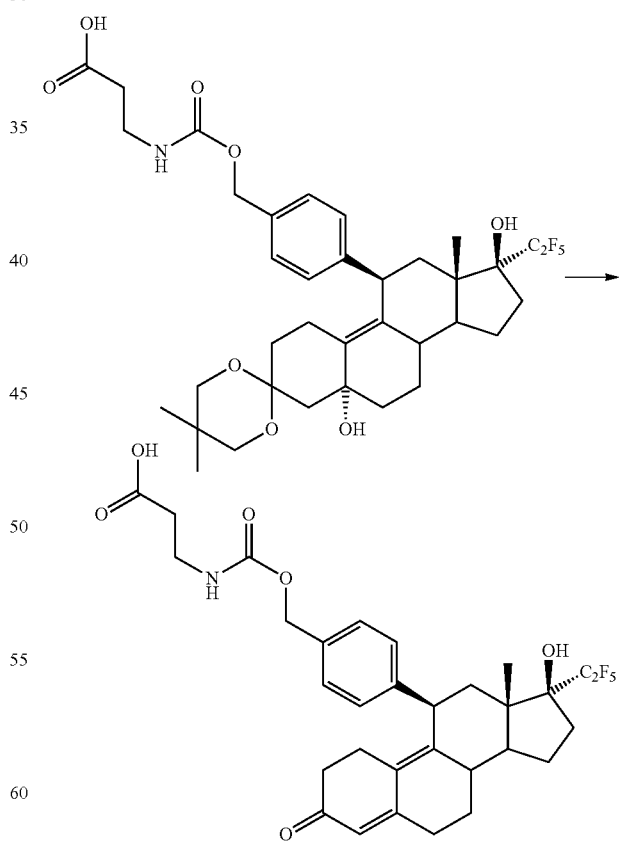

In analogy to Example 1, 52 mg (73 µmol) of the compound prepared according to Example 55a were converted and, after workup and purification, 14 mg (32%) of the title compound were isolated as a colourless foam.

¹H NMR (CD₃OD): δ=0.57 (3H), 1.36-1.56 (2H), 1.70-1.82 (3H), 2.09 (1H), 2.16-2.46 (7H), 2.54-2.73 (4H), 2.79 (1H), 3.33 (2H), 4.52 (1H), 5.00 (2H), 5.73 (1H), 7.21 (2H), 7.26 (2H) ppm.

EXAMPLE 55a

3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyloxycarbonylamino]propionic acid

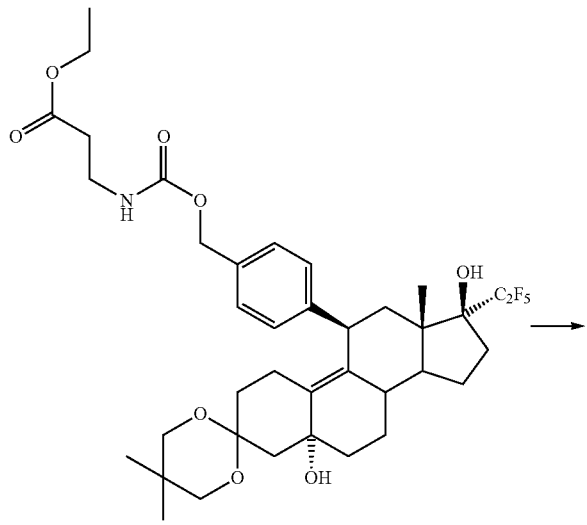

In analogy to Example 26a, 82 mg (0.11 mmol) of the compound prepared according to Example 55b were converted and, after workup, 59 mg (77%) of the title compound were isolated as a colourless foam.

EXAMPLE 55b

3-[4-((5R,8S,11R,13S,14S,17S)-5,17-dihydroxy-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxan]-11-yl)benzyloxycarbonylamino]propionic acid ethyl ester

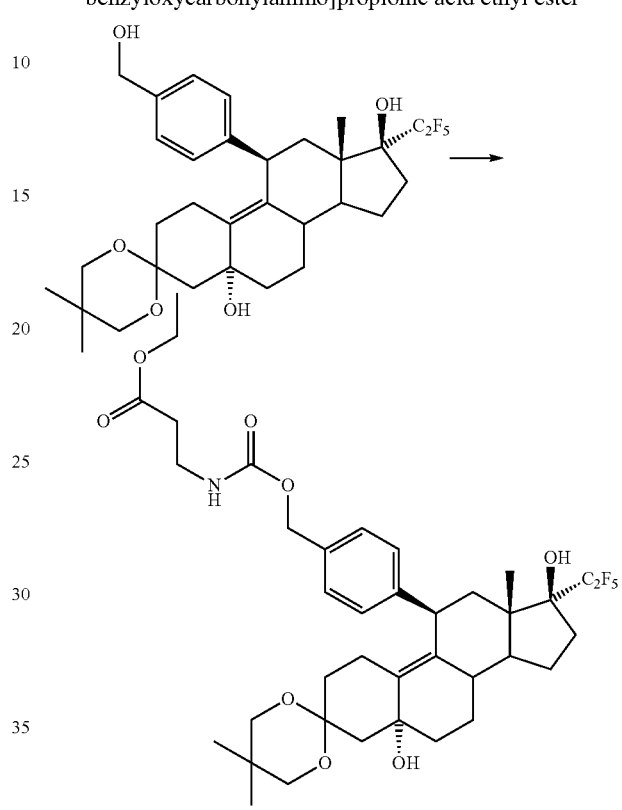

In analogy to Example 32a, 100 mg (0.17 mmol) of the compound prepared according to Example 17d were converted using ethyl 3-isocyanatopropionate and the title compound obtained after workup was converted further as a crude product.

EXAMPLE 56 benzylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester

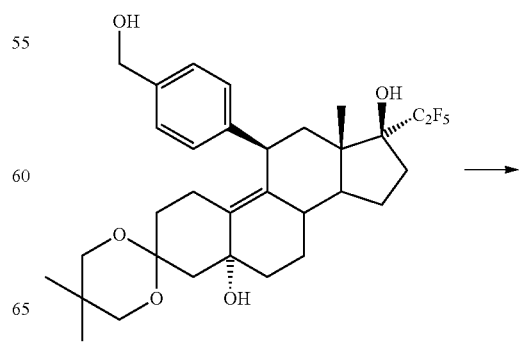

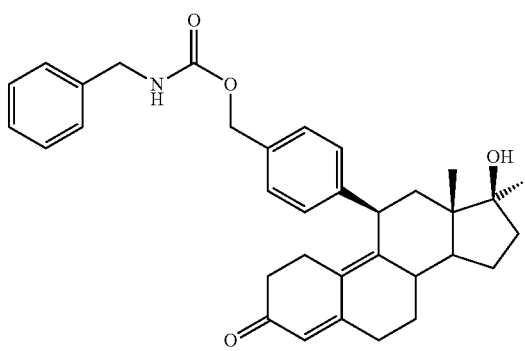

In analogy to Example 32a, 50 mg (83 µmol) of the compound prepared according to Example 17d were converted using benzyl isocyanate and the crude product obtained after workup was converted further in analogy to Example 1. After workup and purification, 14 mg (27%) of the title compound were isolated as a colourless foam.

$^1$H NMR (CDCl$_3$): δ=0.59 (3H), 1.42-1.55 (2H), 1.75-1.86 (3H), 2.06 (1H), 2.22-2.63 (10H), 2.72 (1H), 4.39 (2H), 4.45 (1H), 5.05 (1H), 5.09 (2H), 5.78 (1H), 7.17 (2H), 7.24-7.35 (7H) ppm.

EXAMPLE 57

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]propionic acid ethyl ester

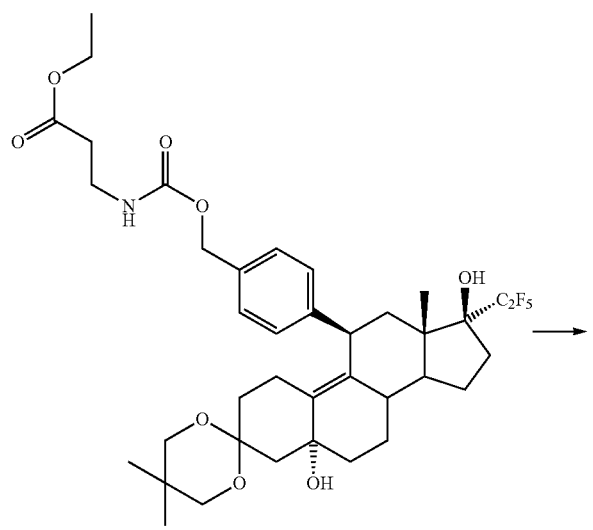

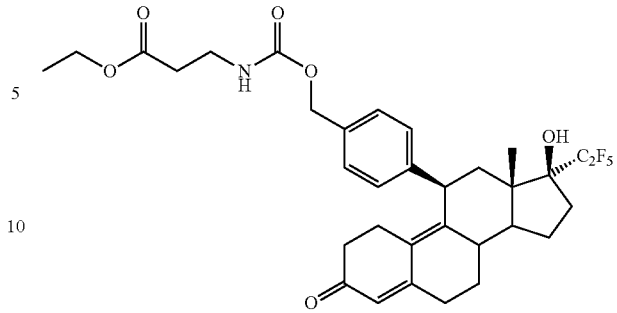

In analogy to Example 1, 72 mg (97 µmol) of the compound prepared according to Example 55b were converted and, after workup and purification, 6.1 mg (10%) of the title compound were isolated as a colourless foam.

$^1$H NMR (CDCl$_3$): δ=0.59 (3H), 1.26 (3H), 1.42-1.56 (2H), 1.74-1.89 (3H), 2.07 (1H), 2.14 (1H), 2.22-2.67 (11H), 2.72 (1H), 3.47 (2H), 4.14 (2H), 4.45 (1H), 5.04 (2H), 5.28 (1H), 5.78 (1H), 7.16 (2H), 7.26 (2H) ppm.

EXAMPLE 58

Progesterone Receptor-Antagonistic Action in Stable Transfectants of Human Neuroblastoma Cells (SK-N-MC Cells) with the Human Progesterone A or Progesterone B Receptor and an MN-LUC Reporter Construct SK-N-MC cells (human neuroblastoma cells) which have been stably transfected with plasmids expressing the human progesterone receptor B (pRChPR-B-neo) or the human progesterone receptor A (pRChPR-A-neo) and a reporter construct (pMMTV-LUC) were incubated for 24 hours either in the absence (negative control) or in the presence of ascending amounts of the particular test compound (0.01 nmol/l, 0.1 nmol/l, 1 nmol/l, 10 nmol/l, 100 nmol/l and 1 pmol/l), in order to determine the agonistic efficacy. As a positive control of the reporter gene induction, the cells were treated with the synthetic gestagen promegestone (0.01 nmol/l, 0.1 nmol/l, 1 nmol/l, 10 nmol/l, 100 nmol/l and 1 pmol/l). To determine the antagonistic activity, the cells were treated with 0.1 nmol/l promegestone and additionally with ascending amounts of the particular test compound (0.01 nmol/l, 0.1 nmol/l, 1 nmol/l, 10 nmol/l, 100 nmol/l and 1 pmol/l). The activity of the reporter gene LUC (LUC=luciferase) was determined in the cell lysates and measured as RLU (relative light units). All measurements are reported as % efficacy and as EC$_{50}$ and IC$_{50}$ concentrations.

a) Agonistic Activity:

None of the compounds mentioned exhibits agonistic activity.

b) Antagonistic Activity:

All compounds mentioned exhibit 100% antagonistic activity.

The antagonistic potency of the compounds is summarized in Table 1.

TABLE 1

Antagonistic potency of the compounds

| Ex. | PR-A IC$_{50}$ [nM] | PR-B IC$_{50}$ [nM] |
|---|---|---|
| 1 | <0.001 | 0.004 |
| 2 | 0.095 | 0.11 |
| 3 | 0.09 | 0.04 |
| 4 | 0.012 | 0.012 |
| 5 | 0.016 | 0.09 |
| 6A | 0.1 | 0.1 |
| 6B | nd | nd |
| 7 | 0.08 | 0.09 |
| 8 | 0.08 | 0.09 |
| 9 | 0.06 | 0.1 |
| 10 | 5 | 3 |
| 11 | 2 | 3 |
| 12 | 4 | 9 |
| 13 | 4 | 7 |
| 14 | 1 | 1 |
| 15A | 0.09 | 0.1 |
| 15B | 0.01 | 0.01 |
| 16 | 0.8 | 1.0 |
| 17 | 0.4 | 0.8 |
| 18 | 0.8 | 0.8 |
| 19 | 0.6 | 0.7 |
| 20 | 0.7 | 1.0 |
| 21 | 1.2 | 2.4 |
| 22 | 0.5 | 0.6 |
| 23 | 0.3 | 0.8 |
| 24 | 0.4 | 0.5 |
| 25 | 0.3 | 0.6 |
| 26 | 24 | 64 |
| 27 | 43 | 29 |
| 28 | 0.01 | 0.08 |
| 29 | 0.3 | 0.9 |
| 30 | 0.02 | 0.08 |
| 31 | 138 | 137 |
| 32 | 0.1 | 0.2 |
| 33 | 0.8 | 0.8 |
| 34 | 0.7 | 0.8 |
| 35 | 0.3 | 0.6 |
| 36 | 0.7 | 0.8 |
| 37 | 0.8 | 0.9 |
| 38 | 25 | 36 |
| 39 | 0.1 | 0.2 |
| 40 | 0.01 | 0.05 |
| 41 | 0.09 | 0.1 |
| 42 | 0.1 | 0.2 |
| 43 | 0.1 | 0.1 |
| 44 | 0.1 | 0.1 |
| 45 | 0.02 | 0.09 |
| 46 | 0.01 | 0.01 |
| 47 | nd | nd |
| 48 | 0.07 | 0.2 |
| 49 | 0.09 | 0.1 |
| 50 | 0.1 | 0.4 |
| 51 | nd | nd |
| 52 | 0.1 | 0.1 |
| 53 | 0.09 | 0.03 |
| 54 | 0.3 | 0.1 |
| 55 | 8 | 10 |
| 56 | 0.2 | 0.3 |
| 57 | 0.1 | 0.1 | nd: not determined

Preference is given to compounds which have an antagonistic potency with an IC$_{50}$ of <1.0 nM.

Particular preference is given to compounds which have an antagonistic potency with an IC$_{50}$ of ≤0.1 nM.

EXAMPLE 59

Determination of Metabolic Stability in Human and Rat Liver Microsomes

Isolated human liver microsomes (HLM) were used to assess the metabolic stability of compounds of general formula I.

The incubations were conducted with 2.4 ml of HLM solution (protein content 0.5 mg/ml), 30 µl of the test compound (final concentration 1 µM) and 0.6 ml of the cofactor mixture (=NADPH-generating system composed of 3 IU glucose-6-phosphate dehydrogenase, 14.6 mg glucose-6-phosphate, 1.2 mg NADP) at 37° C. in 100 mM phosphate buffer at pH 7.4. Samples were taken at 6 time points (2-60 min) and precipitated with an equal volume of methanol, and the recovery of the test substances used in the supernatant was determined by LC-MS/MS analysis. The half-life of substance degradation determined therefrom was used to calculate what is called the intrinsic clearance of the substance in the liver microsome preparation. With the aid of this, together with various physiological parameters (human hepatic blood flow: 1.3 l*kg/h; specific liver weight (per kg of body weight): 21 g/kg; microsomal protein content: 40 mg/g of liver), in accordance with the well-stirred model, (metabolic) in vivo clearance in relation to phase I reactions was predicted. In addition, under the assumptions that (i) absorption of the test substance is 100%, and (ii) the first pass is completely reflected by liver microsome metabolism, a maximum oral bioavailability (Fmax) was calculated.

Some of the compounds tested have a predicted oral bioavailability for humans of Fmax<50%, and they are therefore particularly suitable for local administrations requiring reduced systemic stability. Examples include the compounds specified in Examples 2-9, 15, 17, 23, 24, 40 and 41 (see Table 2).

TABLE 2

| Example | Predicted Cl$_{int}$ [l/h/kg] | | Predicted F$_{max}$ [%] (maximum oral bioavailability) | |
|---|---|---|---|---|
| | rat | human | rat | human |
| 1 | 1.6 | 0.44 | 61 | 66 |
| 2 | 3.46 | 1.21 | 18 | 8 |
| 3 | 3.6 | 1.3 | 15 | 4.0 |
| 4 | 2.0 | 0.82 | 52 | 37 |
| 5 | 2.0 | 0.7 | 52 | 44 |
| 6 | 1.2 | 0.72 | 71 | 46 |
| 7 | 3.3 | 1.3 | 20 | 3.4 |
| 8 | 3.4 | 1.3 | 19 | 2.5 |
| 9 | 3.99 | 1.12 | 4.9 | 16 |
| 15A | 1.7 | 1.21 | 59 | 8.5 |
| 15B | 4.0 | 1.25 | 4.7 | 5.0 |
| 17 | 1.6 | 1.17 | 63 | 12 |
| 23 | 3.0 | 1.27 | 29 | 4 |
| 24 | 1.0 | 1.08 | 77 | 18 |
| 29 | 0.3 | 0.41 | 93 | 69 |
| 30 | 0.9 | 0.49 | 79 | 63 |
| 40 | 2.2 | 1.21 | 47 | 8.0 |
| 41 | 2.1 | 1.17 | 49 | 11 |

Very particular preference for systemic administrations is given to those compounds which each have a predicted maximum bioavailability greater than 60% in different species (rats, humans).

Very particular preference for local administrations is given to those compounds which have a predicted maximum bioavailability for humans which is less than 50%.

The invention claimed is:

1. A compound of the formula (II)

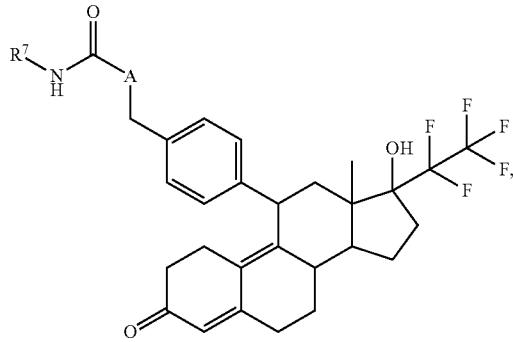

in which

A is either —O— or —NH— and $R^7$ is $C_1$-$C_4$-alkyl, allyl, phenyl optionally substituted in the para-position by the $C_1$-$C_4$-alkyl, —CN, $C_1$-$C_4$-alkoxy, halogen, $C_1$-$C_4$-alkanoyloxy, —$CO_2H$, —$CO_2C_{1-4}$-alkyl or piperidinyl groups,

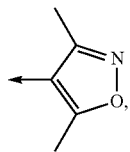

benzyl, —$(CH_2)$m-$COOR^8$ where m=1, 2 or 3 and $R^8$=hydrogen or $C_1$-$C_4$-alkyl or a salt thereof.

2. A compound of the formula (III)

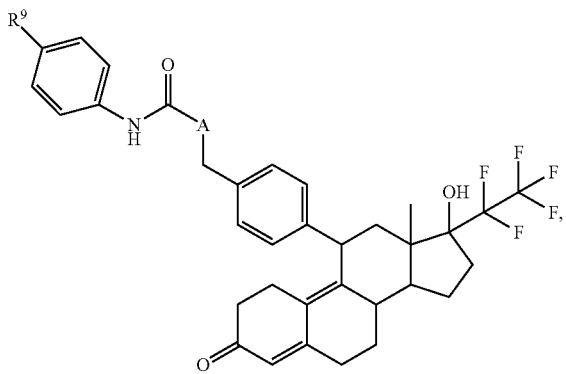

in which

A is either —O— or —NH— and $R^9$ is hydrogen, $C_1$-$C_4$-alkyl, —CN, $C_1$-$C_4$-alkoxy, halogen, —$CO_2H$, —$CO_2C_1$-4-alkyl or piperidinyl or a salt thereof.

3. A compound according of the formula (IV)

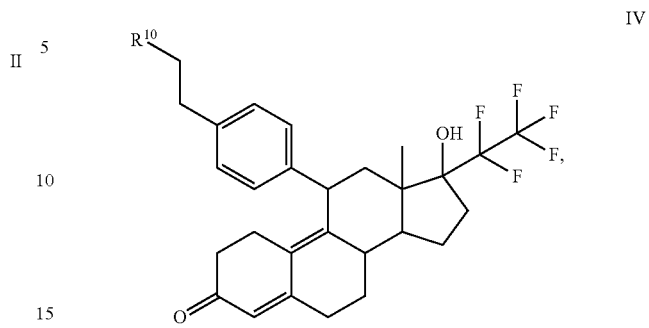

in which $R^{10}$ is optionally methyl-substituted pyridinyl or thiazolyl, —CN, or or a salt thereof.

4. The compound of claim 1 selected from the group consisting of:
1-ethyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;
1-allyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;
1-isopropyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;
1-tert-butyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;
{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}acetic acid ethyl ester;
3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}propionic acid ethyl ester;
1-benzyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;
{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}acetic acid;
3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}propionic acid;
ethylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;
isopropylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

allylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

tert-butylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

[4-(3,5-dimethylisoxazol-4-yl)phenyl]carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]propionic acid;

benzylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester; or 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]propionic acid ethyl ester.

5. A method of treatment of fibroids of the uterus, endometriosis, heavy menstrual bleeds, meningiomas, or breast cancers, or for fertility control or emergency contraception, comprising the step of administering a compound according to claim 1 to a patient in need thereof.

6. A pharmaceutical composition comprising the compound of claim 1 and an inert, non-toxic, pharmaceutically suitable excipient.

7. A pharmaceutical composition comprising the compound of claim 2 and an inert, non-toxic, pharmaceutically suitable excipient.

8. A method of treatment of fibroids of the uterus, endometriosis, heavy menstrual bleeds, meningiomas, or breast cancers, or for fertility control or emergency contraception, comprising the step of administering the compound of claim 2 to a patient in need thereof.

9. The compound of claim 2, selected from the group consisting of:

1-phenyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-p-tolylurea;

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-(4-methoxyphenyl)urea;

1-(4-fluorophenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;

1-(4-chlorophenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;

1-(4-tert-butylphenyl)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}benzoic acid ethyl ester;

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]ureido}benzoic acid;

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-(4-piperidin-1-ylphenyl)urea (4-piperidin-1-ylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

phenylcarbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

(4-methoxyphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

(4-methylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

(4-fluorophenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

(4-chlorophenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester;

(4-tert-butylphenyl)carbamic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl ester; and 4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyloxycarbonylamino]benzoic acid ethyl ester.

10. A pharmaceutical composition comprising the compound of claim 3 and an inert, non-toxic, pharmaceutically suitable excipient.

11. A method of treatment of fibroids of the uterus, endometriosis, heavy menstrual bleeds, meningiomas, or breast cancers, or for fertility control or emergency contraception, comprising the step of administering the compound of claim 3 to a patient in need thereof.

12. The compound of claim 4, selected from the group consisting of:

(8S,11R,13S,14S,17S)-17-hydroxy-13-methyl-17-pentafluomethyl-11-[4-(2-pyridin-2-ylethyl)phenyl]-1,2,6,7,8,11,12,13,14,15,16,17-dodecahydrocyclopenta[a]phenanthren-3-one;

(8S,11R,13S,14S,17S)-17-hydroxy-13-methyl-11-{4-[2-(2-methylthiazol-4-yl)ethyl]phenyl}-17-pentafluoroethyl-1,2,6,7,8,11,12,13,14,15,16,17-dodecahydrocyclopenta[a]phenanthren-3-one;

(8S,11R,13S,14S,17S)-17-hydroxy-13-methyl-17-pentafluoroethyl-11-[4-(2-pyridin-3-ylethyl)phenyl]-1,2,6,7,8,11,12,13,14,15,16,17-dodecahydrocyclopenta[a]phenanthren-3-one;

(8S,11R,13S,14S,17S)-17-hydroxy-13-methyl-17-pentafluoroethyl-11-[4-(2-pyridin-4-ylethyl)phenyl]-1,2,6,7,8,11,12,13,14,15,16,17-dodecahydrocyclopenta[a]phenanthren-3-one; and 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propionitrile.

* * * * *